US008404709B2

(12) United States Patent
Figueroa Perez et al.

(10) Patent No.: US 8,404,709 B2
(45) Date of Patent: Mar. 26, 2013

(54) SUBSTITUTED 4-ARYL-1,4-DIHYDRO-1,6-NAPHTHYRIDINES AND USE THEREOF

(75) Inventors: Santiago Figueroa Perez, Leverkusen (DE); Peter Kolkhof, Wuppertal (DE); Lars Bärfacker, Oberhausen (DE); Ingo Flamme, Reichshof (DE); Karl-Heinz Schlemmer, Wuppertal (DE); Rolf Grosser, Leverkusen (DE); Klaus Münter, Wülfrath (DE); Andreas Knorr, Erkrath (DE); Adam Nitsche, Pulheim (DE)

(73) Assignee: Bayer Intellectual Property GmbH, Monheim (DE)

( * ) Notice: Subject to any disclaimer, the term of this patent is extended or adjusted under 35 U.S.C. 154(b) by 554 days.

(21) Appl. No.: 12/303,719

(22) PCT Filed: Jun. 1, 2007

(86) PCT No.: PCT/EP2007/004865
§ 371 (c)(1), (2), (4) Date: Jun. 28, 2010

(87) PCT Pub. No.: WO2007/140934
PCT Pub. Date: Dec. 13, 2007

(65) Prior Publication Data
US 2010/0305052 A1 Dec. 2, 2010

(51) Int. Cl.
*A01N 43/42* (2006.01)
*A61K 31/44* (2006.01)
*C07D 471/02* (2006.01)

(52) U.S. Cl. ...................... 514/300; 546/123
(58) Field of Classification Search ............ 514/300; 546/123
See application file for complete search history.

(56) References Cited

U.S. PATENT DOCUMENTS

| 4,621,082 A | 11/1986 | Meyer et al. |
| 4,681,882 A | 7/1987 | Kleinschroth et al. |
| 4,698,341 A | 10/1987 | Satzinger et al. |
| 4,711,901 A | 12/1987 | Satzinger et al. |
| 4,751,228 A * | 6/1988 | Kleinschroth et al. ........ 514/300 |
| 4,760,081 A | 7/1988 | Satzinger et al. |
| 4,762,837 A | 8/1988 | Kleinschroth et al. |

FOREIGN PATENT DOCUMENTS

| EP | 0133530 A2 | 2/1985 |
| EP | 0173933 | 3/1986 |
| EP | 0189898 A1 | 8/1986 |
| EP | 0234516 A1 | 9/1987 |
| WO | 0210164 * | 2/2002 |
| WO | WO 02/10164 | 2/2002 |
| WO | WO 2005/087740 | 9/2005 |
| WO | WO 2005/097118 | 10/2005 |
| WO | WO-2006/066011 A2 | 6/2006 |
| WO | WO-2007/009670 A1 | 1/2007 |

OTHER PUBLICATIONS

R. E. Booth et al.: "Aldosterone," Advances in Physiology Rducation, vol. 26, No. 1, Mar. 2002, pp. 8-20.
B. Pitt et al.: "Eplerenone, A Selective Aldosterone Blocker, in Patients with Left Ventricular Dysfunction after Myocardial Infarction," The New England Journal of Medicine, vol. 348, No. 14, Apr. 3, 2003, pp. 1309-1321.
B. Pitt et al.: "The Effect of Spironolactone on Morbidity and Mortality in Patients with Severe Heart Failure," The New England Journal of Medicine, vol. 341, No. 10, pp. 709-717.
L. Seiler et al.: "Der Aldosteron-Renin-Quotient bei Sekundarer Hypertonie," Herz, vol. 28, No. 8, 2003, 686-691.
H. A. Kuhn et al.: Innere Medizin—Ein Lehrbuch fur Studierende der Medizin und Arzte Begrundet von Ludwig Heilmeyer,' Springer-Verlag, Berlin, Heidelberg, New York, 1982.
M. A. Zaman et al.; "Drugs Targeting the Renin-Angiotension-Aldosterone System," Nature Reviews Drug Discovery, vol. 1, Aug. 2002, pp. 621-636.
G. Werner et al.: "Hydrophobic Properties of Novel Dihydronaphthyridine Calcium Antagonists and Biological Activity in Porcine Isolated Cardiac and Vascular Smooth Muscle," Naunyn-Schmiedeberg's Archives of Pharmacology vol. 344, 1991, pp. 337-344.
Barabanov, et al.:"Functionalized Naphtho [2,3-h] quinoline-7,12-diones," Russian Chemical Bulletin, Nov. 1998, 47(11):2256-2261.
Funder, "Mineralcorticoid Receptors and Cardiovascular Damage: It's Not Just Aldosterone," Hypertension, 2006, 47:634-635.
Hayashi, et al.:"Immediate Administration of Mineralocorticoid Receptor Antagonist Spironolactone Prevents Post-Infarct Left Ventricular Remodeling Associated With Suppression of a Marker of Myocardial Collagen Synthesis in Patients With First Anterior Acute Myocardial Infarction," Circulation, May 2003, 107(20):2559-2565.
Hinschberger, et al.:"1,2,3,4,5,6-Hexahydrobenzo[h][1,6]naphthyridin-5-ones: 5-HT7 Receptor Affinity," Pharm. Pharmacol. Commun., 2000, 6:67-71.
Kleinschroth, et al.:" Synthese Neur 1,6-Naphthyridine durch Aminomethin-ylierung von 1,4-Dihydropyridinen," Synthesis, Oct. 1986, pp. 859-860.
Kock, et al.:"A New Synthetic Approach to the Benzo[c]phenanthridine Ring System," Synthesis, 2005, 7:1052-1054.
McNamara, et al.:"Synthesis and antitumor activity of fluorine-substituted 4-amino-2(1H)-pyridinones and their nucleosides. 3-Deazacytosines," J. Med. Chem., 1987, 30:340-347.
Nesnow, et al.:"Pyridine Nucleosides Related to 5-Fluorocytosine," J. Heterocycl. Chem., 1975, 12:941-944.
Pietzonka, et al.:"Alkylations of (R,R)-2-t-Butyl-6-methyl-1,3-dioxan-4-ones which are not Possible with Lithium Amides may be Achieved with a Schwesinger P4 Base," Chemische Berichte, Jan. 25, 2006, 124(8):1837-1843.

(Continued)

*Primary Examiner* — Niloofar Rahmani
(74) *Attorney, Agent, or Firm* — Karen B. King; Thomas C. Blankinship

(57) ABSTRACT

The present application relates to novel substituted 4-aryl-1,4-dihydro-1,6-naphthyridines, a process for their preparation, their use for the treatment and/or prophylaxis of diseases, and their use for the manufacture of medicaments for the treatment and/or prophylaxis of diseases, especially cardiovascular disorders.

5 Claims, No Drawings

OTHER PUBLICATIONS

Pitt, et al.:"The Effect of Spironalactone on Morbidity and Mortality in Patients with Severe Heart Failure," The New England Journal of Medicine, Sep. 2, 1999, 341(10):709-717.

Pitt, et al.:"Neurohumoral Effects of Aliskiren in Patients with Symptomatic Heart Failure Receiving a Mineralocorticoid Receptor Antagonist: The Aliskiren Observation of Heart FailureTreatment study," European Journal of Heart Failure, 2011, 13(7): 755-764.

Robl, et al.:"Synthesis of 2-(4-Fluorophenyl)-4-isopropyl-3-quinolinecarbaldehyde: A New Route to 2,3,4-Substituted Quinolines," Synthesis, Jan. 1991, 1:56-58.

Rocha, et al.:"Rationale for the Use of Aldosterone Antagonists in Congestive Heart Failure," Drugs, 2002, 62 (5):723-731.

Schmidt, et al.:"Cardioprotective Effects of Mineralocorticoid Receptor Antagonists at Reperfusion," European Heart Journam, 2010, 31:1655-1662.

Schwesinger, et al.:"Peralkylated Polyaminophosphazenes—Extremely Strong, Neutral Nitrogen Bases," Angewandte Chemie International Edition in English, Dec. 22, 2003, 26(11):1167-1169.

Searls, et al.:"Synthesis of the Analogue Nucleoside 3-Deaza-2'-Deoxycytidine and its Template Activity with DNA Polymerase," Tetrahedron, 1999, 55:11985-11996.

Takeda:"Pleiotropic Actions of Aldosterone and the Effects of Eplerenone, a Selective Mineralocorticoid Receptor Antagonist," Hypertens. Res., 2004, 27(11):781-789.

Weihong, "Sterioid Receptor Heterodimerization Demonstrated in vitro and in vivo," Proc Natl. Acad. Sci USA, Dec. 1995, 92:12480-12484.

West, Anthony R.:"Solid State Chemistry and its Applications," Wiley, New York, 1988, pp. 358 & 365.

Zannad, et al.:"Effect of MR Blockade on Collagen Formation and Cardiovascular Disease with a Specific Emphasis on Heart Failure," Heart Failure Reviews, 2005, 10:71-78.

U.S. Appl. No. 12/303,369, filed Aug. 7, 2009.

U.S. Appl. No. 12/526,951, filed.

* cited by examiner

SUBSTITUTED 4-ARYL-1,4-DIHYDRO-1,6-NAPHTHYRIDINES AND USE THEREOF

RELATED APPLICATIONS/PATENTS AND INCORPORATION BY REFERENCE

This application is a National Stage Application filed under 35 U.S.C. §371 based on International Application No. PCT/EP2007/004865, filed Jun. 1, 2007, which claims priority to German Patent Application Number 102006026585.8, filed Jun. 7, 2006, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present application relates to novel substituted 4-aryl-1,4-dihydro-1,6-naphthyridines, a process for their preparation, their use for the treatment and/or prophylaxis of diseases, and their use for the manufacture of medicaments for the treatment and/or prophylaxis of diseases, especially cardiovascular disorders.

Aldosterone plays a key part in maintaining fluid and electrolyte homeostasis by promoting, in the epithelium of the distal nephron, sodium retention and potassium secretion, thus contributing to keeping the extracellular volume constant and thus to regulating blood pressure. Besides this, aldosterone displays direct effects on the structure and function of the cardiac and vascular system, but the underlying mechanisms thereof are not yet fully explained [R. E. Booth, J. P. Johnson, J. D. Stockand, *Adv. Physiol. Educ.* 26 (1), 8-20 (2002)].

Aldosterone is a steroid hormone which is formed in the adrenal cortex. Its production is regulated indirectly very substantially depending on the renal blood flow. Any decrease in renal blood flow leads to release in the kidney of the enzyme renin into the circulating blood. This in turn activates the formation of angiotensin II, which on the one hand has a constricting effect on the arterial blood vessels, but on the other hand also stimulates the formation of aldosterone in the adrenal cortex. Thus, the kidney acts as blood pressure sensor, and thus indirect volume sensor, in the circulating blood and counteracts, via the renin-angiotensin-aldosterone system, critical losses of volume by on the one hand increasing the blood pressure (angiotensin II effect), and on the other hand, by rebalancing the state of filling of the vascular system by increased reabsorption of sodium and water in the kidney (aldosterone effect).

This control system may be pathologically impaired in diverse ways. Thus, a chronic reduction in renal blood flow (e.g. as a result of heart failure and the congestion of blood in the venous system caused thereby) leads to a chronically excessive release of aldosterone. In turn this is followed by an expansion of the blood volume and thereby increases the weakness of the heart through an excessive supply of volume to the heart. Congestion of blood in the lungs with shortness of breath and formation of edema in the extremities, and ascites and pleural effusions may be the result; the renal blood flow falls further. In addition, the excessive aldosterone effect leads to a reduction in the potassium concentration in the blood and in the extracellular fluid. In heart muscles which have been previously damaged otherwise, cardiac arrhythmias with a fatal outcome may be induced if there is a deviation below a critical minimum level. This is likely to be one of the main causes of the sudden cardiac death which frequently occurs in patients with heart failure.

In addition, aldosterone is also thought to be responsible for a number of the myocardial remodeling processes typically to be observed in heart failure. Thus, hyperaldosteronism is a crucial component in the pathogenesis and prognosis of heart failure which may originally be induced by various types of damage such as, for example, a myocardial infarction, a myocardial inflammation or high blood pressure. This assumption is supported by the fact that there was a marked reduction in overall mortality in wide-ranging clinical studies on groups of patients with chronic heart failure and post acute myocardial infarction through the use of aldosterone antagonists [B. Pitt, F. Zannad, W. J. Remme et al., *N. Engl. J. Med.* 341, 709-717 (1999); B. Pitt, W. Remme, F. Zannad et al., *N. Engl. J. Med.* 348, 1309-1321 (2003)]. It was possible to achieve this inter alia by reducing the incidence of sudden cardiac death.

According to recent studies, a not inconsiderable number of patients suffering from essential hypertension are also found to have a so-called normokalemic variant of primary hyperaldosteronism [prevalence up to 11% of all hypertensives: L. Seiler and M. Reincke, *Der Aldosteron-Renin-Quotient bei sekundärer Hypertonie*, Herz 28, 686-691 (2003)]. The best diagnostic method for normokalemic hyperaldosteronism is the aldosterone/renin quotient of the corresponding plasma concentrations, so that relative elevations in aldosterone in relation to the renin plasma concentrations can also be diagnosed and eventually treated. For this reason, a hyperaldosteronism diagnosed in connection with essential hypertension is a starting point for a causal and prophylactically worthwhile therapy.

Far less common than the types of hyperaldosteronism detailed above are pathological states in which the impairment either is to be found in the hormone-producing cells of the adrenal itself, or the number or mass thereof is increased through hyperplasia or proliferation. Adenomas or diffuse hyperplasias of the adrenal cortex are the commonest cause of the primary hyperaldosteronism referred to as Conn's syndrome, the leading symptoms of which are hypertension and hypokalemic alkalosis. The priority here too, besides surgical removal of the diseased tissue, is medical therapy with aldosterone antagonists [H. A. Kühn and J. Schirmeister (Editors), *Innere Medizin*, 4th edition, Springer Verlag, Berlin, 1982].

Another pathological state associated typically with an elevation of the plasma aldosterone concentration is advanced cirrhosis of the liver. The cause of the aldosterone elevation in this case is mainly the restricted aldosterone breakdown resulting from the impairment of liver function. Volume overload, edema and hypokalemia are the typical consequences, which can be successfully alleviated in clinical practice by aldosterone antagonists.

The effects of aldosterone are mediated by the mineralocorticoid receptor which has an intracellular location in the target cells. The aldosterone antagonists available to date have, like aldosterone itself, a basic steroid structure. The utility of such steroidal antagonists is limited by their interactions with the receptors of other steroid hormones, which in some cases lead to considerable side effects such as gynecomastia and impotence and to discontinuation of the therapy [M. A. Zaman, S. Oparil, D. A. Calhoun, *Nature Rev. Drug Disc.* 1, 621-636 (2002)].

The use of potent, non-steroidal antagonists which are more selective for the mineralocorticoid receptor provides the possibility of avoiding this profile of side effects and thus achieving a distinct therapeutic advantage.

The object of the present invention is to provide novel compounds which can be used as selective mineralocorticoid receptor antagonists for the treatment of disorders, especially cardiovascular disorders.

EP 0 133 530-A, EP 0 173 933-A, EP 0 189 898-A and EP 0 234 516-A disclose 4-aryl-substituted 1,4-dihydro-1,6-naphthyridines and -naphthyridinones having a calcium-antagonistic effect for the treatment of vascular disorders. The pharmacological profile of these compounds is reported inter alia in G. Werner et al., *Naunyn-Schmiedeberg's Arch. Pharmacol.* 344 (3), 337-344 (1991). In addition, 1,4-dihydro-1,6-naphthyridine derivatives are claimed in WO 02/10164 as potassium channel openers for the treatment of various, in particular urological, disorders. 4-Fluorenonyl- and 4-chromenonyl-1,4-dihydropyridine derivatives are described as mineralocorticoid receptor antagonists in WO 2005/087740 and WO 2007/009670. WO 2006/066011 discloses 4-aryl-3-cyano-1,4-dihydropyridine-5-carboxylic esters and carboxamides as in some cases dual modulators of steroid hormone receptors and of the L-type calcium channel, and WO 2005/097118 claims compounds having a 4-aryl-1,4-dihydropyridine core structure as aldosterone receptor antagonists.

The present invention relates to compounds of the general formula (I)

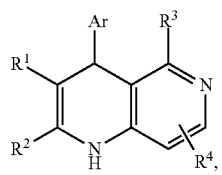

in which
Ar is a group of the formula

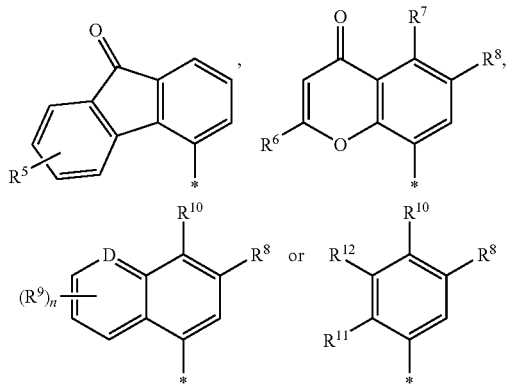

in which
* is the linkage point,
$R^5$ is hydrogen or halogen,
$R^6$ is methyl or ethyl,
$R^7$ is hydrogen, fluorine, chlorine, cyano, nitro, trifluoromethyl or $(C_1-C_4)$-alkyl,
$R^8$ is hydrogen or fluorine,
$R^9$ is halogen, $(C_1-C_4)$-alkyl, trifluoromethyl, $(C_1-C_4)$-alkoxy or trifluoromethoxy,
$R^{10}$ is cyano or nitro,
$R^{11}$ is hydrogen, halogen, $(C_1-C_4)$-alkyl, $(C_1-C_4)$-alkoxy, $(C_1-C_4)$-alkylthio or di-$(C_1-C_4)$-alkylamino, it being possible for the alkyl group in said $(C_1-C_4)$-alkyl, $(C_1-C_4)$-alkoxy and $(C_1-C_4)$-alkylthio radicals in each case to be substituted up to three times by fluorine,
or
phenyl, which may be substituted by halogen, $(C_1-C_4)$-alkyl or trifluoromethyl,
$R^{12}$ is hydrogen, halogen or $(C_1-C_4)$-alkyl,
D is CH, C—$R^9$ or N,
and
n is the number 0, 1 or 2,
it being possible in the case where the substituent $R^9$ occurs more than once for its meanings to be identical or different,
$R^1$ is cyano, nitro or a group of the formula —C(=O)—$R^{13}$
in which
$R^{13}$ is $(C_1-C_6)$-alkyl which may be substituted by $(C_3-C_7)$-cycloalkyl or once to three times by fluorine, or phenyl which may be substituted by halogen, cyano, $(C_1-C_4)$-alkyl, trifluoromethyl, $(C_1-C_4)$-alkoxy or trifluoromethoxy, or $(C_3-C_7)$-cycloalkyl,
$R^2$ is $(C_1-C_4)$-alkyl, trifluoromethyl, cyclopropyl, cyclobutyl, $(C_1-C_4)$-alkoxy or $(C_1-C_4)$-alkylthio,
$R^3$ is $(C_1-C_6)$-alkyl, $(C_1-C_6)$-alkoxy, trifluoromethoxy, $(C_1-C_6)$-alkylthio, amino, mono-$(C_1-C_6)$-alkylamino or a group of the formula —O—$SO_2$—$R^{14}$,
where said $(C_1-C_6)$-alkyl, $(C_1-C_6)$-alkoxy and $(C_1-C_6)$-alkylthio radicals may in each case be substituted by $(C_3-C_7)$-cycloalkyl,
and
$R^{14}$ is $(C_1-C_6)$-alkyl, trifluoromethyl, $(C_3-C_7)$-cycloalkyl, phenyl or 5- or 6-membered heteroaryl having up to two heteroatoms from the series N, O and/or S,
it being possible for phenyl and heteroaryl in turn each to be substituted once or twice, identically or differently, by halogen, cyano, nitro, $(C_1-C_4)$-alkyl, trifluoromethyl, $(C_1-C_4)$-alkoxy and/or trifluoromethoxy,
and
$R^4$ is hydrogen, fluorine, $(C_1-C_4)$-alkyl, trifluoromethyl, $(C_1-C_4)$-alkoxy, trifluoromethoxy, $(C_1-C_4)$-alkylthio, amino, mono-$(C_1-C_4)$-alkylamino or di-$(C_1-C_4)$-alkylamino,
and the salts, solvates and solvates of the salts thereof.

Compounds of the invention are the compounds of the formula (I) and the salts, solvates and solvates of the salts thereof; the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

The compounds of the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

If the compounds of the invention may occur in tautomeric forms, the present invention encompasses all tautomeric forms.

Salts which are preferred for the purposes of the present invention are physiologically acceptable salts of the compounds of the invention. Also encompassed are salts which are themselves unsuitable for pharmaceutical uses but can be used for example for isolating or purifying the compounds of the invention.

Physiologically acceptable salts of the compounds of the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention include salts of conventional bases such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refers for the purposes of the invention to those forms of the compounds of the invention which form, in the solid or liquid state, a complex by coordination with solvent molecules. Hydrates are a specific form of solvates in which the coordination takes place with water. Hydrates are preferred solvates in the context of the present invention.

The present invention additionally encompasses prodrugs of the compounds of the invention. The term "prodrugs" encompasses compounds which themselves may be biologically active or inactive, but are converted during their residence time in the body into compounds of the invention (for example by metabolism or hydrolysis).

In the context of the present invention, the substituents have the following meaning, unless specified otherwise:

$(C_1-C_6)$-Alkyl, $(C_1-C_4)$-alkyl and $(C_1-C_3)$-alkyl represent in the context of the invention a straight-chain or branched alkyl radical having respectively 1 to 6, 1 to 4 and 1 to 3 carbon atoms. A straight-chain or branched alkyl radical having 1 to 4, particularly preferably having 1 to 3, carbon atoms is preferred. Mention may be made by way of example and preferably of: methyl, ethyl, n-propyl, isopropyl, n-butyl, iso-butyl, sec-butyl, tert-butyl, 1-ethylpropyl, n-pentyl, isopentyl and n-hexyl.

$(C_3-C_7)$-Cycloalkyl and $(C_3-C_6)$-cycloalkyl represent in the context of the invention a saturated monocyclic cycloalkyl group having respectively 3 to 7 and 3 to 6 carbon atoms. Preference is given to a cycloalkyl radical having 3 to 6 carbon atoms. Mention may be made by way of example and preferably of: cyclopropyl, cyclobutyl, cyclopentyl, cyclohexyl and cycloheptyl.

$(C_1-C_6)$-Alkoxy, $(C_1-C_4)$-alkoxy and $(C_1-C_3)$-alkoxy represent in the context of the invention a straight-chain or branched alkoxy radical having respectively 1 to 6, 1 to 4 and 1 to 3 carbon atoms. A straight-chain or branched alkoxy radical having 1 to 4, particularly preferably having 1 to 3, carbon atoms is preferred. Mention may be made by way of example and preferably of: methoxy, ethoxy, n-propoxy, isopropoxy, n-butoxy, tert-butoxy, n-pentoxy and n-hexoxy.

$(C_1-C_6)$-Alkylthio and $(C_1-C_4)$-alkylthio represent in the context of the invention a straight-chain or branched alkylthio radical having respectively 1 to 6 and 1 to 4 carbon atoms. A straight-chain or branched alkylthio radical having 1 to 4 carbon atoms is preferred. Mention may be made by way of example and preferably of: methylthio, ethylthio, n-propylthio, isopropylthio, n-butylthio, tert-butylthio, n-pentylthio and n-hexylthio.

Mono-$(C_1-C_6)$-alkylamino and mono-$(C_1-C_4)$-alkylamino represent in the context of the invention an amino group having one straight-chain or branched alkyl substituent which has respectively 1 to 6 and 1 to 4 carbon atoms. A straight-chain or branched monoalkylamino radical having 1 to 4 carbon atoms is preferred. Mention may be made by way of example and preferably of: methylamino, ethylamino, n-propylamino, isopropylamino, n-butylamino, tert-butylamino, n-pentylamino and n-hexylamino.

Di-$(C_1-C_6)$-alkylamino and di-$(C_1-C_4)$-alkylamino represent in the context of the invention an amino group having two identical or different straight-chain or branched alkyl substituents, each of which have respectively 1 to 6 and 1 to 4 carbon atoms. Preference is given to straight-chain or branched dialkylamino radicals each having 1 to 4 carbon atoms. Mention may be made by way of example and preferably of: N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino.

5- or 6-membered heteroaryl represents in the context of the invention an aromatic heterocycle (heteroaromatic) having 5 or 6 ring atoms which comprises one or two ring atoms from the series N, O and/or S and is linked via a ring carbon atom. Mention may be made by way of example and preferably of: furyl, pyrrolyl, thienyl, pyrazolyl, imidazolyl, thiazolyl, oxazolyl, isoxazolyl, isothiazolyl, pyridyl, pyrimidinyl, pyridazinyl and pyrazinyl.

Halogen includes in the context of the invention fluorine, chlorine, bromine and iodine. Fluorine or chlorine are preferred.

If radicals in the compounds of the invention are substituted, the radicals may be substituted one or more times, unless specified otherwise. In the context of the present invention, all radicals which occur more than once have a mutually independent meaning. Substitution by one, two or three identical or different substituents is preferred. Substitution by one substituent is very particularly preferred.

Preference is given to compounds of the formula (I) in which
Ar is a group of the formula

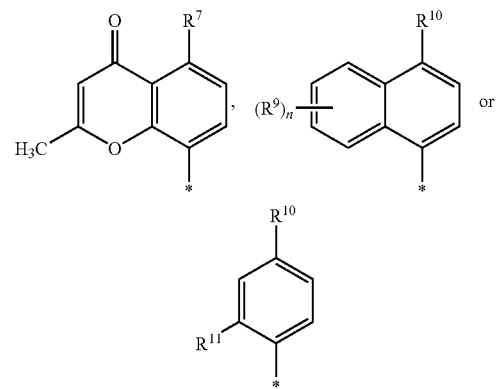

in which
* is the linkage point,
$R^7$ is hydrogen, fluorine, chlorine or cyano,
$R^9$ is fluorine, chlorine, methyl or ethyl, $R^{10}$ is cyano or nitro,
$R^{11}$ is chlorine, bromine, $(C_1-C_4)$-alkyl, trifluoromethyl, $(C_1-C_4)$-alkoxy, trifluoromethoxy, $(C_1-C_4)$-alkylthio or trifluoromethylthio,
and
n is the number 0 or 1,
$R^1$ is cyano, acetyl or trifluoroacetyl,
$R^2$ is methyl or trifluoromethyl,
$R^3$ is $(C_1-C_4)$-alkoxy, trifluoromethoxy or a group of the formula —O—SO$_2$—$R^{14}$ in which
$R^{14}$ is $(C_1-C_4)$-alkyl, trifluoromethyl, $(C_3-C_6)$-cyanoalkyl, phenyl or thienyl,
where phenyl and thienyl in turn may each be substituted once or twice, identically or differently by fluorine, chlorine, cyano, methyl, trifluoromethyl, methoxy and/or trifluoromethoxy,
and
$R^4$ is hydrogen, fluorine or methyl,
and the salts, solvates and solvates of the salts thereof.

Particular preference is given to compounds of the formula (I) in which
Ar is a group of the formula

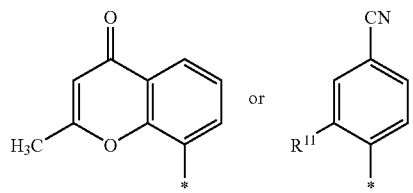

in which
* is the linkage point
and
$R^{11}$ is ethyl, methoxy or trifluoromethoxy,
$R^1$ is cyano or acetyl,
$R^2$ is methyl or trifluoromethyl,
$R^3$ is $(C_1-C_3)$-alkoxy or a group of the formula —O—SO$_2$—$R^{14}$ in which
$R^{14}$ is $(C_1-C_3)$-alkyl,
and
$R^4$ is hydrogen or methyl,
and the salts, solvates and solvates of the salts thereof.

The definitions of radicals indicated specifically in the respective combinations or preferred combinations of radicals are replaced as desired irrespective of the particular combinations indicated for the radicals also by definitions of radicals of other combinations.

Combinations of two or more of the abovementioned preferred ranges are very particularly preferred.

The invention further relates to a process for preparing the compounds of the invention of the formula (I), in which $R^3$ is optionally $(C_3-C_7)$-cycloalkyl-substituted $(C_1-C_6)$-alkoxy, trifluoromethoxy or a group of the formula —O—SO$_2$—$R^{14}$ in which $R^{14}$ has the meaning indicated above characterized in that a compound of the formula (II)

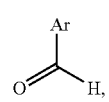

in which Ar has the meaning indicated above, either

[A] is reacted in a one-stage (one-pot reaction) or two-stage process with a compound of the formula (III)

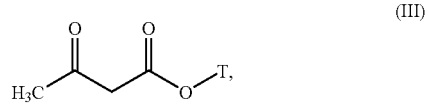

in which
T is methyl or ethyl,
and a compound of the formula (IV)

in which $R^1$ and $R^2$ have the meanings indicated above,
to give a compound of the formula (V)

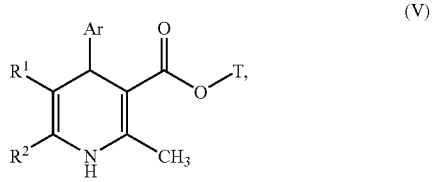

in which Ar, $R^1$, $R^2$ and T each have the meanings indicated above, and the latter is then reacted in an inert solvent with s-triazine in the presence of a base to give a compound of the formula (VIa)

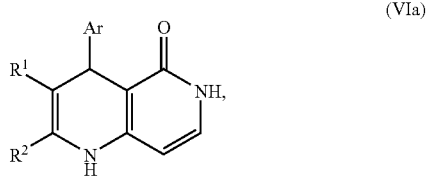

in which Ar, $R^1$ and $R^2$ each have the meanings indicated above, or

[B] is reacted in a one-stage (one-pot reaction) or two-stage process with a compound of the formula (VII)

in which $R^1$ and $R^2$ have the meanings indicated above, and a compound of the formula (VIII)

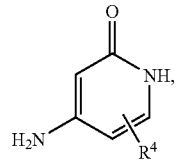
(VIII)

in which R⁴ has the meaning indicated above,
to give a compound of the formula (VI)

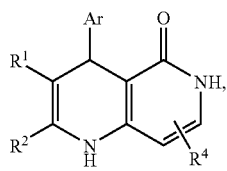
(VI)

in which Ar, R¹, R² and R⁴ each have the meanings indicated above, and then the compounds of the formula (VIa) or (VI) are alkylated in an inert solvent, where appropriate in the presence of a base, with a compound of the formula (IX) or a trialkyloxonium salt of the formula (X)

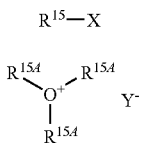

(IX)

(X)

in which

R¹⁵ is $(C_1-C_6)$-alkyl which may be substituted by $(C_3-C_7)$-cycloalkyl or is trifluoromethyl, $R^{15A}$ is methyl or ethyl, X is a leaving group such as, for example, halogen, mesylate, tosylate or triflate, and Y⁻ is a non-nucleophilic anion such as, for example, tetrafluoroborate, or in the presence of an acid with an orthoformic ester of the formula (XI)

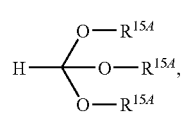
(XI)

in which $R^{15A}$ has the meaning indicated above, to give compounds of the formula (I-A)

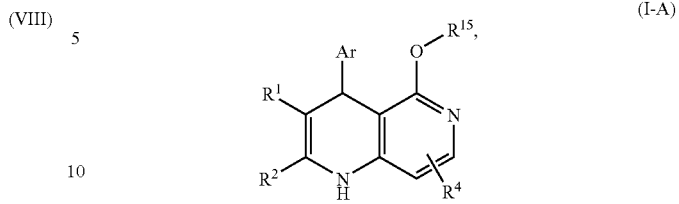
(I-A)

in which Ar, R¹, R², R⁴ and R¹⁵ each have the meanings indicated above, or the compounds of the formula (VIa) or (VI) are reacted in an inert solvent in the presence of a base with a compound of the formula (XII)

(XII)

in which R¹⁴ has the meaning indicated above,
to give compounds of the formula (I-B)

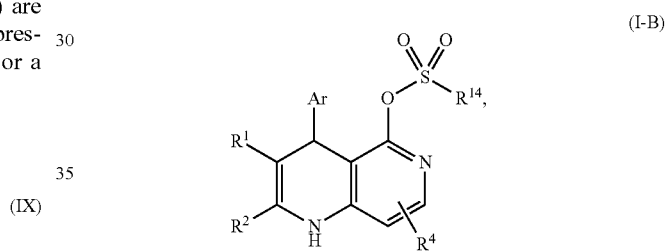
(I-B)

in which Ar, R¹, R², R⁴ and R¹⁴ each have the meanings indicated above, and where appropriate the resulting compounds of the formula (I-A) or (I-B) are separated by methods known to the skilled worker into their enantiomers and/or diastereomers, and/or converted with the appropriate (i) solvents and/or (ii) bases or acids into the solvates, salts and/or solvates of the salts thereof.

Process steps (II)+(III)+(IV)→(V) and (II)+(VII)+(VIII)→(VI) are generally carried out in an inert solvent in a temperature range from +20° C. to the boiling point of the solvent under atmospheric pressure.

Inert solvents suitable for this purpose are for example alcohols such as methanol, ethanol, n-propanol, isopropanol, n-butanol or tert-butanol, halohydrocarbons such as dichloromethane, trichloromethane, tetrachloromethane, trichloroethane or 1,2-dichloroethane, or other solvents such as acetonitrile, tetrahydrofuran, dioxane, 1,2-dimethoxyethane, hexane, benzene, toluene, chlorobenzene, pyridine or glacial acetic acid. The reactions are preferably carried out in dichloromethane, toluene, ethanol or isopropanol at the respective reflux temperature under atmospheric pressure.

Process steps (II)+(III)+(IV)→(V) and (II)+(VII)+(VIII)→(VI) can where appropriate advantageously take place in the presence of an acid, of an acid/base combination and/or of a dehydrating agent such as, for example, molecular sieves. Examples of suitable acids are acetic acid, trifluoroacetic acid, methanesulfonic acid or p-toluenesulfonic acid; suitable bases are in particular piperidine or pyridine [compare reaction scheme 8 hereinafter; for the synthesis of 1,4-dihydropyridines, compare also D. M. Stout, A. I. Meyers, *Chem. Rev.* 1982, 82, 223-243; H. Meier et al., *Liebigs Ann. Chem.* 1977, 1888; H. Meier et al., ibid. 1977, 1895; H. Meier et al., ibid. 1976, 1762; F. Bossert et al., *Angew. Chem.* 1981, 93, 755].

The reaction with s-triazine in process step (V)→(VIa) is preferably carried out in N,N-dimethylformamide using sodium hydride as base [cf. J. Kleinschroth et al., *Synthesis* 1986, 859-860].

It is possible where appropriate for separation of the enantiomers and/or diastereomers to take place even at the stage of the intermediates (VIa) and (VI), which are then subjected separately to the subsequent reactions (cf. reaction scheme 9).

Inert solvents for process steps (VI)+(IX)→(I-A), (VI)+(X)→(I-A) and (VI)+(XII)→(I-B) are for example ethers such as diethyl ether, methyl tert-butyl ether, dioxane, tetrahydrofuran, glycol dimethyl ether or diethylene glycol dimethyl ether, hydrocarbons such as benzene, toluene, xylene, hexane, cyclohexane or petroleum fractions, halohydrocarbons such as dichloromethane, trichloromethane, tetrachloromethane, 1,2-dichloroethane, trichloroethane, tetrachloroethane, trichloroethylene, chlorobenzene or chlorotoluene, or other solvents such as N,N-dimethylformamide (DMF), dimethyl sulfoxide (DMSO), N,N'-dimethylpropyleneurea (DMPU), N-methylpyrrolidone (NMP), pyridine or acetonitrile. It is likewise possible to use mixtures of said solvents. Preference is given to the use of tetrahydrofuran or dimethylformamide in process step (VI)+(IX)→(I-A), of dichloromethane in process step (VI)+(X) (I-A), and of pyridine in process step (VI)+(XII)→(I-B).

Process variant (VI)+(XI)→(I-A) is preferably carried out with a large excess of orthoformic ester without addition of a further solvent; strong inorganic acids such as sulfuric acid for example are advantageous as reaction catalyst [compare for example I. I. Barabanov et al., *Russ. Chem. Bl.* 47 (11), 2256-2261 (1998)].

Bases suitable for process step (VI)+(IX)→(I-A) are in particular alkali metal or alkaline earth metal carbonates such as lithium, sodium, potassium, calcium or cesium carbonate, alkali metal hydrides such as sodium or potassium hydride, amides such as lithium, sodium or potassium bis(trimethylsilyl)amide or lithium diisopropylamide, organometallic compounds such as butyllithium or phenyllithium, or else phosphazene bases such as, for example, P2-t-Bu or P4-t-Bu [so-called "Schwesinger bases", compare R. Schwesinger, H. Schlemper, *Angew. Chem. Int. Ed. Engl.* 26, 1167 (1987); T. Pietzonka, D. Seebach, *Chem. Ber.* 124, 1837 (1991)]. Sodium hydride or the phosphazene base P4-t-Bu is preferably used.

Bases suitable for process step (VI)+(XII)→(I-B) are in particular alkali metal or alkaline earth metal carbonates such as lithium, sodium, potassium, calcium or cesium carbonate, alkali metal hydrides such as sodium or potassium hydride, organometallic compounds such as butyllithium or phenyllithium, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo-[5.4.0]undec-7-ene (DBU) or 1,4-diazabicyclo[2.2.2]octane (DABCO®). Pyridine is preferably used and simultaneously also serves as solvent.

Process step (VI)+(X)→(I-A) is generally carried out without addition of a base.

The reactions (VI)+(IX)→(I-A), (VI)+(X)→(I-A) and (VI)+(XII)→(I-B) generally take place in a temperature range from −20° C. to +100° C., preferably at 0° C. to +60° C.; process variant (VI)+(XI)→(I-A) is ordinarily carried out in a temperature range from +100° C. to +150° C. The reactions can be carried out under atmospheric, elevated or reduced pressure (e.g. from 0.5 to 5 bar); they are generally carried out under atmospheric pressure.

The compounds of the formula (II) are commercially available, known from the literature or can be prepared in analogy to processes known from the literature (compare reaction schemes 1-7 hereinafter). The compounds of the formulae (III), (IV), (VII), (IX), (X), (XI) and (XII) are in many cases commercially available, known from the literature or can be prepared by methods known from the literature.

The compounds of the formula (VIII) are described in the literature or can be obtained in analogy to processes known from the literature [compare for example T. Searls, L. W. McLaughlin, *Tetrahedron* 55, 11985-11996 (1999); D. McNamara, P. D. Cook, *J. Med. Chem.* 30, 340-347 (1987); S. Nesnow, C. Heidelberger, *J. Heterocycl. Chem.* 12, 941-944 (1975); N. C. Hung, E. Bisagni, *Synthesis* 1984, 765-766].

The compounds of the invention of the formula (I) in which $R^3$ is $(C_1-C_6)$-alkyl or mono-$(C_1-C_6)$-alkylamino can be obtained in analogy to methods known from the literature, for example starting from compounds of the formula (I-B) in which $R^{14}$ is trifluoromethyl (see reaction scheme 10).

The compounds of the invention of the formula (I) in which $R^3$ is $(C_1-C_6)$-alkylthio can be obtained in analogy to methods known from the literature, for example starting from compounds of the formula (VI) (see reaction scheme 11).

Preparation of the compounds of the invention can be illustrated by the following synthesis schemes:

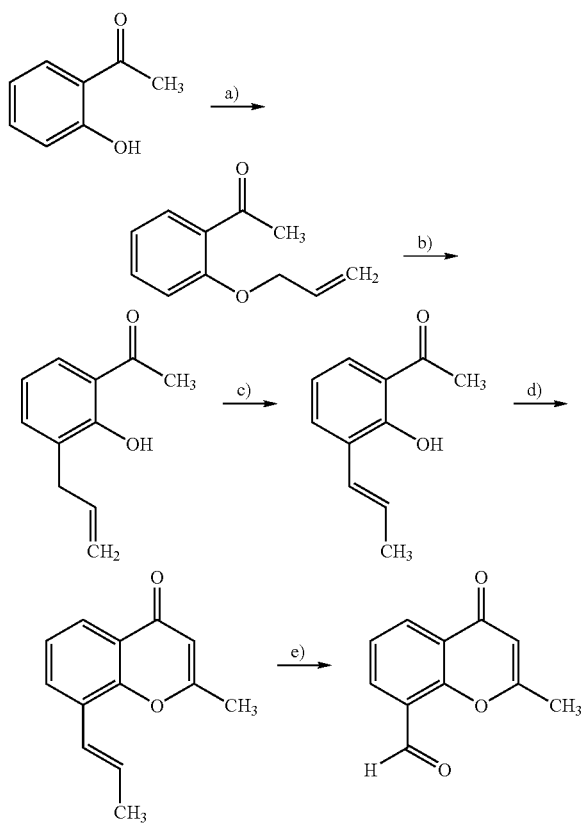

Scheme 1

[a]: allyl bromide, potassium carbonate, cat. potassium iodide, acetone, reflux; b): 230° C., 4 h; c): bis(benzonitrile) dichloropalladium(II), toluene, 120° C., 16 h; d): acetyl chloride, sodium hydride, THF, 10-25° C., 16 h; e): 1. ozone, dichloromethane, −60° C., 30 min; 2. dimethyl sulfide].

Scheme 2

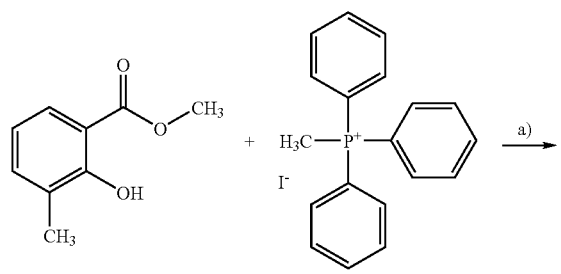

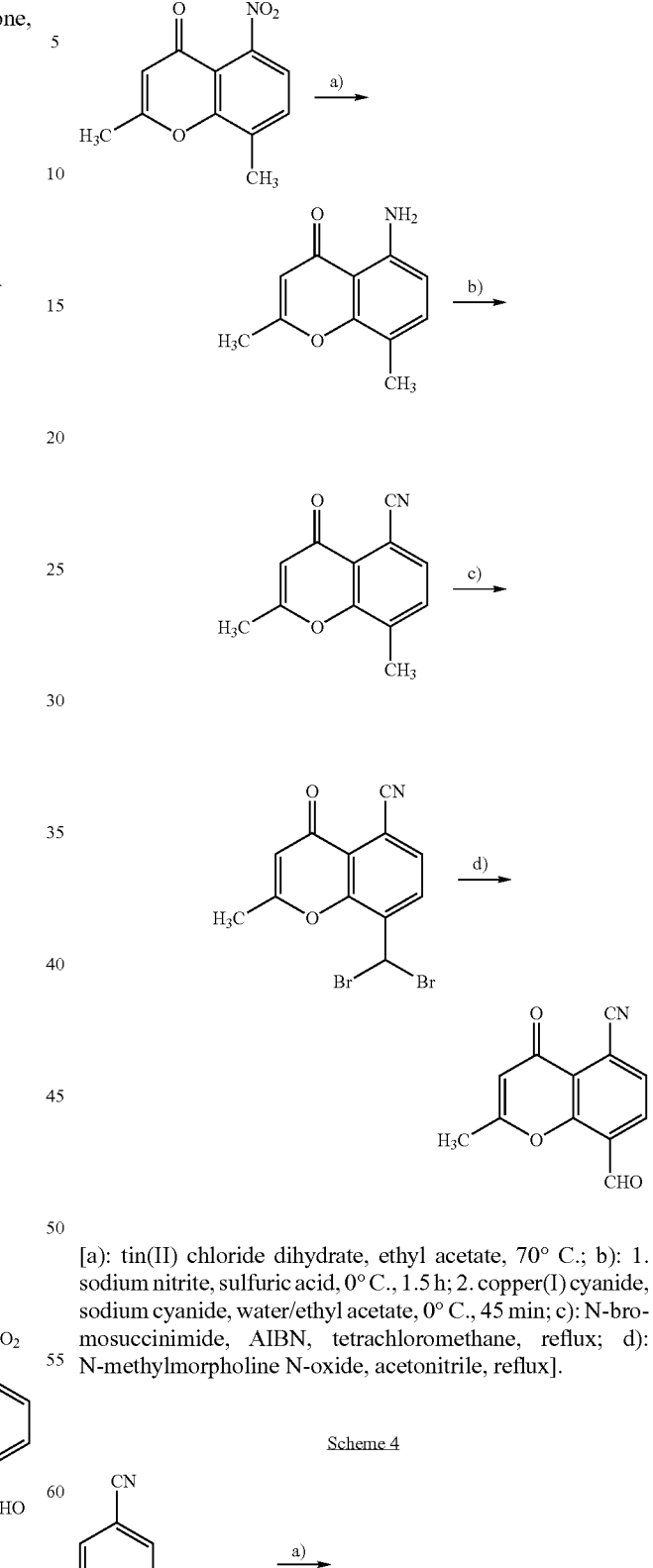

[a]: n-butyllithium, THF, 60° C., 3 h; b): acetic anhydride, pyridine, reflux, 6 h; c): conc. H$_2$SO$_4$, HNO$_3$, 0° C., 1 h; d): N-bromosuccinimide, AIBN, tetrachloromethane, reflux; e): N-methylmorpholine N-oxide, acetonitrile, reflux].

[a]: tin(II) chloride dihydrate, ethyl acetate, 70° C.; b): 1. sodium nitrite, sulfuric acid, 0° C., 1.5 h; 2. copper(I) cyanide, sodium cyanide, water/ethyl acetate, 0° C., 45 min; c): N-bromosuccinimide, AIBN, tetrachloromethane, reflux; d): N-methylmorpholine N-oxide, acetonitrile, reflux].

Scheme 4

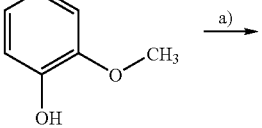

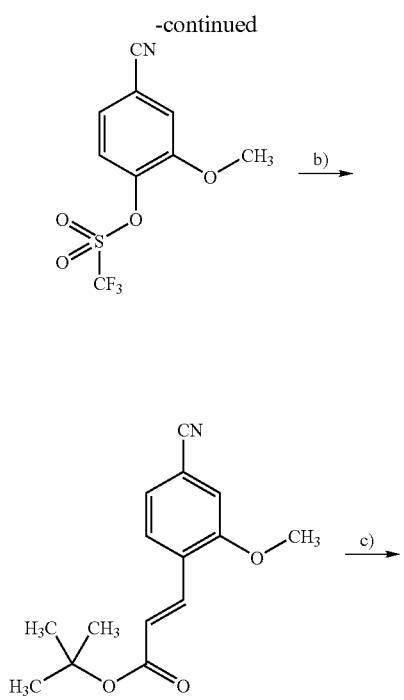

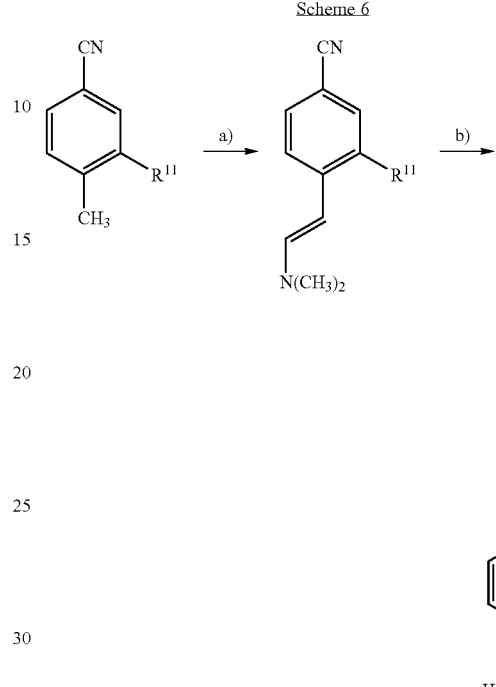

[a]: n-butyllithium, THF, −78° C., then N-formylmorpholine; b): zinc cyanide, tetrakis(triphenylphosphine)palladium(0), DMF, microwave 250° C./5 min].

Scheme 6

[a]: trifluoromethanesulfonic anhydride, pyridine, 0° C.→RT, 30 min; b): tert-butyl acrylate, bis(triphenylphosphine)dichloropalladium(II), DMF, 120° C., 24 h; c): cat. osmium tetroxide, cat. benzyltriethylammonium chloride, sodium periodate, THF/water, 20-25° C., 2 h].

[a]: N,N-dimethylformamide dimethyl acetal, DMF, 140-180° C.; b): sodium periodate, THF/water].

Scheme 7

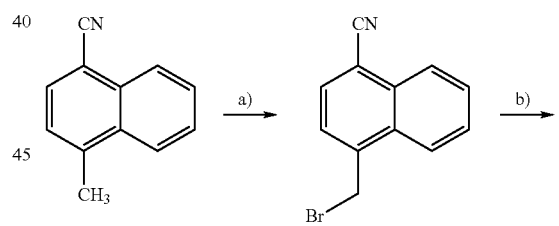

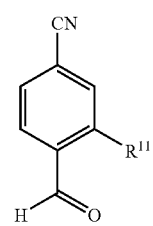

Scheme 5

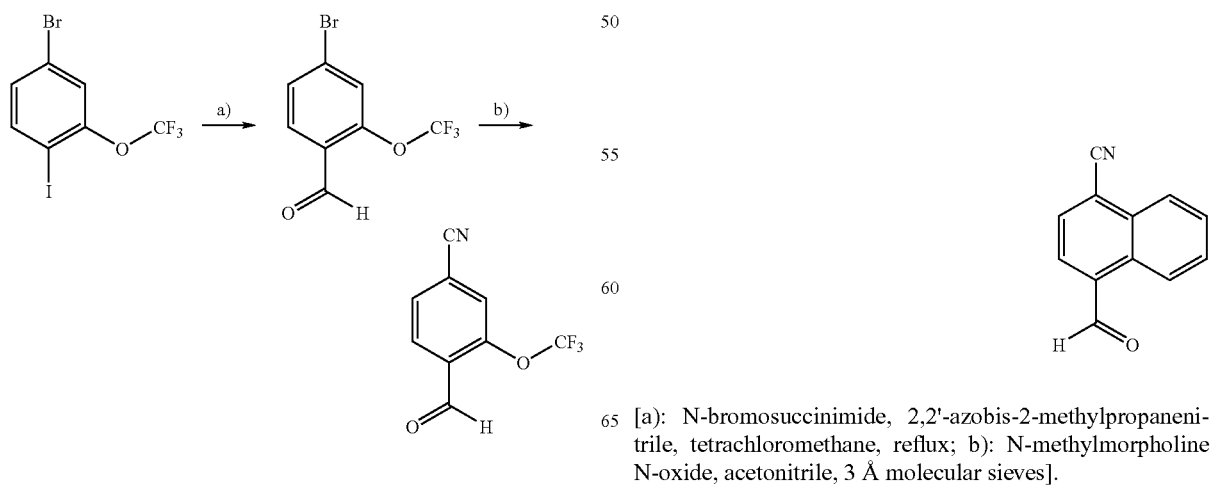

[a]: N-bromosuccinimide, 2,2'-azobis-2-methylpropanenitrile, tetrachloromethane, reflux; b): N-methylmorpholine N-oxide, acetonitrile, 3 Å molecular sieves].

Scheme 8

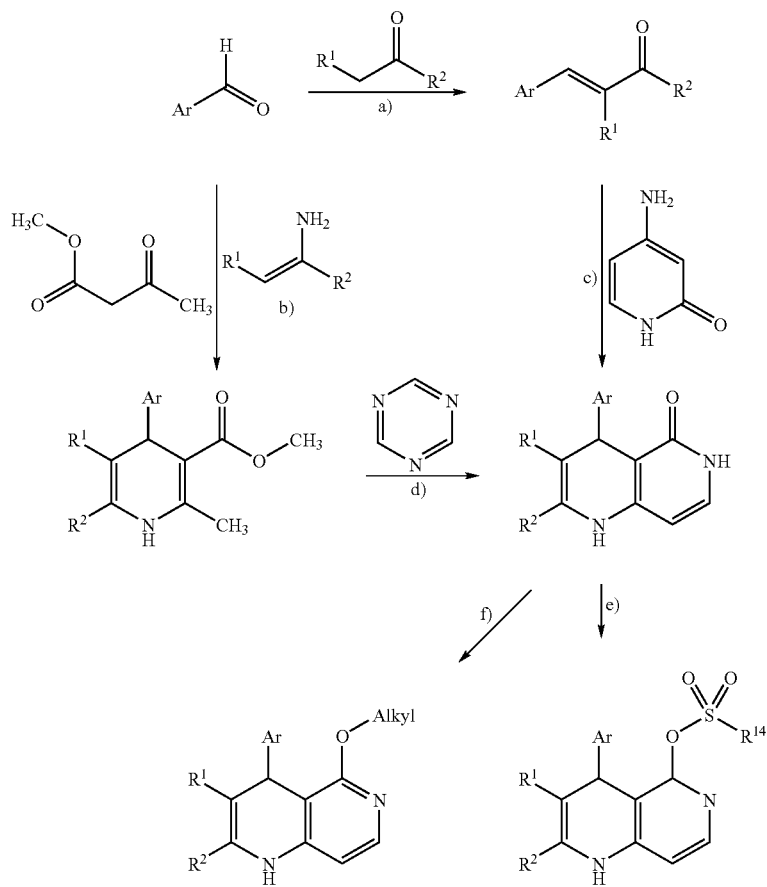

[a]: cat. piperidine, acetic acid, dichloromethane, reflux, 24 h; b): acetic acid, isopropanol, reflux, 12 h; c): isopropanol, reflux, 4 d; d): sodium hydride, DMF, 100° C., 12 h; e): $R^{14}$—$SO_2$—Cl, pyridine, RT, 1-3 h; f): alkyl triflate, phosphazene P4 base, THF, RT, 10 min; or alkyl iodide, sodium hydride, DMF, RT, 10 h; or trialkyloxonium tetrafluoroborate, dichloromethane, RT, 12 h; or trialkyl orthoformate, cat. sulfuric acid, 100-150° C., 12-36 h].

Scheme 9

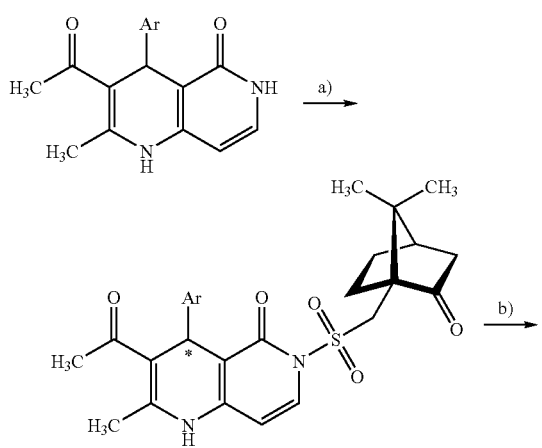

-continued

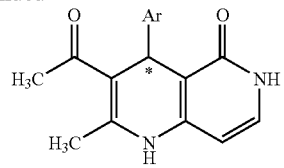

[a]: 1. (1S)-(+)-camphor-10-sulfonyl chloride, lithium tert-butoxide, DMF, RT, 30 min; 2. separation of diastereomers; b): sodium carbonate, methanol/water, RT, 12 h].

Scheme 10

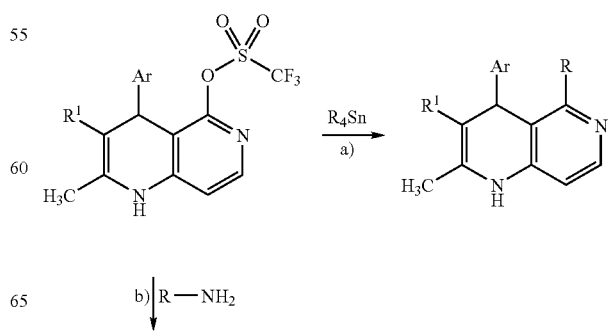

-continued

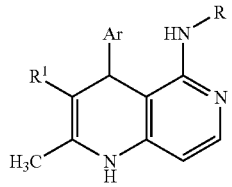

[R=alkyl; a): Pd(PPh₃)₄, LiCl, 2,6-di-tert-butyl-4-methylphenol, dioxane; cf. for example, J. A. Robl, *Synthesis* 1991, 56-58. b): K₂CO₃, DMF; cf. for example, Hinschberger et al., *Pharm. Pharmacol. Commun.* 2000, 6, 67-72].

Scheme 11

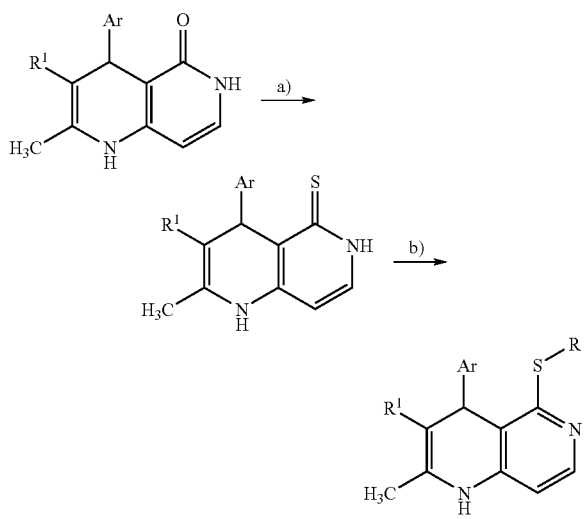

[R=alkyl; a): P₂S₅, pyridine; cf. for example, Kock et al., *Synthesis* 2005, 1052-1054. b): R—I, K₂CO₃, acetone].

The compounds of the invention act as antagonists of the mineralocorticoid receptor and show a valuable range of pharmacological effects which could not have been predicted. They are therefore suitable for use as medicaments for the treatment and/or prophylaxis of diseases in humans and animals.

The compounds of the invention are suitable for the prophylaxis and/or treatment of various disorders and disease-related conditions, especially of disorders which are characterized either by an elevation of the plasma aldosterone concentration or by a change in the plasma aldosterone concentration relative to the plasma rennin concentration, or are associated with these changes. Examples which may be mentioned are: idiopathic primary hyperaldosteronism, hyperaldosteronism associated with adrenal hyperplasia, adrenal adenomas and/or adrenal carcinomas, hyperaldosteronism associated with cirrhosis of the liver, hyperaldosteronism associated with heart failure, and (relative) hyperaldosteronism associated with essential hypertension.

The compounds of the invention are also suitable, because of their mechanism of action, for the prophylaxis of sudden cardiac death in patients at increased risk of dying of sudden cardiac death. These are in particular patients suffering for example from one of the following disorders: hypertension, heart failure, coronary heart disease, stable and unstable angina pectoris, myocardial ischemia, myocardial infarction, dilated cardiomyopathies, shock, arteriosclerosis, atrial and ventricular arrhythmia, transient and ischemic attacks, stroke, inflammatory cardiovascular disorders, peripheral and cardiac vascular disorders, peripheral blood flow disturbances, pulmonary hypertension, spasms of the coronary arteries and peripheral arteries, thromboses, thromboembolic disorders, and vasculitis.

The compounds of the invention can additionally be used for the prophylaxis and/or treatment of edema formation, such as, for example, pulmonary edema, renal edema or heart failure-related edema, and of restenoses such as following thrombolysis therapies, percutaneous transluminal angioplasties (PTA) and transluminal coronary angioplasties (PTCA), heart transplants and bypass operations.

The compounds of the invention are further suitable for use as diuretic and for electrolyte disturbances such as, for example, hypercalcemia.

The compounds of the invention can additionally be employed for the prophylaxis and/or treatment of diabetes mellitus and diabetic sequelae such as, for example, neuropathy and nephropathy, of acute and chronic renal failure and chronic renal insufficiency.

The present invention further relates to the use of the compounds of the invention for the treatment and/or prevention of disorders, especially of the aforementioned disorders.

The present invention further relates to the use of the compounds of the invention for the manufacture of a medicament for the treatment and/or prevention of disorders, especially of the aforementioned disorders.

The present invention further relates to a method for the treatment and/or prevention of disorders, especially of the aforementioned disorders, by using an effective amount of at least one of the compounds of the invention.

The compounds of the invention can be employed alone or, if required, in combination with other active ingredients. The present invention further relates to medicaments comprising at least one of the compounds of the invention and one or more further active ingredients, especially for the treatment and/or prevention of the aforementioned disorders. Suitable active ingredients for combinations are by way of example and preferably:

active ingredients which lower blood pressure, for example and preferably from the group of calcium antagonists, angiotensin AII antagonists, ACE inhibitors, endothelin antagonists, renin inhibitors, alpha-receptor blockers, beta-receptor blockers and Rho kinase inhibitors;

diuretics, especially loop diuretics, and thiazides and thiazide-like diuretics;

agents having an antithrombotic effect, for example and preferably from the group of platelet aggregation inhibitors, of anticoagulants or of profibrinolytic substances;

active ingredients which alter lipid metabolism, for example and preferably from the group of thyroid receptor agonists, cholesterol synthesis inhibitors such as by way of example and preferably HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile adsorbents, bile acid reabsorption inhibitors and lipoprotein(a) antagonists;

organic nitrates and NO donors such as, for example, sodium nitroprusside, nitroglycerin, isosorbide mononitrate, isosorbide dinitrate, molsidomine or SIN-1, and inhaled NO;

compounds having a positive inotropic effect, such as, for example, cardiac glycosides (digoxin), beta-adrenergic and dopaminergic agonists such as isoproterenol, adrenaline, noradrenaline, dopamine and dobutamine;

compounds which inhibit the degradation of cyclic guanosine monophosphate (cGMP) and/or cyclic adenosine monophosphate (cAMP), such as, for example, inhibitors of phosphodiesterases (PDE) 1, 2, 3, 4 and/or 5, especially PDE 5 inhibitors such as sildenafil, vardenafil and tadalafil, and PDE 3 inhibitors such as aminone and milrinone;

natriuretic peptides such as, for example, atrial natriuretic peptide (ANP, anaritide), B-type natriuretic peptide or brain natriuretic peptide (BNP, nesiritide), C-type natriuretic peptide (CNP) and urodilatin;

calcium sensitizers such as by way of example and preferably levosimendan;

potassium supplements;

NO-independent but heme-dependent stimulators of guanylate cyclase such as in particular the compounds described in WO 00/06568, WO 00/06569, WO 02/42301 and WO 03/095451;

NO- and heme-independent activators of guanylate cyclase, such as in particular the compounds described in WO 01/19355, WO 01/19776, WO 01/19778, WO 01/19780, WO 02/070462 and WO 02/070510;

inhibitors of human neutrophil elastase (HNE), such as, for example, sivelestat or DX-890 (reltran);

compounds which inhibit the signal transduction cascade, such as, for example, tyrosine kinase inhibitors, in particular sorafenib, imatinib, gefitinib and erlotinib; and/or compounds which influence the energy metabolism of the heart, such as by way of example and preferably etomoxir, dichloroacetate, ranolazine or trimetazidine.

In a preferred embodiment of the invention, the compounds of the invention are administered in combination with a diuretic such as by way of example and preferably furosemide, bumetanide, torsemide, bendroflumethiazide, chlorthiazide, hydrochlorthiazide, hydroflumethiazide, methyclothiazide, polythiazide, trichlormethiazide, chlorthalidone, indapamide, metolazone, quinethazone, acetazolamide, dichlorophenamide, methazolamide, glycerol, isosorbide, mannitol, amiloride or triamterene.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, Rho kinase inhibitors, and diuretics.

In a preferred embodiment of the invention, the compounds of the invention are administered in combination with a calcium antagonist such as by way of example and preferably nifedipine, amlodipine, verapamil or diltiazem.

In a preferred embodiment of the invention, the compounds of the invention are administered in combination with an angiotensin AII antagonist such as by way of example and preferably losartan, candesartan, valsartan, telmisartan or embusartan.

In a preferred embodiment of the invention, the compounds of the invention are administered in combination with an ACE inhibitor such as by way of example and preferably enalapril, captopril, lisinopril, ramipril, delapril, fosinopril, quinopril, perindopril or trandopril.

In a preferred embodiment of the invention, the compounds of the invention are administered in combination with an endothelin antagonist such as by way of example and preferably bosentan, darusentan, ambrisentan or sitaxsentan.

In a preferred embodiment of the invention, the compounds of the invention are administered in combination with a renin inhibitor such as by way of example and preferably aliskiren, SPP-600 or SPP-800.

In a preferred embodiment of the invention, the compounds of the invention are administered in combination with an alpha-1 receptor blocker such as by way of example and preferably prazosin.

In a preferred embodiment of the invention, the compounds of the invention are administered in combination with a beta-receptor blocker such as by way of example and preferably propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds of the invention are administered in combination with a Rho kinase inhibitor such as by way of example and preferably fasudil, Y-27632, SLx-2119, BF-66851, BF-66852, BF-66853, KI-23095 or BA-1049.

Agents having an antithrombotic effect (antithrombotics) preferably mean compounds from the group of platelet aggregation inhibitors, of anticoagulants or of profibrinolytic substances.

In a preferred embodiment of the invention, the compounds of the invention are administered in combination with a platelet aggregation inhibitor such as by way of example and preferably aspirin, clopidogrel, ticlopidine or dipyridamole.

In a preferred embodiment of the invention, the compounds of the invention are administered in combination with a thrombin inhibitor such as by way of example and preferably ximelagatran, melagatran, bivalirudin or clexane.

In a preferred embodiment of the invention, the compounds of the invention are administered in combination with a GPIIb/IIIa antagonist such as by way of example and preferably tirofiban or abciximab.

In a preferred embodiment of the invention, the compounds of the invention are administered in combination with a factor Xa inhibitor such as by way of example and preferably rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or a low molecular weight (LMW) heparin derivative.

In a preferred embodiment of the invention, the compounds of the invention are administered in combination with a vitamin K antagonist such as by way of example and preferably coumarin.

Agents which alter lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and lipoprotein(a) antagonists.

In a preferred embodiment of the invention, the compounds of the invention are administered in combination with a CETP inhibitor such as by way of example and preferably torcetrapib (CP-529 414), HT-705, BAY 60-5521, BAY 78-7499 or CETP vaccine (Avant).

In a preferred embodiment of the invention, the compounds of the invention are administered in combination with a thyroid receptor agonist such as by way of example and preferably D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins such as by way of example and preferably lovastatin, simvastatin, pravastatin, fluvastatin, atorvastatin, rosuvastatin, cerivastatin or pitavastatin.

In a preferred embodiment of the invention, the compounds of the invention are administered in combination with a squalene synthesis inhibitor such as by way of example and preferably BMS-188494 or TAK-475.

In a preferred embodiment of the invention, the compounds of the invention are administered in combination with an ACAT inhibitor such as by way of example and preferably avasimibe, melinamide, pactimibe, eflucimibe or SMP-797.

In a preferred embodiment of the invention, the compounds of the invention are administered in combination with an MTP inhibitor such as by way of example and preferably implitapide, BMS-201038, R-103757 or JTT-130.

In a preferred embodiment of the invention, the compounds of the invention are administered in combination with a PPAR-gamma agonist such as by way of example and preferably pioglitazone or rosiglitazone.

In a preferred embodiment of the invention, the compounds of the invention are administered in combination with a PPAR-delta agonist such as by way of example and preferably GW-501516 or BAY 68-5042.

In a preferred embodiment of the invention, the compounds of the invention are administered in combination with a cholesterol absorption inhibitor such as by way of example and preferably ezetimibe, tiqueside or pamaqueside.

In a preferred embodiment of the invention, the compounds of the invention are administered in combination with a lipase inhibitor such as by way of example and preferably orlistat.

In a preferred embodiment of the invention, the compounds of the invention are administered in combination with a polymeric bile adsorbent such as by way of example and preferably cholestyramine, colestipol, colesolvam, CholestaGel or colestimide.

In a preferred embodiment of the invention, the compounds of the invention are administered in combination with a bile acid reabsorption inhibitor such as by way of example and preferably ASBT (=IBAT) inhibitors such as, for example, AZD-7806, S-8921, AK-105, BARI-1741, SC-435 or SC-635.

In a preferred embodiment of the invention, the compounds of the invention are administered in combination with a lipoprotein(a) antagonist such as by way of example and preferably gemcabene calcium (CI-1027) or nicotinic acid.

The present invention further relates to medicaments which comprise at least one compound of the invention, normally together with one or more inert, non-toxic, pharmaceutically suitable excipients, and to the use thereof for the aforementioned purposes.

The compounds of the invention may have systemic and/or local effects. For this purpose, they can be administered in a suitable way such as, for example, by the oral, parenteral, pulmonary, nasal, sublingual, lingual, buccal, rectal, dermal, transdermal, conjunctival or otic route or as implant or stent.

The compounds of the invention can be administered in administration forms suitable for these administration routes.

Suitable for oral administration are administration forms which function according to the prior art and deliver the compounds of the invention rapidly and/or in a modified manner, and which contain the compounds of the invention in crystalline and/or amorphized and/or dissolved form, such as, for example, tablets (uncoated and coated tablets, for example having coatings which are resistant to gastric juice or are insoluble or dissolve with a delay and control the release of the compound of the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates or sterile powders.

Suitable for the other routes of administration are, for example, pharmaceutical forms for inhalation (inter alia powder inhalers, nebulizers), nasal drops, solutions, sprays; tablets for lingual, sublingual or buccal administration, films/wafers or capsules, suppositories, preparations for the ears and eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

Oral or parenteral administration are preferred, especially oral administration.

The compounds of the invention can be converted into the stated administration forms. This can take place in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colorings (e.g. inorganic pigments such as, for example, iron oxides) and masking flavors and/or odors.

It has generally proved to be advantageous on parenteral administration to administer amounts of about 0.001 to 1 mg/kg, preferably about 0.01 to 0.5 mg/kg of body weight per day to achieve effective results. On oral administration, the dosage is about 0.01 to 100 mg/kg, preferably about 0.01 to 20 mg/kg, and very particularly preferably about 0.1 to 10 mg/kg of body weight.

It may nevertheless be necessary where appropriate to deviate from the stated amounts, in particular as a function of body weight, administration route, individual response to the active ingredient, type of preparation and time or interval over which administration takes place. Thus, in some cases it may be sufficient to make do with less than the aforementioned minimum amount, whereas in other cases the upper limit mentioned must be exceeded. Where relatively large amounts are administered, it may be advisable to distribute these in a plurality of single doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data of liquid/liquid solutions are based in each case on the volume.

A. Examples Abbreviations and Acronyms abs. absolute
cat. catalytic
CI chemical ionization (in MS)
conc. concentrated
d day(s)
DMF dimethylformamide
DMSO dimethyl sulfoxide
EI electron impact ionization (in MS)
ent enantiomer/enantiopure
eq equivalent(s)
ESI electrospray ionization (in MS)
GC-MS coupled gas chromatography-mass spectrometry
h hour(s)
HPLC high pressure, high performance liquid chromatography
LC-MS coupled liquid chromatography-mass spectrometry
min minute(s)
MS mass spectrometry
NMR nuclear magnetic resonance spectrometry
Ph phenyl
$R_f$ retention index (in TLC)
$R_t$ retention time (in HPLC)
RT room temperature
THF tetrahydrofuran
TLC thin-layer chromatography
v/v volume-to-volume ratio (of a solution)
wt % percent by weight LC-MS, GC-MS and HPLC Methods:

Method 1 (LC-MS):

MS instrument type: Micromass ZQ; HPLC instrument type: Waters Alliance 2795; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 2 (LC-MS):

MS instrument type: Micromass ZQ; HPLC instrument type: HP 1100 Series; UV DAD; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 3 (LC-MS):

Instrument: Micromass Quattro LCZ with HPLC Agilent Series 1100; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Method 4 (LC-MS):

MS instrument type: Micromass ZQ; HPLC instrument type: HP 1100 Series; UV DAD; column: Phenomenex Gemini 3μ 30 mm×3.00 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 5 (LC-MS):

Instrument: Micromass Platform LCZ with HPLC Agilent Series 1100; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 6 (LC-MS):

Instrument: Micromass Platform LCZ with HPLC Agilent Series 1100; column: Thermo HyPURITY Aquastar 3μ 20 mm×2.1 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 7 (GC-MS):

Instrument: Micromass GCT, GC 6890; column: Restek RTX-35MS, 30 m×250 μm×0.25 μm; constant flow with helium: 0.88 ml/min; oven: 60° C.; inlet: 250° C.; gradient: 60° C. (halt for 0.30 min), 50° C./min→120° C., 16° C./min→250° C., 30° C./min→300° C. (halt for 1.7 min).

Method 8 (HPLC):

Instrument: HP 1100 with DAD detection; column: Kromasil 100 RP-18, 60 mm×2.1 mm, 3.5 μm; eluent A: 5 ml of $HClO_4$ (70%)/liter of water, eluent B: acetonitrile; gradient: 0 min 2% B→0.5 min 2% B→4.5 min 90% B→9 min 90% B→9.2 min 2% B→10 min 2% B; flow rate: 0.75 ml/min; column temperature: 30° C.; UV detection: 210 nm.

Method 9 (Chiral HPLC):

Column: 250 mm×46 mm, based on the chiral selector poly(N-methacryloyl-D-leucine tert-butylamide); eluent: isohexane/ethyl acetate 1:1; temperature: 24° C.; flow rate: 2 ml/min; UV detection: 260 nm.

Method 10 (Chiral HPLC):

Column: Daicel Chiralpak AD-H, 5 μm, 250 mm×4 mm; eluent: isohexane/isopropanol 80:20; temperature: 35° C.; flow rate: 2 ml/min; UV detection: 250 nm.

Method 11 (GC-MS):

Instrument: Micromass GCT, GC 6890; column: Restek RTX-35, 15 m×200 μm×0.33 μm; constant flow with helium: 0.88 ml/min; oven: 70° C.; inlet: 250° C.; gradient: 70° C., 30° C./min→310° C. (hold for 3 min)

Method 12 (LC-MS):

Instrument: Micromass Quattro LCZ with HPLC Agilent Series 1100; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 208-400 nm.

Method 13 (LC-MS):

MS instrument type: Waters ZQ; HPLC instrument type: Waters Alliance 2795; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 210 nm.

Starting Compounds and Intermediates

Example 1A

1-[2-(allyloxy)phenyl]ethanone

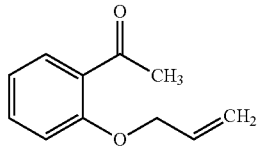

542 g (3.9 mol) of 2-hydroxyacetophenone are heated to reflux with 592 g (4.9 mol) of allyl bromide, 1000 g (7.2 mol) of potassium carbonate and 13.2 g (79 mmol) of potassium iodide in 2.4 liters of acetone for 24 h. Cooling to room temperature is followed by filtration, and the solvent is removed in vacuo. The residue is dissolved in toluene and washed with 10% strength sodium hydroxide solution and water. Concentration results in 689 g (98% of theory) of the title compound.

$^1$H-NMR (300 MHz, CDCl$_3$): δ=2.68 (s, 3H), 4.68 (dd, 2H), 5.89 (dd, 2H), 6.09 (m, 1H), 6.99 (dd, 2H), 7.44 (m, 1H), 7.71 (d, 1H).

Example 2A 1-(3-allyl-2-hydroxyphenyl)ethanone

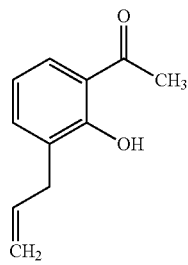

160 g (0.9 mol) of 1-[2-(allyloxy)phenyl]ethanone are stirred in a metal bath at 230-240° C. for 4 h. After cooling to room temperature, the product is distilled in a thin-film evaporator at 140° C. and 0.4 mbar. 155 g (97% of theory) of the title compound are obtained.

$^1$H-NMR (300 MHz, CDCl$_3$): δ=2.68 (s, 3H), 3.44 (d, 2H), 5.09 (m, 2H), 6.01 (m, 1H), 6.85 (t, 1H), 7.38 (dd, 1H), 7.62 (dd, 1H), 12.61 (s, 1H).

Example 3A

1-{2-Hydroxy-3-[(1E)-prop-1-en-1-yl]phenyl}ethanone

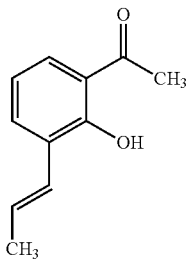

40 g (227 mmol) of 1-(3-allyl-2-hydroxyphenyl)ethanone are dissolved in 120 ml of toluene, and 2.17 g (5.6 mmol) of bis(benzonitrile)dichloropalladium(II) are added. The reaction mixture is heated at 120° C. overnight. Cooling to room temperature is followed by filtration through kieselguhr, and the solvent is removed in vacuo. 20.9 g (95% of theory) of the title compound are obtained and are reacted without further purification in the next stage.

LC-MS (method 1): R$_t$=2.36 min; [M+H]$^+$=177

$^1$H-NMR (300 MHz, CDCl$_3$): δ=1.91 (dd, 3H), 2.63 (s, 3H), 6.32 (m, 1H), 6.73 (dd, 1H), 6.85 (t, 1H), 7.59 (m, 2H), 12.74 (s, 1H).

Example 4A

2-Methyl-8-[(1E)-prop-1-en-1-yl]-4H-chromen-4-one

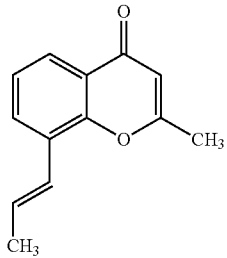

12.52 g (313.2 mmol) of 60% sodium hydride (suspension in mineral oil) are introduced into 300 ml of absolute THF under argon at 10° C. 18.4 g (104.4 mmol) of 1-{2-hydroxy-3-[(1E)-prop-1-en-1-yl]phenyl}ethanone are slowly added dropwise to the suspension. After 15 min, 9 g (114.9 mmol) of acetyl chloride are added. The reaction mixture is stirred at room temperature overnight. Hydrolysis is carried out with 300 ml of water, and the mixture is extracted several times with ethyl acetate. Washing of the organic phase with saturated sodium chloride solution is followed by drying over sodium sulfate. The solvent is then removed in vacuo. The residue is taken up in 200 ml of methanol and heated with 50 ml of 20% strength hydrochloric acid at 80° C. for 30 min. The solvent is then removed in vacuo, and the residue is mixed with 400 ml of water. Several extractions with dichloromethane are carried out. After the organic phase has been dried over magnesium sulfate, the solvent is removed in vacuo and the residue is purified by column chromatography (mobile phase: dichloromethane/methanol 98:2). 10.5 g (50.2% of theory) of the title compound are obtained as a yellow oil.

LC-MS (method 2): $R_t$=2.07 min; [M+H]$^+$=201

$^1$H-NMR (300 MHz, CDCl$_3$): δ=1.98 (dd, 3H), 2.43 (s, 3H), 6.18 (s, 1H), 6.40 (m, 1H), 6.85 (dd, 1H), 7.31 (t, 1H), 7.72 (dd, 1H), 8.05 (dd, 1H).

Example 5A

2-Methyl-4-oxo-4H-chromene-8-carbaldehyde

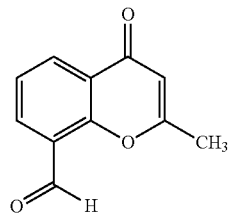

18.5 g (62.8 mmol) of 2-methyl-8-[(1E)-prop-1-en-1-yl]-4H-chromen-4-one are dissolved in 400 ml of dichloromethane and cooled to −60° C. Ozone is passed into the reaction solution for 30 min Dimethyl sulfide is then added to the reaction mixture. After warming to room temperature, the solvent is removed in vacuo and the residue is slurried in a little methanol. The solid remaining after filtration is recrystallized from diethyl ether. 9.1 g (77.4% of theory) of the title compound are obtained.

LC-MS (method 1): $R_t$=1.31 min; [M+H]$^+$=189

$^1$H-NMR (300 MHz, CDCl$_3$): δ=2.48 (s, 3H), 6.27 (s, 1H), 7.51 (m, 1H), 8.21 (dd, 1H), 8.46 (dd, 1H), 10.67 (s, 1H).

Example 6A

3-[(2-Methyl-4-oxo-4H-chromen-8-yl)methylene]pentane-2,4-dione

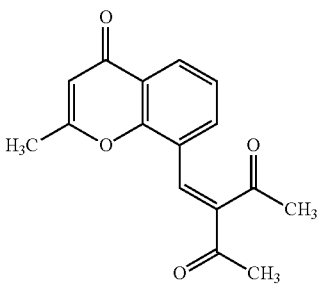 [SMILES: CC(=O)C(=Cc1cccc2c(=O)cc(C)oc12)C(C)=O]

20 g (106 mmol) of 2-methyl-4-oxo-4H-chromene-8-carbaldehyde, 12 ml (116 mmol) of 2,4-pentanedione, 9.1 ml (159 mmol) of acetic acid and 0.21 ml (2.1 mmol) of piperidine in 400 ml of anhydrous dichloromethane are stirred under reflux with a water trap for 24 h. After cooling, the reaction solution is washed successively with saturated sodium bicarbonate solution and saturated sodium chloride solution. The organic phase is dried over magnesium sulfate and concentrated. The residue is recrystallized from isopropanol. 24.3 g (73% of theory) of the title compound are obtained as a white solid.

LC-MS (method 4): $R_t$=1.91 min; [M+H]$^+$=271

$^1$H-NMR (300 MHz, DMSO-d$_6$): δ=2.24 (s, 3H), 2.44 (s, 3H), 2.54 (s, 3H), 6.33 (s, 1H), 7.49 (t, 1H), 7.64 (dd, 1H), 7.97 (s, 1H), 8.07 (dd, 1H).

Example 7A

3-Acetyl-2-methyl-4-(2-methyl-4-oxo-4H-chromen-8-yl)-4,6-dihydro-1,6-naphthyridin-5(1H)-one

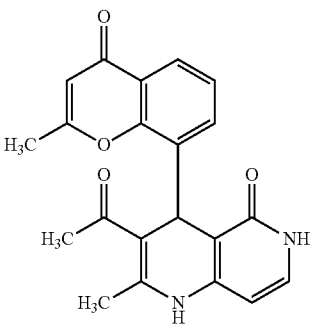 [SMILES: CC(=O)C1=C(C)Nc2cc[nH]c(=O)c2C1c1cccc2c(=O)cc(C)oc12]

4.00 g (14.79 mmol) of 3-[(2-methyl-4-oxo-4H-chromen-8-yl)methylene]pentane-2,4-dione and 1.63 g (14.79 mmol) of 4-aminopyridin-2(1H)-one [Searls, T., McLaughlin, L. W., Tetrahedron 55, 11985-11996 (1999)] are dissolved in 40 ml of isopropanol and heated at the reflux temperature under argon for 4 days. The mixture is then concentrated and the residue is recrystallized from methanol. 4.1 g (76% of theory) of the title compound are obtained as a yellow solid.

LC-MS (method 4): $R_t$=1.26 min; [M+H]$^+$=363

$^1$H-NMR (300 MHz, DMSO-d$_6$): δ=2.13 (s, 3H), 2.28 (s, 3H), 2.36 (s, 3H), 5.45 (s, 1H), 5.93 (d, 1H), 6.18 (s, 1H), 7.12 (m, 1H), 7.31 (t, 1H), 7.64 (dd, 1H), 7.78 (dd, 1H), 9.35 (s, 1H), 10.82 (s, 1H).

Example 8A

4-Bromo-2-(trifluoromethoxy)benzaldehyde

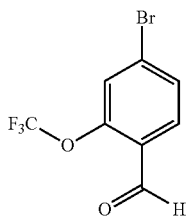

20.00 g (54.51 mmol) of 4-bromo-2-(trifluoromethoxy)iodobenzene are dissolved in 200 ml of THF and cooled to −78° C. Then 26.16 ml (65.41 mmol) of a 2.5 M solution of n-butyllithium in hexane are added dropwise. The mixture is stirred for 30 min and then 14.43 g (125.37 mmol) of N-formylmorpholine are metered in. After complete conversion is detected (TLC check), solvolysis is carried out at −78° C. with isopropanol. Warming to room temperature is followed by addition of water and extraction twice with dichloromethane. The combined organic phases are washed with saturated sodium chloride solution and dried with sodium sulfate, and the solvent is distilled out under reduced pressure. The residue is purified by column chromatography (silica gel, mobile phase: cyclohexane/ethyl acetate 5:1). 11.43 g (78% of theory) of the title compound are obtained.

GC-MS (method 7): $R_t$=4.24 min; MS (EIpos): m/z=270 [M+H]$^+$ $^1$H-NMR (300 MHz, DMSO-d$_6$): δ=7.85-7.92 (m, 3H), 10.20 (s, 1H).

Example 9A

4-Formyl-3-(trifluoromethoxy)benzonitrile

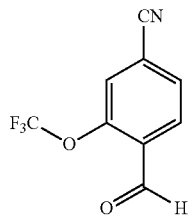 [SMILES: N#Cc1ccc(C=O)c(OC(F)(F)F)c1]

10.63 g (39.51 mmol) of 4-bromo-2-(trifluoromethoxy)benzaldehyde, 3.43 g (29.24 mmol) of zinc cyanide and 1.37 g (1.19 mmol) of tetrakis(triphenylphosphine)palladium(0) are dissolved in 80 ml of DMF. The reaction mixture is then reacted in several portions in a single mode microwave (Emrys Optimizer, 5 min at 220° C.). The combined mixtures are mixed with water and extracted twice with toluene. The combined organic phases are washed with saturated sodium chloride solution and dried with sodium sulfate, and then the solvent is removed in a rotary evaporator. The residue is purified by column chromatography (silica gel, mobile phase: cyclohexane/ethyl acetate 10:1). 3.32 g (78% of theory) of the title compound are obtained with a purity of 80% (according to LC-MS).

MS (EIpos): m/z=215 [M]$^+$ $^1$H-NMR (300 MHz, DMSO-d$_6$): δ=7.85-7.91 (m, 3H), 10.20 (s, 1H).

Example 10A 4-(3-Acetyl-2-methyl-5-oxo-1,4,5,6-tetrahydro-1,6-naphthyridin-4-yl)-3-(trifluoromethoxy)benzonitrile

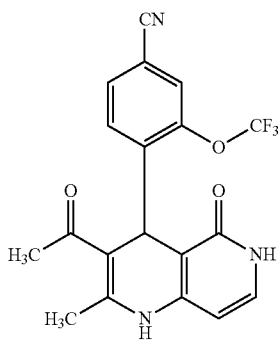 [SMILES: CC(=O)C1=C(C)Nc2cc[nH]c(=O)c2C1c1ccc(C#N)cc1OC(F)(F)F]

3.32 g (15.43 mmol) of 4-formyl-3-(trifluoromethoxy)benzonitrile, 1.55 g (15.43 mmol) of 2,4-pentanedione, 1.39 g of acetic acid (23.15 mmol) and 262 mg (3.09 mmol) of piperidine are dissolved in 150 ml of dichloromethane and heated under reflux with an inverse water trap overnight. After complete conversion has been detected by a TLC check, the mixture is diluted with 100 ml of dichloromethane and washed with water and saturated sodium chloride solution. The solvent is removed in a rotary evaporator. 4.56 g (99% of theory) of crude 4-(2-acetyl-3-oxobut-1-en-1-yl)-3-(trifluoromethoxy)benzonitrile are obtained and are reacted directly without further purification.

3.32 g (10.73 mmol) of the benzylidene compound obtained in this way are dissolved in 100 ml of isopropanol and, while boiling, 1.31 g (10.73 mmol) of 4-aminopyridin-2(1H)-one [Searls, T., McLaughlin, L. W., Tetrahedron 55, 11985-11996 (1999)], dissolved in 60 ml of hot isopropanol, are added (adding the 4-aminopyridin-21H)-one as a suspension should be avoided in this connection). After stirring at the reflux temperature for three days, the solvent is removed in a rotary evaporator, the residue is taken up in methanol, and the resulting solid is filtered off 2.40 g (57% of theory) of the title compound are obtained.

LC-MS (method 4): $R_t$=1.72 min; MS (EIpos): m/z=390 [M+H]$^+$ $^1$H-NMR (300 MHz, DMSO-d$_6$): δ=2.12 (s, 3H), 2.27 (s, 3H), 5.29 (s, 1H), 5.89 (d, 1H), 7.14 (t, 1H), 7.58 (d, 1H), 7.65 (br. s, 1H), 7.69 (dd, 1H), 9.34 (s, 1H), 10.91 (s, 1H).

Example 11A

Sodium 1-cyanoprop-1-en-2-olate

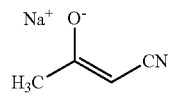

Sodium (7.69 g, 335 mmol) is introduced in portions into 350 ml of anhydrous methanol. After the reaction mixture has been cooled to 25° C., 5-methylisoxazole (27.8 g, 335 mmol) is slowly added in portions (exothermic reaction). After the addition is complete, the mixture is stirred at RT for 4 h and then concentrated. The residue is washed with a little diethyl ether, filtered off with suction and dried under oil pump vacuum. 32.0 g (91% of theory) of the title compound are obtained.

$^1$H-NMR (400 MHz, DMSO-d$_6$): δ=3.18 (s, 1H), 1.51 (s, 3H).

Example 12A

2-Methyl-4-(2-methyl-4-oxo-4H-chromen-8-yl)-5-oxo-1,4,5,6-tetrahydro-1,6-naphthyridine-3-carbonitrile

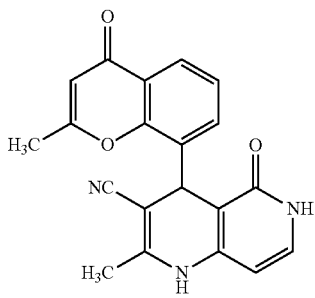 [SMILES: CC1=C(C#N)C(c2cccc3c(=O)cc(C)oc23)c2c(cc[nH]c2=O)N1]

300 mg (1.59 mmol) of 2-methyl-4-oxo-4H-chromene-8-carbaldehyde are dissolved with 167.5 mg (1.59 mmol) of sodium 1-cyanoprop-1-en-2-olate, 175 mg (1.59 mmol) of 4-aminopyridin-2(1H)-one [Searls, T., McLaughlin, L. W., *Tetrahedron* 55, 11985-11996 (1999)] and 137 µl (2.39 mmol) of acetic acid in 12 ml of 2-propanol and heated under reflux under argon for 12 h. After cooling, the reaction mixture is filtered and the remaining solid is washed with diethyl ether (20 ml). 454 mg (82% of theory) of the title compound are obtained as a white solid.

MS (ESI): [M+H]$^+$=346.2
$^1$H-NMR (300 MHz, DMSO-d$_6$): δ=2.06 (s, 3H), 2.38 (s, 3H), 5.14 (s, 1H), 5.97 (d, 1H), 6.25 (s, 1H), 7.22 (d, 1H), 7.37 (t, 1H), 7.43 (dd, 1H), 7.87 (dd, 1H), 10.02 (s, 1H), 11.11 (s, 1H).

Example 13A

4-Cyano-2-methoxyphenyl trifluoromethanesulfonate

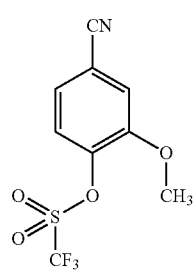 [SMILES: COc1cc(C#N)ccc1OS(=O)(=O)C(F)(F)F]

24 ml (141 mmol) of trifluoromethanesulfonic anhydride are slowly added dropwise to a solution of 20 g (134 mmol) of 4-hydroxy-3-methoxybenzonitrile in pyridine (80 ml), keeping the reaction temperature below 25° C. with the aid of an ice bath. The suspension is then stirred at RT for 1 h. Ice-water (400 ml) is added, and the suspension is stirred further until room temperature is reached. It is then filtered, the solid is dissolved in ethyl acetate, and the solution is washed with saturated sodium chloride solution. The organic phase is dried over magnesium sulfate and concentrated. 37.13 g (92% of theory) of the title compound are obtained as a white solid.

LC-MS (method 4): R$_t$=2.54 min; MS (EIpos): m/z=282 [M+H]$^+$
$^1$H-NMR (300 MHz, DMSO-d$_6$): δ=3.97 (s, 3H), 7.60 (dd, 1H), 7.71 (d, 1H), 7.92 (d, 1H).

Example 14A tert-Butyl (2E)-3-(4-cyano-2-methoxyphenyl)acrylate

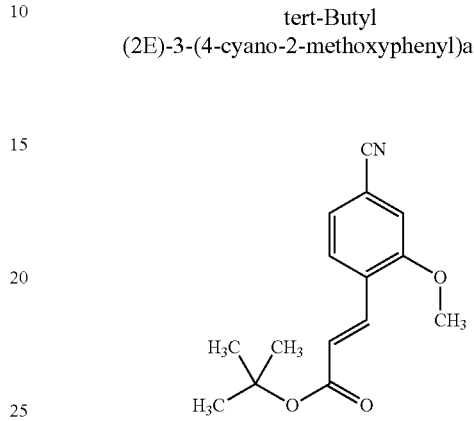

4 g (5.7 mmol) of bis(triphenylphosphine)palladium(II) chloride are added to a degassed solution of 37.13 g (132 mmol) of 4-cyano-2-methoxyphenyl trifluoromethanesulfonate, 35 ml (245 mmol) of tent-butyl acrylate and 90 ml (645 mmol) of triethylamine in DMF (250 ml). The solution is stirred at 100° C. under a protective gas atmosphere for 24 h. Ice-water (1000 ml) is then added, and the suspension is extracted with ethyl acetate (3×100 ml). The organic phase is washed with saturated sodium chloride solution, dried over magnesium sulfate and concentrated. The residue is purified by column chromatography (silica gel, mobile phase: cyclohexane/ethyl acetate 10:1). 24.6 g (72% of theory) of the title compound are obtained as a white solid.

LC-MS (method 1): R$_t$=2.59 min; MS (EIpos): m/z=260 [M+H]$^+$
$^1$H-NMR (300 MHz, DMSO-d$_6$): δ=1.48 (s, 9H), 3.93 (s, 3H), 6.65 (d, 1H), 7.42 (d, 1H), 7.58 (s, 1H), 7.74 (d, 1H), 7.89 (d, 1H).

Example 15A

4-Formyl-3-methoxybenzonitrile

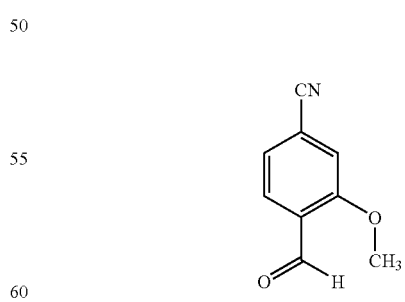

79 g (370 mmol) of sodium metaperiodate are added in portions to a vigorously stirred solution of 48 g (185 mmol) of tert-butyl (2E)-3-(4-cyano-2-methoxyphenyl)acrylate, 207 mg (0.81 mmol) of osmium tetroxide and 1.4 g (6.14 mmol) of benzyltriethylammonium chloride in 750 ml of water/THF (2:1), keeping the reaction temperature below 30° C. The solution is stirred at RT for a further 1 h. Water (2000 ml) is added and the mixture is then filtered. The remaining solid is dissolved in ethyl acetate, and the solution is washed with saturated sodium chloride solution. The organic phase is dried over magnesium sulfate and concentrated. The residue is stirred with petroleum ether. 21.18 g (71% of theory) of the title compound are obtained as a white solid.

LC-MS (method 4): $R_t$=1.87 min; MS (EIpos): m/z=162 [M+H]$^+$ $^1$H-NMR (300 MHz, DMSO-$d_6$): δ=3.98 (s, 3H), 7.53 (d, 1H), 7.80 (s, 1H), 7.81 (d, 1H), 10.37 (s, 1H).

Example 16A 4-(2-Acetyl-3-oxobut-1-en-1-yl)-3-methoxybenzonitrile

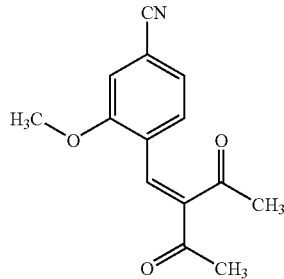

21 g (130 mmol) of 4-formyl-3-methoxybenzonitrile, 14.7 ml (143 mmol) of 2,4-pentanedione, 11.2 ml (195 mmol) of acetic acid and 2.6 ml (26 mmol) of piperidine in 400 ml of dry dichloromethane are stirred under reflux with a water trap for 24 h. After cooling, the reaction solution is washed successively with saturated sodium bicarbonate solution and saturated sodium chloride solution. The organic phase is dried over magnesium sulfate and concentrated. The residue is recrystallized from diethyl ether. 23.2 g (92% of theory) of the title compound are obtained as a pale brown solid.

LC-MS (method 4): $R_t$=2.05 min; [M+H]$^+$=244

$^1$H-NMR (300 MHz, DMSO-$d_6$): δ=2.20 (s, 3H), 2.42 (s, 3H), 3.89 (s, 3H), 7.37 (d, 1H), 7.46 (dd, 1H), 7.60 (d, 1H), 7.68 (s, 1H).

Example 17A 4-(3-Acetyl-2-methyl-5-oxo-1,4,5,6-tetrahydro-1,6-naphthyridin-4-yl)-3-methoxybenzonitrile

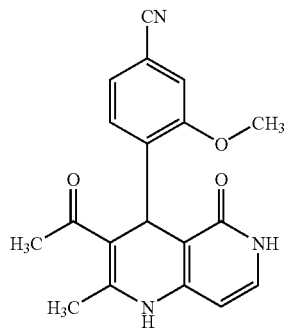 [SMILES: COc1cc(C#N)ccc1C1C(C(C)=O)=C(C)Nc2cc[nH]c(=O)c21]

18 g (74 mmol) of 4-(2-acetyl-3-oxobut-1-en-1-yl)-3-methoxybenzonitrile and 8.14 g (74 mmol) of 4-aminopyridin-2(1H)-one [Searls, T., McLaughlin, L. W., *Tetrahedron* 55, 11985-11996 (1999)] are dissolved in 40 ml of isopropanol and heated under reflux under argon for 4 days. The mixture is then concentrated and the residue is recrystallized from methanol. 18.1 g (70% of theory) of the title compound are obtained as a pale yellow solid.

LC-MS (method 4): $R_t$=1.46 min; MS (EIpos): m/z=336 [M+H]$^+$ $^1$H-NMR (300 MHz, DMSO-$d_6$): δ=2.14 (s, 3H), 2.15 (s, 3H), 3.79 (s, 3H), 5.32 (s, 1H), 5.92 (d, 1H), 7.10 (d, 1H), 7.14 (d, 1H), 7.27 (d, 1H), 7.37 (s, 1H), 9.18 (s, 1H), 10.90 (br. s, 1H).

Example 18A 4-(2-Acetyl-3-oxobut-1-en-1-yl)benzonitrile

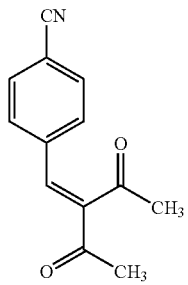 [SMILES: CC(=O)C(=Cc1ccc(C#N)cc1)C(C)=O]

2.3 g (17.5 mmol) of 4-formylbenzonitrile, 1.98 ml (19.29 mmol) of 2,4-pentanedione, 1 ml (26 mmol) of acetic acid and 0.34 ml (3.5 mmol) of piperidine in 40 ml of anhydrous dichloromethane are stirred under reflux with a water trap for 24 h. After cooling, the reaction solution is washed successively with saturated sodium bicarbonate solution and saturated sodium chloride solution. The organic phase is dried over magnesium sulfate and concentrated. The residue is recrystallized from diethyl ether. 3.18 g (85% of theory) of the title compound are obtained as a pale brown solid.

$^1$H-NMR (300 MHz, DMSO-$d_6$): δ=2.26 (s, 3H), 2.46 (s, 3H), 7.60 (d, 2H), 7.76 (s, 1H), 7.93 (d, 2H).

Example 19A 4-(3-Acetyl-2-methyl-5-oxo-1,4,5,6-tetrahydro-1,6-naphthyridin-4-yl)benzonitrile

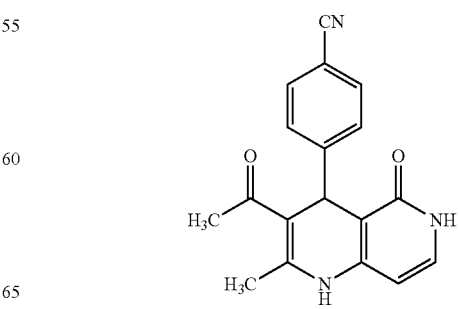

1.5 g (7.04 mmol) of 4-(2-acetyl-3-oxobut-1-en-1-yl)benzonitrile are mixed with 0.77 g (7.04 mmol) of 4-aminopyridin-2(1H)-one [Searls, T., McLaughlin, L. W., Tetrahedron 55, 11985-11996 (1999)], dissolved in 40 ml of isopropanol and heated under reflux under argon for 4 days. The mixture is then concentrated and the residue is recrystallized from methanol. 0.67 g (31% of theory) of the title compound is obtained as a pale yellow solid.

LC-MS (method 1): $R_t$=1.22 min; MS (EIpos): m/z=306 [M+H]$^+$ $^1$H-NMR (300 MHz, DMSO-$d_6$): δ=2.10 (s, 3H), 2.38 (s, 3H), 5.13 (s, 1H), 5.91 (d, 1H), 7.13 (t, 1H), 7.44 (d, 2H), 7.68 (d, 2H), 9.32 (s, 1H), 11.05 (br. s, 1H).

Example 20A

9-Oxo-9H-fluorene-4-carbaldehyde

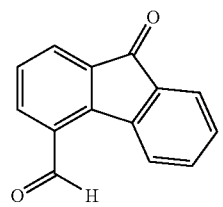 [SMILES: O=Cc1cccc2c1-c1ccccc1C2=O]

Methyl 9-oxo-9H-fluorene-4-carboxylate (9.85 g, 41.3 mmol) is introduced under argon into 180 ml of anhydrous THF. At RT, RED-AL® (38 ml, 136 mmol) [sodium bis-(2-methoxyethoxy)aluminum dihydride, 70% strength solution in toluene] is added dropwise over the course of 90 min, and the reaction mixture is then stirred for 1 h. The mixture is hydrolyzed by cautious dropwise addition of 15 ml of water. 60 ml of 6N hydrochloric acid are then added, and the mixture is extracted with ethyl acetate (4×150 ml each time). The combined organic phases are washed with saturated sodium chloride solution (2×100 ml each time), dried over sodium sulfate and concentrated in a rotary evaporator. 12.1 g of the corresponding alcohol are obtained. 8.77 g (41.3 mmol) of this are dissolved in 200 ml of dioxane, and activated manganese dioxide (25.1 g, 289 mmol) is added. The mixture is stirred at RT for 1 h and then at 50° C. for 30 min. The oxidizing agent is filtered off with suction, the residue on the filter is washed with dioxane (3×50 ml each time), and the filtrate is concentrated in a rotary evaporator. The resulting crude material is purified by chromatography on silica gel (mobile phase gradient: cyclohexane→cyclohexane/ethyl acetate 3:1). 6.50 g (76% of theory) of the title compound are obtained.

LC-MS (method 5): $R_t$=2.14 min; MS (ESIpos): m/z=209 [M+H]$^+$ $^1$H-NMR (400 MHz, DMSO-$d_6$): δ=7.50 (dd, 1H), 7.62 (dd, 1H), 7.69 (m, 2H), 7.90 (d, 1H), 8.12 (d, 1H), 8.39 (d, 1H), 10.5 (s, 1H).

Example 21A

3-Oxo-2-[(9-oxo-9H-fluoren-4-yl)methylene]butanenitrile

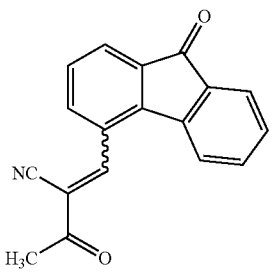

The compound from example 11A (5.21 g, 25.0 mmol) is introduced into 180 ml of dichloromethane, and the compound from example 20A (2.89 g, 27.5 mmol), acetic acid (1.72 ml, 30.0 mmol) and piperidine (0.25 ml, 2.50 mmol) are added. The mixture is stirred at the boiling point with a water trap for 4 h. Cooling to RT is followed by dilution with 30 ml of dichloromethane and washing with water (2×50 ml), the organic phase is dried over sodium sulfate and the solvent is removed in a rotary evaporator. The resulting crude product is purified by chromatography on silica gel 60 with dichloromethane as mobile phase. Combining the product fractions and removing the solvent results in 5.40 g (79% of theory) of the title compound as mixture of E/Z isomers.

LC-MS (method 5): $R_t$=2.24 min; MS (ESIpos): m/z=274 [M+H]$^+$ $^1$H-NMR (400 MHz, DMSO-$d_6$): δ=2.64 (s, 3H), 7.49 (t, 1H), 7.59 (t, 1H), 7.64 (d, 1H), 7.69 (d, 1H), 7.73 (d, 1H), 7.81 (d, 1H), 7.90 (d, 1H), 8.88 (s, 1H).

Example 22A

3-Acetyl-6-({[(1R,4S)-7,7-dimethyl-2-oxobicyclo [2.2.1]hept-1-yl]methyl}sulfonyl)-2-methyl-4-(2-methyl-4-oxo-4H-chromen-8-yl)-4,6-dihydro-1,6-naphthyridin-5(1H)-one Diastereomer A and Diastereomer B

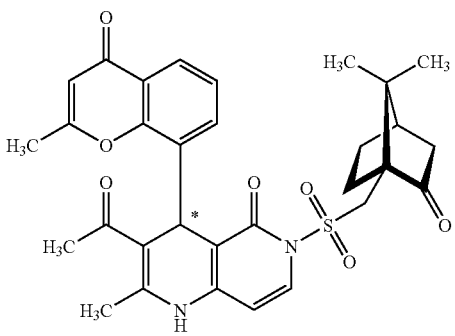

700 mg (1.9 mmol) of 3-acetyl-2-methyl-4-(2-methyl-4-oxo-4H-chromen-8-yl)-4,6-dihydro-1,6-naphthyridin-5(1H)-one are suspended in DMF (4 ml), and 247 mg (3 mmol) of lithium tert-butoxide are added. Then 824 mg (3.1 mmol) of (1S)-(+)-camphor-10-sulfonyl chloride in 2 ml of DMF are added dropwise to the dark red solution. The decolorized solution is stirred for a further 10 min and then solvolyzed with methanol, and 40 ml of 0.1 M hydrochloric acid are added. The precipitate remaining after filtration is washed with water. The solid is purified further by preparative HPLC, thus fractionating into the diastereomerically pure title compounds.

Diastereomer A:

Yield: 254 mg (23% of theory)

LC-MS (method 4): $R_t$=2.01 min; $[M+H]^+$=577

$^1$H-NMR (400 MHz, DMSO-$d_6$): δ=0.30 (t, 3H), 0.87 (t, 3H), 1.24-1.45 (m, 2H), 1.50 (dd, 1H), 1.58 (m, 1H), 1.73 (d, 1H), 1.85 (m, 1H), 2.18 (s, 3H), 2.24 (m, 1H), 2.29 (s, 3H), 2.35 (s, 3H), 3.91 (AB-system, 2H), 5.50 (s, 1H), 6.20 (s, 1H), 6.24 (d, 1H), 7.33 (t, 1H), 7.70 (m, 2H), 7.80 (dd, 1H), 9.76 (s, 1H).

Diastereomer B:

Yield: 245 mg (22% of theory)

LC-MS (method 4): $R_t$=2.05 min; $[M+H]^+$=577

$^1$H-NMR (400 MHz, DMSO-$d_6$): δ=0.55 (t, 3H), 0.87 (t, 3H), 1.24-1.45 (m, 2H), 1.73 (d, 1H), 1.94 (m, 3H), 2.09 (m, 1H), 2.18 (s, 3H), 2.29 (s, 3H), 2.35 (s, 3H), 3.65 (d, 1H), 4.15 (d, 1H), 5.48 (s, 1H), 6.16 (s, 1H), 6.21 (d, 1H), 7.29 (t, 1H), 7.68 (d, 2H), 7.77 (dd, 1H), 9.74 (s, 1H).

Example 23A ent-3-Acetyl-2-methyl-4-(2-methyl-4-oxo-4H-chromen-8-yl)-4,6-dihydro-1,6-naphthyridin-5(1H)-one

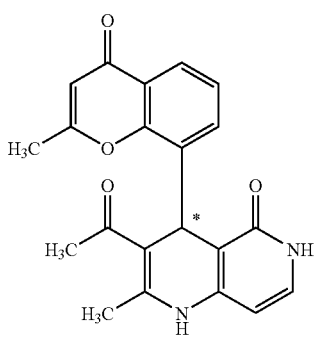 [SMILES: CC(=O)C1=C(C)Nc2cc[nH]c(=O)c2C1c1cccc2c(=O)cc(C)oc12]

240 mg (0.41 mmol) of diastereomer B of 3-acetyl-6-({[(1R,4S)-7,7-dimethyl-2-oxobicyclo[2.2.1]-hept-1-yl]methyl}sulfonyl)-2-methyl-4-(2-methyl-4-oxo-4H-chromen-8-yl)-4,6-dihydro-1,6-naphthyridin-5(1H)-one from example 22A are dissolved in methanol (5 ml), and 4 ml of aqueous sodium carbonate solution (0.2 M, 0.8 mmol) are added. The reaction mixture is stirred at RT for 12 h. It is then neutralized with 1N hydrochloric acid, and the solution is purified directly by preparative HPLC. 105 mg (70% of theory) of enantiomerically pure title compound are obtained as a white solid.

LC-MS (method 1): $R_t$=1.07 min; $[M+H]^+$=363

$^1$H-NMR (300 MHz, DMSO-$d_6$): δ=2.13 (s, 3H), 2.28 (s, 3H), 2.36 (s, 3H), 5.45 (s, 1H), 5.93 (d, 1H), 6.18 (s, 1H), 7.12 (m, 1H), 7.31 (t, 1H), 7.64 (dd, 1H), 7.78 (dd, 1H), 9.35 (s, 1H), 10.82 (s, 1H).

Example 24A

4-Formyl-3-hydroxybenzonitrile

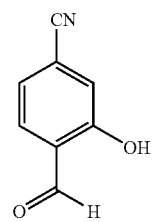 [SMILES: N#Cc1ccc(C=O)c(O)c1]

100 ml of a boron tribromide solution in dichloromethane (1 M, 100 mmol) are added dropwise to a solution of 8 g (49.64 mmol) of 4-formyl-3-methoxybenzonitrile in 80 ml of anhydrous dichloromethane at −78° C. under an argon atmosphere. The reaction mixture is stirred at RT until the precursor has completely reacted (about 5 days). The reaction solution is then neutralized at 0° C. with saturated sodium bicarbonate solution. The phases are separated and the organic phase is washed with saturated sodium chloride solution, dried over magnesium sulfate and concentrated. The residue is purified by column chromatography on silica gel (mobile phase: cyclohexane/ethyl acetate 3:1). 4.5 g (61% of theory) of the title compound are obtained as a yellow solid.

LC-MS (method 1): $R_t$=1.38 min; $[M-H]^-$=146

$^1$H-NMR (300 MHz, CDCl$_3$): δ=7.38 (d, 1H), 7.38 (s, 1H), 7.77 (d, 1H), 10.33 (s, 1H), 11.38 (s, 1H).

Example 25A

5-Cyano-2-formylphenyl trifluoromethanesulfonate

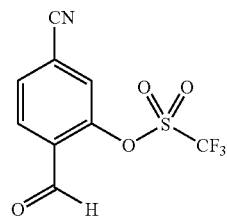 [SMILES: N#Cc1ccc(C=O)c(OS(=O)(=O)C(F)(F)F)c1]

2.4 ml (14.27 mmol) of trifluoromethanesulfonic anhydride are added dropwise to a solution of 2 g (13.59 mmol) of 4-formyl-3-hydroxybenzonitrile and 2.5 ml (14.27 mmol) of N,N-diisopropylethylamine in 37 ml of anhydrous dichloromethane at 0° C. under an argon atmosphere. The reaction mixture is stirred at RT for 1 h, then diluted with 70 ml of dichloromethane and washed successively with 1 M hydrochloric acid, saturated sodium bicarbonate solution and saturated sodium chloride solution. The organic solution is dried over magnesium sulfate and concentrated. The residue is purified by column chromatography on silica gel (mobile phase: cyclohexane/ethyl acetate 7:1). 2.36 g (62% of theory) of the title compound are obtained as a white solid.

LC-MS (method 4): $R_t$=2.34 min; $[M+H]^+$=280

$^1$H-NMR (300 MHz, CDCl$_3$): δ=8.27 (m, 2H), 8.33 (s, 1H), 10.13 (s, 1H).

Example 26A

4-Formyl-3-vinylbenzonitrile

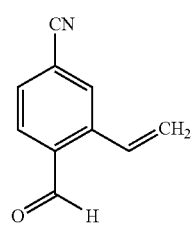

125 mg (0.18 mmol) of bis(triphenylphosphine)palladium (II) chloride are added to a solution of 1 g (3.58 mmol) of 5-cyano-2-formylphenyl trifluoromethanesulfonate and 1.15 ml (3.94 mmol) of tri-n-butylvinylstannane in 6 ml of anhydrous and degassed DMF under an argon atmosphere. The reaction mixture is then stirred at 80° C. for 90 min Subsequently, 100 ml of 10% strength potassium fluoride solution are added, and the mixture is stirred at RT for 1 h. The suspension is extracted three times with 20 ml of ethyl acetate each time, and the combined organic phases are washed successively with saturated sodium bicarbonate solution and saturated sodium chloride solution. The organic solution is dried over magnesium sulfate and concentrated. The residue (0.6 g) is employed without further purification in the next stage.

GC-MS (method 7): R$_t$=5.02 min; [M]$^+$=157

$^1$H-NMR (300 MHz, CDCl$_3$): δ=5.62 (d, 1H), 6.05 (d, 1H), 7.58 (dd, 1H), 7.95 (d, 1H), 8.00 (d, 1H), 8.24 (s, 1H), 10.32 (s, 1H).

Example 27A

3-Ethyl-4-formylbenzonitrile

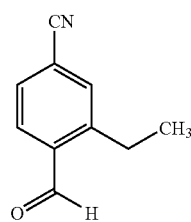

A solution of 1.3 g (8.27 mmol) of 4-formyl-3-vinylbenzonitrile in 35 ml of ethanol is mixed with 880 mg of 10% palladium on carbon and vigorously stirred under a hydrogen atmosphere for 2 h. The suspension is filtered through a layer of kieselguhr, the residue is washed with ethanol, and the filtrate is concentrated. The residue (890 mg) is employed without further purification in the following stage.

$^1$H-NMR (300 MHz, CDCl$_3$): δ=1.2 (t, 1H), 3.07 (q, 2H), 7.88 (d, 1H), 7.90 (s, 1H), 7.97 (d, 1H), 10.32 (s, 1H).

Example 28A 4-(2-Acetyl-3-oxobut-1-en-1-yl)-3-ethylbenzonitrile

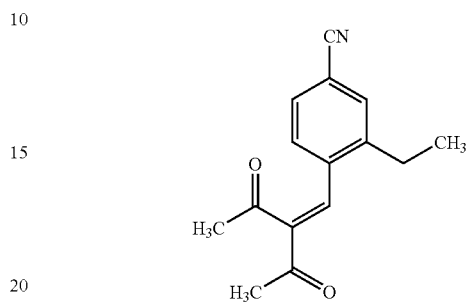

885 mg (5.55 mmol) of 3-ethyl-4-formylbenzonitrile, 0.62 ml (6.11 mmol) of 2,4-pentanedione, 0.47 ml (8.33 mmol) of acetic acid and 0.11 ml (1.11 mmol) of piperidine in 40 ml of anhydrous dichloromethane are stirred under reflux with a water trap for 24 h. After cooling, the reaction solution is washed successively with saturated sodium bicarbonate solution and saturated sodium chloride solution. The organic phase is dried over magnesium sulfate and concentrated. The residue (1.07 g) is reacted further without further purification.

$^1$H-NMR (300 MHz, CDCl$_3$): δ=1.17 (t, 1H), 2.10 (s, 3H), 2.46 (s, 3H), 2.76 (q, 2H), 7.24 (d, 1H), 7.68 (d, 1H), 7.79 (s, 1H), 7.90 (s, 1H).

Example 29A 4-(3-Acetyl-2-methyl-5-oxo-1,4,5,6-tetrahydro-1,6-naphthyridin-4-yl)-3-ethylbenzonitrile

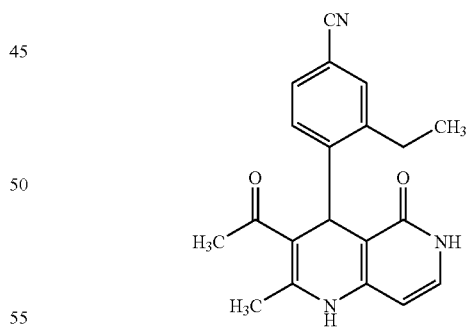

1 g (4.14 mmol) of 4-(2-acetyl-3-oxobut-1-en-1-yl)-3-ethylbenzonitrile and 0.45 g (4.14 mmol) of 4-aminopyridin-2 (1H)-one [Scats, T., McLaughlin, L. W., Tetrahedron 55, 11985-11996 (1999)] are dissolved in 20 ml of isopropanol and stirred at the reflux temperature under argon for 4 days. The mixture is then concentrated and the residue is purified by column chromatography on silica gel (mobile phase: dichloromethane/methanol 10:1). 277 mg (20% of theory) of the title compound are obtained as a pale yellow solid.

LC-MS (method 1): R$_t$=1.44 min; [M+H]$^+$=334

¹H-NMR (300 MHz, CDCl₃): δ=1.26 (t, 3H), 2.14 (s, 3H), 2.34 (s, 3H), 3.19 (m, 1H), 3.40 (m, 1H), 5.24 (s, 1H), 5.92 (d, 1H), 7.11 (t, 1H), 7.29 (d, 1H), 7.46 (m, 2H), 9.26 (s, 1H), 10.87 (s, 1H).

Example 30A 4-(4-Cyano-2-methoxyphenyl)-2-methyl-5-oxo-1,4,5,6-tetrahydro-1,6-naphthyridine-3-carbonitrile

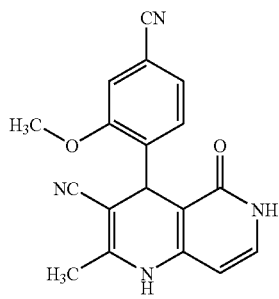

1.05 g (6.51 mmol) of 4-formyl-3-methoxybenzonitrile are dissolved with 684 mg (6.51 mmol) of sodium 1-cyanoprop-1-en-2-olate, 789 mg (7.16 mmol) of 4-aminopyridin-2(1H)-one [Searls, T., McLaughlin, L. W., *Tetrahedron* 55, 11985-11996 (1999)] and 600 μl (9.77 mmol) of acetic acid in 30 ml of isopropanol and heated under reflux under argon for 12 h. Cooling is followed by filtration, and the remaining solid is washed with diethyl ether (40 ml). 1.96 g (94% of theory) of the title compound are obtained as a white solid.

LC-MS (method 4): R$_t$=1.17 min; [M+H]⁺=319

¹H-NMR (300 MHz, DMSO-d₆): δ=2.01 (s, 3H), 3.83 (s, 3H), 5.02 (s, 1H), 5.94 (d, 1H), 7.03 (d, 1H), 7.19 (d, 1H), 7.32 (d, 1H), 7.45 (s, 1H), 9.88 (s, 1H), 11.06 (s, 1H).

Example 31A

3-[4-Nitro-2-(trifluoromethyl)benzylidene]pentane-2,4-dione

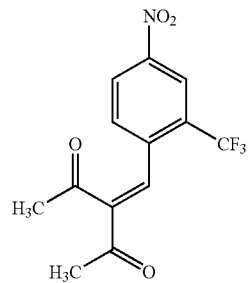 [SMILES: CC(=O)C(=Cc1ccc([N+](=O)[O-])cc1C(F)(F)F)C(C)=O]

1 g (4.56 mmol) of 2-trifluoromethyl-4-nitrobenzaldehyde, 0.51 ml (5.02 mmol) of 2,4-pentanedione, 0.4 ml (6.85 mmol) of acetic acid and 90 μl (0.91 mmol) of piperidine in 20 ml of anhydrous dichloromethane are stirred under reflux with a water trap for 24 h. After cooling, the reaction solution is washed successively with saturated sodium bicarbonate solution and saturated sodium chloride solution. The organic phase is dried over magnesium sulfate and concentrated. The residue (1.28 g) is reacted in the next stage without further purification.

LC-MS (method 3): R$_t$=2.34 min; [M+H]⁺=202.

Example 32A

3-Acetyl-2-methyl-4-[4-nitro-2-(trifluoromethyl)phenyl]-4,6-dihydro-1,6-naphthyridin-5(1H)-one

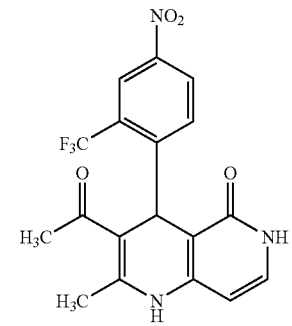 [SMILES: CC(=O)C1=C(C)Nc2cc[nH]c(=O)c2C1c1ccc([N+](=O)[O-])cc1C(F)(F)F]

1.28 g (4.24 mmol) of 3-[4-nitro-2-(trifluoromethyl)benzylidene]pentane-2,4-dione and 484 mg (4.24 mmol) of 4-aminopyridin-2(1H)-one [Searls, T., McLaughlin, L. W., *Tetrahedron* 55, 11985-11996 (1999)] are dissolved in 25 ml of isopropanol and heated under reflux under argon for 12 h. Cooling is followed by filtration, and the remaining solid is washed with diethyl ether (40 ml). 990 mg (58% of theory) of the title compound are obtained as a white solid.

LC-MS (method 1): R$_t$=1.51 min; [M+H]⁺=394

¹H-NMR (300 MHz, DMSO-d₆): δ=2.15 (s, 3H), 2.32 (s, 3H), 5.58 (s, 1H), 5.92 (d, 1H), 7.15 (t, 1H), 7.63 (d, 1H), 8.17 (d, 1H), 8.29 (dd, 1H), 9.32 (s, 1H), 10.84 (d, 1H).

Example 33A

Methyl 4-cyano-2-fluorobenzoate

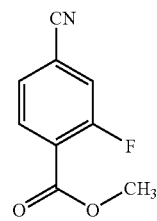

13.20 g (79.9 mmol) of 4-cyano-2-fluorobenzoic acid are dissolved in 300 ml of acetone. Then 22.10 g (159.9 mmol) of potassium carbonate and 9.08 ml (95.9 mmol) of dimethyl sulfate are successively added. The mixture is stirred at reflux temperature for 20 h. The reaction mixture is then mixed with 300 ml of water and the acetone is removed in a rotary evaporator. Several extractions with dichloromethane are carried out. The combined organic phases are washed with saturated sodium chloride solution and dried over sodium sulfate. The solvent is then removed in vacuo. The remaining solid is used further without further purification. 16.1 g (84% of theory) of the title compound are obtained as a colorless solid.

GC-MS (method 7): $R_t$=6.23 min; [M]$^+$ (EIpos): m/z=179

$^1$H-NMR (300 MHz, DMSO-d$_6$): δ=3.90 (s, 3H), 7.83 (dd, 1H), 8.01-8.08 (m, 2H).

Example 34A

3-Fluoro-4-(hydroxymethyl)benzonitrile

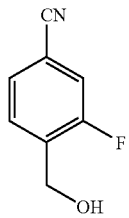

16.10 g (89.9 mmol) of methyl 4-cyano-2-fluorobenzoate are dissolved in 150 ml of methanol. Then 3.40 g (89.9 mmol) of sodium borohydride are added in portions. After the reaction has taken place (TLC check), the mixture is adjusted to pH 3 with dilute hydrochloric acid and extracted several times with dichloromethane. The combined organic phases are washed with saturated sodium chloride solution and dried with magnesium sulfate. The solvent is then removed in vacuo, and the residue is purified by column chromatography (silica gel, mobile phase: cyclohexane/ethyl acetate 15:1→3:7). 3.70 g (27.2% of theory) of the title compound are obtained.

GC-MS (method 7): $R_t$=6.51 min; [M]$^+$ (EIpos): m/z=151

$^1$H-NMR (300 MHz, DMSO-d$_6$): δ=4.61 (s, 2H), 5.53 (s, 1H), 7.61-7.74 (m, 2H), 7.79 (dd, 1H).

Example 35A

3-Fluoro-4-formylbenzonitrile

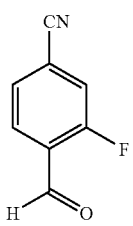

1.00 g (6.62 mmol) of 3-fluoro-4-(hydroxymethyl)benzonitrile are dissolved in 50 ml of dichloromethane, and 9.20 g (105.9 mmol) of manganese(IV) oxide are added. The mixture is stirred at room temperature overnight and then filtered through a short kieselguhr column. The solvent is distilled out under reduced pressure, and the residue is purified by column chromatography (silica gel, mobile phase: dichloromethane). 120 mg (12.1% of theory) of the title compound are obtained.

GC-MS (method 7): $R_t$=5.11 min; [M]$^+$ (EIpos): m/z=149

$^1$H-NMR (300 MHz, DMSO-d$_6$): δ=7.89 (d, 1H), 8.00 (t, 1H), 8.11 (d, 1H), 10.24 (d, 1H).

Example 36A 4-(3-Acetyl-2-methyl-5-oxo-1,4,5,6-tetrahydro-1,6-naphthyridin-4-yl)-3-fluorobenzonitrile

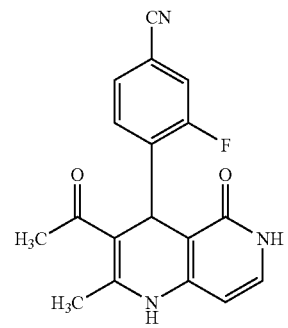 [SMILES: CC(=O)C1=C(C)Nc2cc[nH]c(=O)c2C1c1ccc(C#N)cc1F]

120 mg (0.805 mmol) of 3-fluoro-4-formylbenzonitrile, 80.6 mg (0.805 mmol) of 2,4-pentanedione, 72.5 mg (1.21 mmol) of acetic acid and 14 mg (0.16 mmol) of piperidine are dissolved in 8 ml of dichloromethane and heated under reflux with an inverse water trap overnight. The mixture shows complete conversion (TLC check, mobile phase: cyclohexane/ethyl acetate 5:1). The mixture is diluted with dichloromethane, washed with water and saturated sodium chloride solution and dried with sodium sulfate. The solvent is removed in a rotary evaporator. 155 mg (83.3% of theory) of 4-(2-acetyl-3-oxobut-1-en-1-yl)-3-fluorobenzonitrile are obtained and are reacted without further purification.

155 mg (0.670 mmol) of the benzylidene compound obtained in this way are taken up in 5 ml of isopropanol and, after addition of 73.8 mg (0.67 mmol) of 4-aminopyridin-2(1H)-one, reacted in a closed vessel at a bath temperature of 100° C. for 24 h. The mixture is then concentrated and the residue is purified by preparative HPLC (eluent: acetonitrile/water with 0.1% formic acid, gradient 20:80→95:5). 18 mg (8.3% of theory based on the intermediate 4-(2-acetyl-3-oxobut-1-en-1-yl)-3-fluorobenzonitrile) of the title compound are obtained.

LC-MS (method 4): $R_t$=1.49 min; [M+H]$^+$ (EIpos): m/z=324

$^1$H-NMR (300 MHz, DMSO-d$_6$): δ=2.13 (s, 3H), 2.30 (s, 3H), 5.25 (s, 1H), 5.91 (d, 1H), 7.15 (t, 1H), 7.41 (t, 1H), 7.54 (d, 1H), 7.65 (d, 1H), 9.34 (s, 1H), 10.98 (s, 1H).

Example 37A

3-Chloro-4-formylbenzonitrile

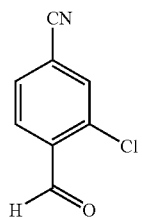

25.0 g (164.91 mmol) of 3-chloro-4-methylbenzonitrile are dissolved in 150 ml of DMF, and 25.55 g (214.39 mmol) of N,N-dimethylformamide dimethyl acetal are added. The mixture is stirred in an oil bath at a temperature of 140° C. for 20 h and then at 180° C. for 4 h. The volatile components are removed in a rotary evaporator, and the remaining residue is directly reacted further.

The crude 3-chloro-4-[2-(dimethylamino)vinyl]benzonitrile obtained in this way is taken up in 500 ml of THF/water (1:1), and 77.6 g (362.9 mmol) of sodium periodate are added. The mixture is stirred at room temperature for 18 h, and then the precipitate which has separated out is removed by filtration. The filtrate is mixed with saturated sodium bicarbonate solution and extracted three times with ethyl acetate. The combined organic phases are dried with sodium sulfate, and the solvent is removed in a rotary evaporator. The crude product is purified by column chromatography (silica gel, mobile phase: cyclohexane/ethyl acetate 7:3). 3.0 g (15% of theory) of the title compound are obtained.

GC-MS (method 7): R$_t$=6.64 min; [M]$^+$ (EIpos): m/z=165

$^1$H-NMR (300 MHz, DMSO-d$_6$): δ=7.97-8.03 (m, 2H), 8.27 (s, 1H), 10.34 (d, 1H).

Example 38A 4-(3-Acetyl-2-methyl-5-oxo-1,4,5,6-tetrahydro-1,6-naphthyridin-4-yl)-3-chlorobenzonitrile

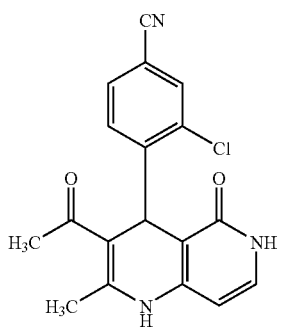 [SMILES: CC(=O)C1=C(C)Nc2cc[nH]c(=O)c2C1c1ccc(C#N)cc1Cl]

300 mg (1.812 mmol) of 3-chloro-4-formylbenzonitrile, 181.4 mg (1.812 mmol) of 2,4-pentanedione, 163.2 mg (2.72 mmol) of acetic acid and 30.9 mg (0.36 mmol) of piperidine are dissolved in 15 ml of dichloromethane and heated under reflux with an inverse water trap overnight. The mixture shows complete conversion (TLC check, mobile phase: cyclohexane/ethyl acetate 5:1). The mixture is diluted with dichloromethane, washed with water and saturated sodium chloride solution and dried with sodium sulfate. The solvent is removed in a rotary evaporator. 403 mg (89.8% of theory) of 4-(2-acetyl-3-oxobut-1-en-1-yl)-3-chlorobenzonitrile are obtained and are reacted without further purification.

403 mg (1.63 mmol) of the benzylidene compound obtained in this way are taken up in 8 ml of isopropanol, mixed with 179.2 mg (1.63 mmol) of 4-aminopyridin-2(1H)-one and heated at the reflux temperature for 24 h. The mixture is then concentrated and the residue is purified by preparative HPLC (eluent: acetonitrile/water with 0.1% formic acid, gradient 20:80→95:5). 251 mg (45.3% of theory based on the intermediate 4-(2-acetyl-3-oxobut-1-en-1-yl)-3-chlorobenzonitrile) of the title compound are obtained.

LC-MS (method 4): R$_t$=1.57 min; [M+H]$^+$ (EIpos): m/z=340

$^1$H-NMR (300 MHz, DMSO-d$_6$): δ=2.13 (s, 3H), 2.27 (s, 3H), 5.38 (s, 1H), 5.89 (d, 1H), 7.13 (t, 1H), 7.47 (d, 1H), 7.66 (dd, 1H), 7.82 (d, 1H), 9.31 (s, 1H), 10.89 (d, 1H).

Example 39A 4-(2-Acetyl-3-oxobut-1-en-1-yl)-3-methylbenzonitrile

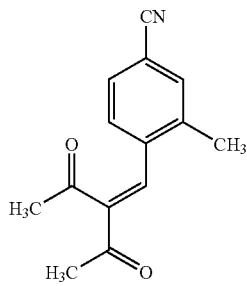 [SMILES: CC(=O)C(=Cc1ccc(C#N)cc1C)C(C)=O]

950 mg (6.54 mmol) of 3-methyl-4-formylbenzonitrile [S. Levesque et al., Bioorg. Med. Chem. Lett. 11, 3161-3164 (2000], 655.2 mg (6.544 mmol) of 2,4-pentanedione, 589.5 mg (9.82 mmol) of acetic acid and 111.5 mg (1.31 mmol) of piperidine are dissolved in 35 ml of dichloromethane and heated under reflux with an inverse water trap overnight. Cooling is followed by washing twice with water, and the organic phase is dried with magnesium sulfate. The solvent is removed in a rotary evaporator and the residue is purified by column chromatography (silica gel, mobile phase: initially dichloromethane, then isohexane/ethyl acetate 3:1). After concentration of the product fractions, the residue is crystallized from diethyl ether and dried under high vacuum. 1.12 g (75.3% of theory) of the title compound are obtained.

LC-MS (method 3): $R_f$=1.98 min; $[M+H]^+$ (EIpos): m/z=228

$^1$H-NMR (300 MHz, DMSO-$d_6$): δ=2.11 (s, 3H), 2.40 (s, 3H), 2.47 (s, 3H), 7.25 (d, 1H), 7.68 (d, 1H), 7.80 (s, 1H), 7.84 (s, 1H).

Example 40A 4-(3-Acetyl-2-methyl-5-oxo-1,4,5,6-tetrahydro-1,6-naphthyridin-4-yl)-3-methylbenzonitrile

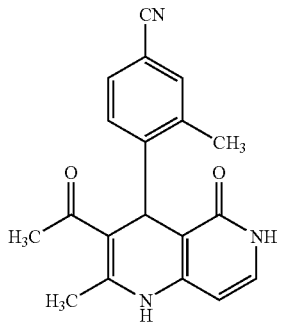 [SMILES: CC(=O)C1=C(C)Nc2cc[nH]c(=O)c2C1c1ccc(C#N)cc1C]

1.10 g (4.84 mmol) of 4-(2-acetyl-3-oxobut-1-en-1-yl)-3-methylbenzonitrile are taken up in 30 ml of isopropanol and, after addition of 592 mg (4.84 mmol) of 4-aminopyridin-2(1H)-one, heated at the reflux temperature for 72 h. The mixture is then concentrated, and the residue is again taken up in isopropanol and filtered through silica gel with isopropanol as eluent. The residue after concentration of the filtrate is mixed with a little methanol and crystallized. The precipitated product is filtered off, washed with diethyl ether and dried under high vacuum. 348 mg (22.5% of theory) of the title compound are obtained.

LC-MS (method 1): $R_f$=1.32 min; $[M+H]^+$ (EIpos): m/z=320

$^1$H-NMR (300 MHz, DMSO-$d_6$): δ=2.16 (s, 3H), 2.35 (s, 3H), 2.79 (s, 3H), 5.11 (s, 1H), 5.93 (d, 1H), 7.11 (d, 1H), 7.26 (d, 1H), 7.42-7.49 (m, 2H), 9.25 (s, 1H), 10.89 (d, 1H).

Example 41A 4-(3-Acetyl-2-methyl-5-oxo-1,4,5,6-tetrahydro-1,6-naphthyridin-4-yl)-3-(trifluoromethyl)benzonitrile

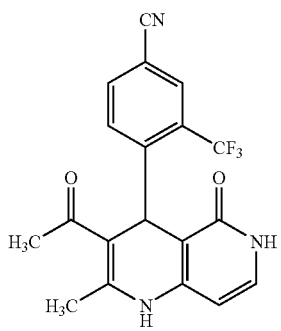 [SMILES: CC(=O)C1=C(C)Nc2cc[nH]c(=O)c2C1c1ccc(C#N)cc1C(F)(F)F]

3.00 g (16.20 mmol) of 3-trifluoromethyl-4-methylbenzonitrile are dissolved in 20 ml of DMF, and 2.67 g (21.06 mmol) of N,N-dimethylformamide dimethyl acetal are added. The mixture is stirred at 140° C. for 20 h. The volatile components are removed in a rotary evaporator and the remaining residue is directly reacted further.

The resulting crude product, about 50% of which consists of 3-trifluoromethyl-4-[2-(dimethylamino)vinyl]benzonitrile, is taken up in 500 ml of THF/water (1:1), and 8.20 g (38.3 mmol) of sodium periodate are added. The mixture is stirred at room temperature for 18 h and then the precipitate which has separated out is removed by filtration. The filtrate is mixed with saturated sodium bicarbonate solution and extracted three times with ethyl acetate. The combined organic phases are dried with sodium sulfate, and the solvent is removed in a rotary evaporator. The product mixture (3.07 g) obtained in this way consists according to GC-MS of about 40% 3-trifluoromethyl-4-formylbenzonitrile [GC-MS (method 11): $R_f$=3.29 min; $[M]^+$ (EIpos): m/z=199] and about 60% unreacted 3-trifluoromethyl-4-benzonitrile [GC-MS (method 11): $R_f$=2.88 min; $[M]^+$ (EIpos): m/z=185].

500 mg of the crude mixture obtained in this way (3-trifluoromethyl-4-formylbenzonitrile content about 1 mmol), 251.4 mg (2.511 mmol) of 2,4-pentanedione, 226.2 mg (3.77 mmol) of acetic acid and 42.8 mg (0.50 mmol) of piperidine are dissolved in 20 ml of dichloromethane and heated under reflux with an inverse water trap overnight. Cooling is followed by washing twice with water, and the organic phase is dried with magnesium sulfate. The solvent is removed in a rotary evaporator. The resulting crude material (288 mg) is mixed with 592 mg (4.84 mmol) of 4-aminopyridin-2(1H)-one, dissolved in 15 ml of isopropanol and then heated at the reflux temperature for 24 h. The mixture is then concentrated, and the residue is again taken up in isopropanol and filtered through silica gel with isopropanol as eluent. The residue after concentration of the filtrate is mixed with a little methanol, whereupon crystallization occurs. The precipitated product is filtered, washed with diethyl ether and dried under high vacuum. 50 mg (13.3% of theory based on the amount of 3-trifluoromethyl-4-formylbenzonitrile employed) of the title compound are obtained.

LC-MS (method 1): $R_f$=1.39 min; $[M+H]^+$ (EIpos): m/z=374

$^1$H-NMR (300 MHz, DMSO-$d_6$): δ=2.14 (s, 3H), 2.29 (s, 3H), 5.54 (s, 1H), 5.90 (d, 1H), 7.14 (t, 1H), 7.53 (d, 1H), 7.91 (d, 1H), 7.97 (d, 1H), 9.24 (s, 1H), 10.83 (d, 1H).

Example 42A

4-Formyl-1-naphthonitrile

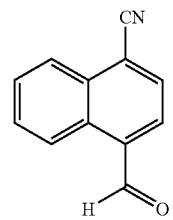

2.50 g (14.95 mmol) of 4-methyl-1-naphthonitrile are dissolved in 40 ml of tetrachloromethane and 3.19 g (17.94 mmol) of N-bromosuccinimide and 245 mg (1.50 mmol) of 2,2'-azobis-2-methyl-propanenitrile are added. The mixture is stirred at the reflux temperature overnight. After cooling, the product is filtered off. 2.75 g (74.7% of theory) of 4-(bromomethyl)-1-naphthonitrile are obtained in a purity of 90% and are reacted without further purification.

2.75 g (11.17 mmol) of the bromide obtained in this way are dissolved in 60 ml of acetonitrile, and 2 g of molecular sieves (3A) are added. Then 1.44 g (12.29 mmol) of N-methylmorpholine N-oxide are added, and the mixture is stirred at room temperature overnight. The mixture is then filtered through silica gel and the filtrate is concentrated. The residue is purified on a Biotage cartridge (40 M) (eluent: isohexane/ethyl acetate 3:1). The product fractions are combined, the solvent is removed in a rotary evaporator, and the residue is then stirred with diethyl ether, whereupon crystallization occurs. The product is washed with a little diethyl ether and dried under high vacuum. 254 mg (12.6% of theory) of the title compound are obtained.

LC-MS (method 3): $R_t$=2.27 min; $[M+H]^+$ (EIpos): m/z=182

$^1$H-NMR (300 MHz, CDCl$_3$): δ=7.79-7.87 (m, 2H), 8.05 (d, 1H), 8.09 (d, 1H), 8.37 (m, 1H), 9.27 (m, 1H), 10.51 (s, 1H).

Example 43A 4-(2-Acetyl-3-oxobut-1-en-1-yl)-1-naphthonitrile

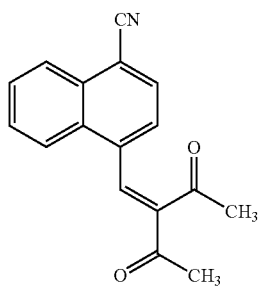 [SMILES: CC(=O)C(=Cc1ccc(C#N)c2ccccc12)C(C)=O]

240 mg (1.33 mmol) of 4-formyl-1-naphthonitrile, 132.6 mg (1.33 mmol) of 2,4-pentanedione, 119.3 mg (1.99 mmol) of acetic acid and 22.6 mg (0.27 mmol) of piperidine are dissolved in 20 ml of dichloromethane and heated under reflux with an inverse water trap overnight. Cooling is followed by washing twice with water, and the organic phase is dried with magnesium sulfate. The solvent is removed in a rotary evaporator and the residue is purified by column chromatography (silica gel, mobile phase: initially dichloromethane, then isohexane/ethyl acetate 3:1). The residue after concentration of the product fractions is crystallized from diethyl ether and dried under high vacuum. 340 mg (97.5% of theory) of the title compound are obtained.

LC-MS (method 1): $R_t$=2.03 min; $[M+H]^+$ (EIpos): m/z=264

$^1$H-NMR (300 MHz, CDCl$_3$): δ=2.09 (s, 3H), 2.60 (s, 3H), 7.49 (d, 1H), 7.84 (t, 1H), 7.91 (t, 1H), 8.19 (t, 2H), 8.31 (d, 1H), 8.36 (s, 1H).

Example 44A 4-(3-Acetyl-2-methyl-5-oxo-1,4,5,6-tetrahydro-1,6-naphthyridin-4-yl)-1-naphthonitrile

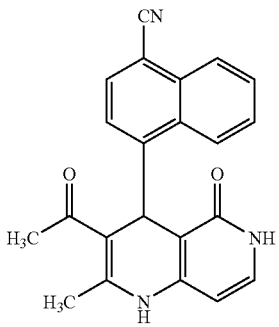 [SMILES: CC(=O)C1=C(C)Nc2cc[nH]c(=O)c2C1c1ccc(C#N)c2ccccc12]

325 mg (1.23 mmol) of 4-(2-acetyl-3-oxobut-1-en-1-yl)-1-naphthonitrile are taken up in 20 ml of isopropanol and, after addition of 151 mg (1.23 mmol) of 4-aminopyridin-2(1H)-one, heated at the reflux temperature for 72 h. The mixture is then concentrated and the residue is purified by preparative HPLC (eluent: acetonitrile/water with 0.1% formic acid, gradient 20:80→95:5). The product fractions are combined, the solvent is removed, and the residue is stirred with diethyl ether. The precipitated product is filtered off and dried under high vacuum. 91 mg (21.2% of theory) of the title compound are obtained.

LC-MS (method 1): $R_t$=1.51 min; $[M+H]^+$ (EIpos): m/z=356

$^1$H-NMR (300 MHz, DMSO-d$_6$): δ=2.03 (s, 3H), 2.39 (s, 3H), 5.90 (s, 1H), 5.97 (d, 1H), 7.11 (d, 1H), 7.49 (d, 1H), 7.73 (m, 2H), 8.03 (d, 2H), 9.10 (d, 1H), 9.39 (s, 1H), 10.84 (s, 1H).

Example 45A

Sodium 1-cyano-3,3,3-trifluoroprop-1-en-2-olate

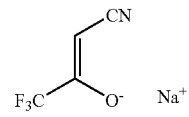

350 mg (14.6 mmol) of sodium are slowly introduced under argon into 20 ml of absolute methanol. After the sodium has completely dissolved, 2 g (14.6 mmol) of 5-trifluoromethylisoxazole [I. I. Gems et al., *J. Org. Chem. USSR (Engl. Transl.)* 26, 1623-1628 (1990); *Zh. Org. Khim.* 26, 1877-1883 (1990)] are added dropwise over the course of 5 min. The mixture is stirred at room temperature overnight. After removal of the solvent in vacuo, the product remains as a colorless solid. 2.31 g (90% of theory) are obtained and are employed without further purification.

$^1$H-NMR (400 MHz, DMSO-d$_6$): δ=3.68 (s, 1H).

Example 46A 4-(4-Cyano-2-methoxyphenyl)-5-oxo-2-(trifluoromethyl)-1,4,5,6-tetrahydro-1,6-naphthyridine-3-carbonitrile

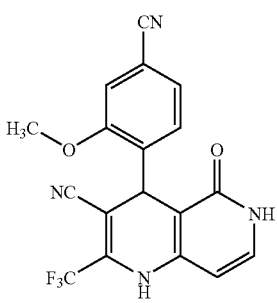

500 mg (3.1 mmol) of 4-formyl-3-methoxybenzonitrile are dissolved with 493 mg (3.1 mmol) of sodium 1-cyano-3,3,3-trifluoroprop-1-en-2-olate, 341 mg (3.1 mmol) of 4-aminopyridin-2(1H)-one [Searls, T., McLaughlin, L. W., Tetrahedron 55, 11985-11996 (1999)] and 266 µl (4.65 mmol) of acetic acid in 40 ml of isopropanol and heated under reflux under argon for 12 h. After cooling, the solution is concentrated, and the residue is again stirred in 45 ml of acetic acid under reflux overnight. The solution is cooled and then concentrated, and the residue is purified by preparative HPLC. 392 mg (34% of theory) of the title compound are obtained as a white solid.

LC-MS (method 1): $R_t$=1.63 min; $[M+H]^+$=373

$^1$H-NMR (300 MHz, DMSO-$d_6$): δ=3.83 (s, 3H), 5.12 (s, 1H), 6.12 (d, 1H), 7.21 (d, 1H), 7.25 (d, 1H), 7.38 (dd, 1H), 7.51 (d, 1H), 10.29 (s, 1H), 11.22 (s, 1H).

Example 47A

3-Methoxy-4-(2-methyl-3-nitro-5-oxo-1,4,5,6-tetrahydro-1,6-naphthyridin-4-yl)benzonitrile

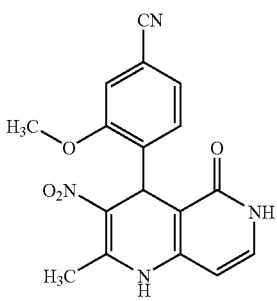

688 mg (4.26 mmol) of 4-formyl-3-methoxybenzonitrile are dissolved with 440 mg (4.26 mmol) of 1-nitroacetone, 470 mg (4.26 mmol) of 4-aminopyridin-2(1H)-one [Searls, T., McLaughlin, L. W., Tetrahedron 55, 11985-11996 (1999)] and 367 µl (6.40 mmol) of acetic acid in 10 ml of isopropanol and heated under reflux under argon for 12 h. After cooling, DMSO (5 ml) is added and the reaction solution is purified directly by preparative HPLC. 41 mg (2% of theory) of the title compound are obtained as a brown solid.

LC-MS (method 1): $R_t$=1.30 min; $[M+H]^+$=339.

Example 48A 4-(4-Cyano-2-methoxyphenyl)-2,7-dimethyl-5-oxo-1,4,5,6-tetrahydro-1,6-naphthyridine-3-carbonitrile

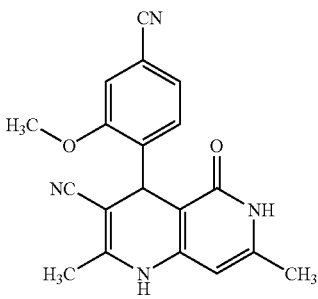

908 mg (5.64 mmol) of 4-formyl-3-methoxybenzonitrile are dissolved with 592 mg (5.64 mmol) of sodium 1-cyano-prop-1-en-2-olate, 700 mg (5.64 mmol) of 4-amino-6-methylpyridin-2(1H)-one [Bisagni, E., Hung, N. C., Synthesis, 765-766 (1984)] and 484 µl (8.46 mmol) of acetic acid in 30 ml of 2-propanol and heated at the reflux temperature under argon for 12 h. After cooling, the reaction mixture is filtered and the remaining solid is washed with diethyl ether (20 ml). 1798 mg (96% of theory) of the title compound are obtained as a white solid.

LC-MS (method 4): $R_t$=1.70 min; $[M+H]^+$ (EIpos): m/z=333

$^1$H-NMR (300 MHz, DMSO-$d_6$): δ=2.00 (s, 3H), 2.09 (s, 3H), 3.84 (s, 3H), 4.99 (s, 1H), 5.71 (s, 1H), 7.02 (d, 1H), 7.32 (dd, 1H), 7.45 (d, 1H), 9.79 (s, 1H), 11.04 (s, 1H).

Example 49A 4-(4-Cyano-2-methoxyphenyl)-2,8-dimethyl-5-oxo-1,4,5,6-tetrahydro-1,6-naphthyridine-3-carbonitrile

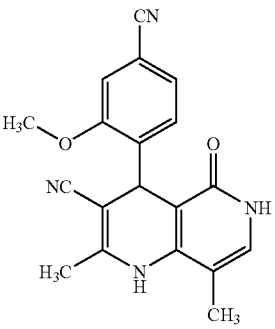

1773 mg (11.0 mmol) of 4-formyl-3-methoxybenzonitrile are dissolved with 1156 mg (11.0 mmol) of sodium 1-cyano-prop-1-en-2-olate, 1366 mg (11.0 mmol) of 4-amino-5-methylpyridin-2(1H)-one [Bisagni, E., Hung, N. C., Synthesis, 765-766 (1984)] and 945 µl (16.5 mmol) of acetic acid in 50 ml of 2-propanol and heated at the reflux temperature under argon for 20 h. After cooling, the reaction mixture is filtered and the precipitate is washed with 2-propanol and diethyl ether. The crude product is dissolved in 800 ml of dichloromethane/methanol by heating and, after addition of 500 ml of ethyl acetate, again concentrated to a volume of 50 ml. The precipitated product is filtered off and washed with ethyl acetate and diethyl ether. Drying under high vacuum results in 3.63 g (99% of theory) of the title compound in the form of yellowish crystals.

LC-MS (method 4): $R_t$=1.71 min; [M+H]$^+$ (EIpos): m/z=333.

EXEMPLARY EMBODIMENTS

Example 1

8-(3-Acetyl-5-ethoxy-2-methyl-1,4-dihydro-1,6-naphthyridin-4-yl)-2-methyl-4H-chromen-4-one

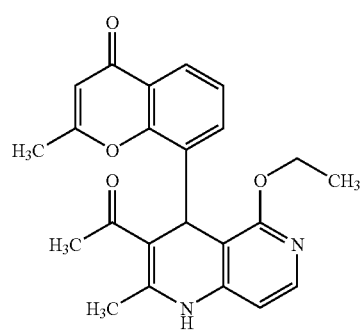 [SMILES: CCOc1nccc2c1C(c1cccc3c(=O)cc(C)oc13)C(C(C)=O)=C(C)N2]

60 mg (0.16 mmol) of 3-acetyl-2-methyl-4-(2-methyl-4-oxo-4H-chromen-8-yl)-4,6-dihydro-1,6-naphthyridin-5 (1H)-one are suspended in THF (4 ml), and 0.18 ml (0.18 mmol) of N'''-(tert-butyl)-N,N',N''-tris[tris(dimethylamino) phosphoranylidene]phosphorimide triamide (phosphazene base P$_4$-t-Bu; 1 M in hexane) is added. Then 25 µl (0.199 mmol) of ethyl trifluoromethanesulfonate are added to the dark red solution. The decolorized solution is stirred for 10 min and then mixed with methanol and concentrated. The residue is purified by preparative HPLC to result in 35 mg (54% of theory) of the title compound as a white solid.

LC-MS (method 1): $R_t$=1.59 min; [M+H]$^+$=391

$^1$H-NMR (300 MHz, DMSO-d$_6$): δ=1.03 (t, 3H), 2.14 (s, 3H), 2.34 (s, 3H), 2.39 (s, 3H), 4.06 (m, 2H), 5.63 (s, 1H), 6.21 (s, 1H), 6.53 (d, 1H), 7.32 (t, 1H), 7.63 (dd, 1H), 7.75 (m, 1H), 7.79 (dd, 1H), 9.55 (s, 1H).

Example 2

4-(3-Acetyl-5-ethoxy-2-methyl-1,4-dihydro-1,6-naphthyridin-4-yl)-3-methoxybenzonitrile

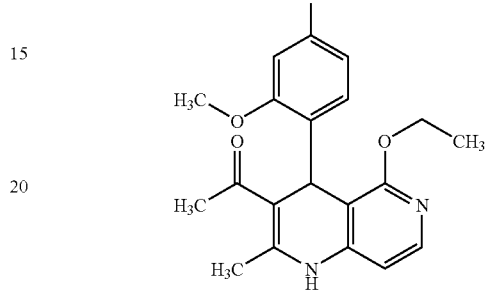

The title compound is prepared in analogy to example 1 from 2.13 g (6.37 mmol) of 4-(3-acetyl-2-methyl-5-oxo-1,4, 5,6-tetrahydro-1,6-naphthyridin-4-yl)-3-methoxybenzonitrile. 970 mg (42% of theory) of the product are obtained as a white solid.

LC-MS (method 1): $R_t$=1.84 min; [M+H]$^+$=364

$^1$H-NMR (300 MHz, DMSO-d$_6$): δ=1.14 (t, 3H), 2.10 (s, 3H), 2.26 (s, 3H), 3.83 (s, 3H), 4.11 (q, 2H), 5.48 (s, 1H), 6.50 (d, 1H), 7.21 (d, 1H), 7.28 (dd, 1H), 7.37 (d, 1H), 7.74 (d, 1H), 9.39 (s, 1H).

Example 3 ent-4-(3-Acetyl-5-ethoxy-2-methyl-1,4-dihydro-1,6-naphthyridin-4-yl)-3-methoxybenzonitrile Enantiomer A and Enantiomer B

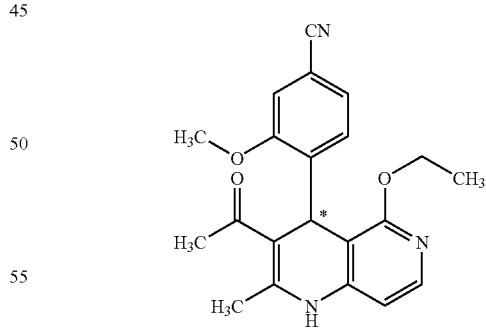

390 mg of the racemate from example 2 are separated into the enantiomers by HPLC on a chiral phase (column: 670 mm×40 mm; silica gel phase based on the chiral selector poly(N-methacryloyl-D-leucine tert-butylamide; eluent: isohexane/ethyl acetate 1:1; temperature: 24° C.; flow rate: 80 ml/min; UV detection: 270 nm).

Enantiomer A:
Yield: 192 mg
HPLC (method 9): $R_t$=2.35 min.

Enantiomer B:
Yield: 183 mg
HPLC (method 9): $R_t$=2.71 min.

Example 4

5-Ethoxy-2-methyl-4-(2-methyl-4-oxo-4H-chromen-8-yl)-1,4-dihydro-1,6-naphthyridine-3-carbo-nitrite

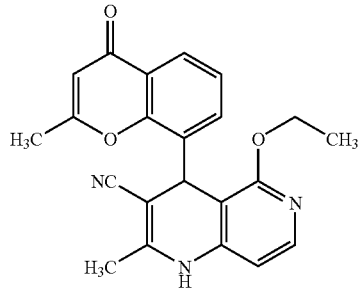

The title compound is prepared in analogy to example 1 from 71 mg (0.20 mmol) of 2-methyl-4-(2-methyl-4-oxo-4H-chromen-8-yl)-5-oxo-1,4,5,6-tetrahydro-1,6-naphthyridine-3-carbonitrile. 14 mg (18% of theory) of the product are obtained as a white solid.

LC-MS (method 3): $R_t$=1.96 min; $[M+H]^+$=374

$^1$H-NMR (300 MHz, DMSO-$d_6$): δ=0.89 (t, 3H), 2.11 (s, 3H), 2.34 (s, 3H), 3.99 (m, 2H), 5.27 (s, 1H), 6.23 (s, 1H), 6.50 (d, 1H), 7.39 (t, 1H), 7.54 (dd, 1H), 7.81 (d, 1H), 7.88 (dd, 1H), 9.87 (s, 1H).

Example 5

4-(3-Acetyl-5-ethoxy-2-methyl-1,4-dihydro-1,6-naphthyridin-4-yl)benzonitrile

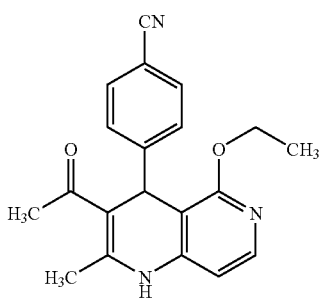 [SMILES: CCOc1nccc2c1C(c1ccc(C#N)cc1)C(C(C)=O)=C(C)N2]

The title compound is prepared in analogy to example 1 from 103 mg (0.33 mmol) of 4-(3-acetyl-2-methyl-5-oxo-1,4,5,6-tetrahydro-1,6-naphthyridin-4-yl)benzonitrile. 27 mg (24% of theory) of the product are obtained as a white solid.

LC-MS (method 4): $R_t$=2.27 min; $[M+H]^+$=334

$^1$H-NMR (300 MHz, DMSO-$d_6$): δ=1.11 (t, 3H), 2.10 (s, 3H), 2.37 (s, 3H), 3.69 (m, 1H), 3.86 (m, 1H), 5.17 (s, 1H), 5.96 (d, 1H), 7.44 (d, 2H), 7.46 (d, 1H), 7.67 (d, 2H), 9.34 (s, 1H).

Example 6

4-(3-Acetyl-5-isopropoxy-2-methyl-1,4-dihydro-1,6-naphthyridin-4-yl)benzonitrile

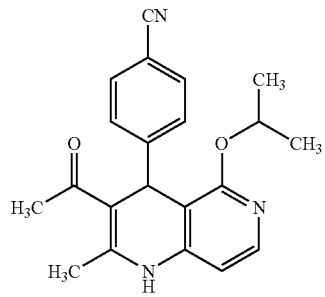 [SMILES: CC(=O)C1=C(C)Nc2ccnc(OC(C)C)c2C1c1ccc(C#N)cc1]

100 mg (0.32 mmol) of 4-(3-acetyl-2-methyl-5-oxo-1,4,5,6-tetrahydro-1,6-naphthyridin-4-yl)-benzonitrile are suspended in DMF (4 ml), and 14 mg (0.36 mmol) of sodium hydride (60% in mineral oil) are added. Then 34 μl (0.34 mmol) of 2-iodopropane are added to the dark red solution. The solution is stiffed at RT for 24 h, then mixed with methanol and purified by preparative HPLC. 18 mg (16% of theory) of the title compound are obtained as a white solid.

LC-MS (method 3): $R_t$=2.24 min; $[M+H]^+$=348

$^1$H-NMR (300 MHz, DMSO-$d_6$): δ=1.09 (d, 3H), 1.31 (d, 3H), 2.15 (s, 3H), 2.39 (s, 3H), 5.14 (m, 1H), 5.15 (s, 1H), 6.51 (d, 1H), 7.39 (d, 2H), 7.68 (d, 1H), 7.77 (d, 2H), 9.51 (s, 1H).

Example 7

8-(3-Acetyl-5-propoxy-2-methyl-1,4-dihydro-1,6-naphthyridin-4-yl)-2-methyl-4H-chromen-4-one

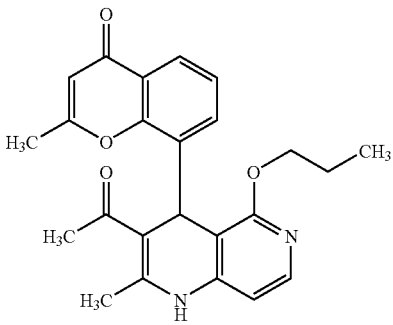 [SMILES: CCCOc1nccc2c1C(c1cccc3c(=O)cc(C)oc13)C(C(C)=O)=C(C)N2]

130 mg (0.35 mmol) of 3-acetyl-2-methyl-4-(2-methyl-4-oxo-4H-chromen-8-yl)-4,6-dihydro-1,6-naphthyridin-5 (1H)-one are suspended in THF (8 ml), and 0.39 ml (0.39 mmol) of N'''-(tert-butyl)-N,N',N''-tris[tris(dimethylamino)phosphoranylidene]phosphorimide triamide (phosphazene base $P_4$-t-Bu; 1 M in hexane) is added. Then 68 μl (0.41 mmol) of di-n-propyl sulfate are added to the dark red solution. The decolorized solution is stirred for 10 min, then mixed with methanol and concentrated. The residue is purified by preparative HPLC to result in 63 mg (43% of theory) of the title compound as a white solid.

LC-MS (method 1): $R_t$=1.63 min; [M+H]$^+$=405

$^1$H-NMR (300 MHz, DMSO-d$_6$): δ=0.80 (t, 3H), 1.56 (m, 2H), 2.14 (s, 3H), 2.34 (s, 3H), 2.38 (s, 3H), 4.04 (m, 2H), 5.62 (s, 1H), 6.21 (s, 1H), 6.53 (d, 1H), 7.32 (t, 1H), 7.63 (dd, 1H), 7.75 (m, 1H), 7.79 (dd, 1H), 9.54 (s, 1H).

Example 8

4-(3-Acetyl-5-propoxy-2-methyl-1,4-dihydro-1,6-naphthyridin-4-yl)-3-methoxybenzonitrile

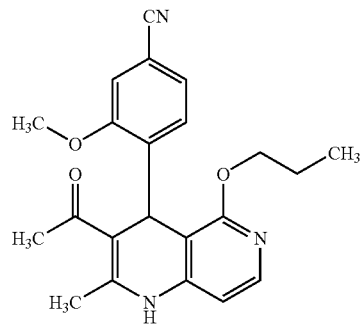 [SMILES: CCCOc1nccc2c1C(c1ccc(C#N)cc1OC)C(C(C)=O)=C(C)N2]

The title compound is prepared in analogy to example 7 from 428 mg (1.27 mmol) of 4-(3-acetyl-2-methyl-5-oxo-1,4,5,6-tetrahydro-1,6-naphthyridin-4-yl)-3-methoxybenzonitrile. 142 mg (29% of theory) of the product are obtained as a white solid.

LC-MS (method 4): $R_t$=2.27 min; [M+H]$^+$=378

$^1$H-NMR (300 MHz, DMSO-d$_6$): δ=0.81 (t, 3H), 1.56 (m, 2H), 2.11 (s, 3H), 2.25 (s, 3H), 3.82 (s, 3H), 4.04 (m, 2H), 5.49 (s, 1H), 6.51 (d, 1H), 7.20 (d, 1H), 7.27 (d, 1H), 7.37 (s, 1H), 7.75 (d, 1H), 9.42 (s, 1H).

Example 9 ent-8-[3-Acetyl-5-ethoxy-2-methyl-1,4-dihydro-1,6-naphthyridin-4-yl]-2-methyl-4H-chromen-4-one

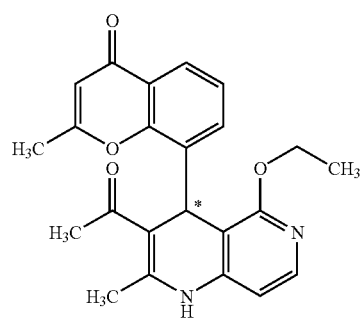 [SMILES: CCOc1nccc2c1C(c1cccc3c(=O)cc(C)oc13)C(C(C)=O)=C(C)N2]

940 mg (2.59 mmol) of ent-3-acetyl-2-methyl-4-(2-methyl-4-oxo-4H-chromen-8-yl)-4,6-dihydro-1,6-naphthyridin-5(1H)-one (example 23A) are suspended under an argon atmosphere in dichloromethane (30 ml), 985 mg (5.18 mmol) of triethyloxonium tetrafluoroborate are added, and the mixture is stirred at RT for 2 h. The reaction mixture is then mixed with methanol and concentrated. The residue is purified by preparative HPLC to result in 300 mg (30% of theory) of the enantiomerically pure title compound as a white solid.

HPLC (method 10): $R_t$=3.20 min

LC-MS (method 1): $R_t$=1.59 min; [M+H]$^+$=391

$^1$H-NMR (300 MHz, DMSO-d$_6$): δ=1.03 (t, 3H), 2.14 (s, 3H), 2.34 (s, 3H), 2.39 (s, 3H), 4.06 (m, 2H), 5.63 (s, 1H), 6.21 (s, 1H), 6.53 (d, 1H), 7.32 (t, 1H), 7.63 (dd, 1H), 7.75 (m, 1H), 7.79 (dd, 1H), 9.55 (s, 1H).

Example 10

3-Acetyl-2-methyl-4-(2-methyl-4-oxo-4H-chromen-8-yl)-1,4-dihydro-1,6-naphthyridin-5-yl ethane-sulfonate

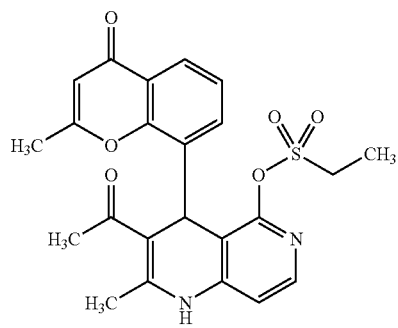 [SMILES: CCS(=O)(=O)Oc1nccc2c1C(c1cccc3c(=O)cc(C)oc13)C(C(C)=O)=C(C)N2]

133 mg (0.367 mmol) of 3-acetyl-2-methyl-4-(2-methyl-4-oxo-4H-chromen-8-yl)-4,6-dihydro-1,6-naphthyridin-5(1H)-one are suspended in pyridine (5 ml), and 700 (0.73 mmol) of ethanesulfonyl chloride are added. The suspension is stirred at RT for 3 h (during which the precursor dissolves), and then mixed with methanol and concentrated. The residue is purified by preparative HPLC to result in 63 mg (43% of theory) of the title compound as a white solid.

LC-MS (method 4): $R_t$=1.88 min; [M+H]$^+$=455

$^1$H-NMR (300 MHz, DMSO-d$_6$): δ=1.18 (t, 3H), 2.18 (s, 3H), 2.36 (s, 3H), 2.39 (s, 3H), 3.69 (m, 2H), 5.76 (s, 1H), 6.19 (s, 1H), 6.91 (d, 1H), 7.32 (t, 1H), 7.62 (dd, 1H), 7.81 (dd, 1H), 7.95 (m, 1H), 9.94 (s, 1H).

Example 11

3-Acetyl-2-methyl-4-(2-methyl-4-oxo-4H-chromen-8-yl)-1,4-dihydro-1,6-naphthyridin-5-yl methanesulfonate

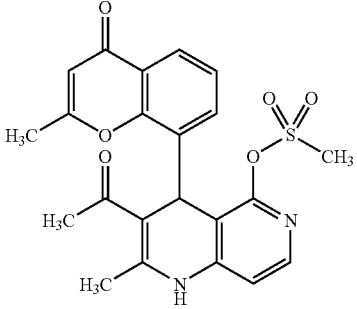

The title compound is prepared in analogy to example 10 from 50 mg (0.13 mmol) of 3-acetyl-2-methyl-4-(2-methyl-4-oxo-4H-chromen-8-yl)-4,6-dihydro-1,6-naphthyridin-5(1H)-one and 12 μl (0.15 mmol) of methanesulfonyl chloride. 10.4 mg (15% of theory) of the product are obtained as a pale yellow solid.

LC-MS (method 2): $R_t$=1.84 min; [M+H]$^+$=425

$^1$H-NMR (300 MHz, DMSO-d$_6$): δ=2.18 (s, 3H), 2.36 (s, 3H), 2.39 (s, 3H), 3.52 (s, 3H), 5.74 (s, 1H), 6.19 (s, 1H), 6.92 (d, 1H), 7.32 (t, 1H), 7.62 (dd, 1H), 7.81 (dd, 1H), 7.97 (d, 1H), 9.96 (s, 1H).

Example 12

3-Acetyl-2-methyl-4-(2-methyl-4-oxo-4H-chromen-8-yl)-1,4-dihydro-1,6-naphthyridin-5-yl propanesulfonate

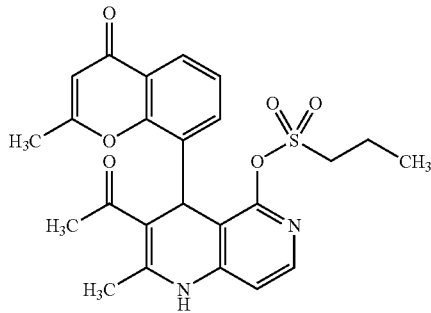 [SMILES: CCCS(=O)(=O)Oc1nccc2c1C(c1cccc3c(=O)cc(C)oc13)C(C(C)=O)=C(C)N2]

The title compound is prepared in analogy to example 10 from 50 mg (0.13 mmol) of 3-acetyl-2-methyl-4-(2-methyl-4-oxo-4H-chromen-8-yl)-4,6-dihydro-1,6-naphthyridin-5(1H)-one and 17 μl (0.15 mmol) of propanesulfonyl chloride. 46 mg (71% of theory) of the product are obtained as a pale yellow solid.

LC-MS (method 3): $R_t$=1.95 min; [M+H]$^+$=469

$^1$H-NMR (300 MHz, DMSO-d$_6$): δ=0.89 (t, 3H), 1.64 (m, 2H), 2.18 (s, 3H), 2.36 (s, 3H), 2.38 (s, 3H), 3.68 (m, 2H), 5.76 (s, 1H), 6.19 (s, 1H), 6.90 (d, 1H), 7.32 (t, 1H), 7.62 (dd, 1H), 7.81 (dd, 1H), 7.96 (d, 1H), 9.93 (s, 1H).

Example 13

3-Acetyl-2-methyl-4-(2-methyl-4-oxo-4H-chromen-8-yl)-1,4-dihydro-1,6-naphthyridin-5-yl butane-sulfonate

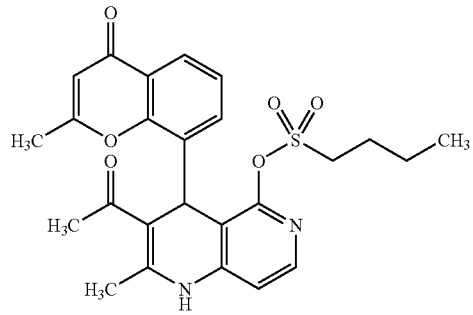 [SMILES: CCCCS(=O)(=O)Oc1nccc2c1C(c1cccc3c(=O)cc(C)oc13)C(C(C)=O)=C(C)N2]

The title compound is prepared in analogy to example 10 from 50 mg (0.13 mmol) of 3-acetyl-2-methyl-4-(2-methyl-4-oxo-4H-chromen-8-yl)-4,6-dihydro-1,6-naphthyridin-5(1H)-one and 24 mg (0.15 mmol) of butanesulfonyl chloride. 48 mg (72% of theory) of the product are obtained as a pale yellow solid.

LC-MS (method 3): $R_t$=2.09 min; [M+H]$^+$=483

$^1$H-NMR (400 MHz, DMSO-d$_6$): δ=0.76 (t, 3H), 1.27 (m, 2H), 1.53 (m, 2H), 2.18 (s, 3H), 2.36 (s, 3H), 2.39 (s, 3H), 3.70 (t, 2H), 5.76 (s, 1H), 6.19 (s, 1H), 6.90 (d, 1H), 7.32 (t, 1H), 7.62 (dd, 1H), 7.81 (dd, 1H), 7.95 (d, 1H), 9.94 (s, 1H).

Example 14

3-Acetyl-2-methyl-4-(2-methyl-4-oxo-4H-chromen-8-yl)-1,4-dihydro-1,6-naphthyridin-5-yl cyclo-propanesulfonate

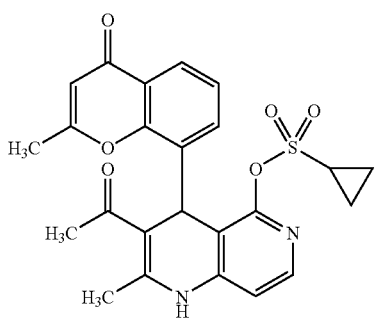 [SMILES: CC(=O)C1=C(C)Nc2ccnc(OS(=O)(=O)C3CC3)c2C1c1cccc2c(=O)cc(C)oc12]

The title compound is prepared in analogy to example 10 from 50 mg (0.13 mmol) of 3-acetyl-2-methyl-4-(2-methyl-4-oxo-4H-chromen-8-yl)-4,6-dihydro-1,6-naphthyridin-5(1H)-one and 22 mg (0.15 mmol) of cyclopropanesulfonyl chloride. 54 mg (84% of theory) of the product are obtained as a pale yellow solid.

LC-MS (method 1): $R_t$=1.65 min; [M+H]$^+$=467.

Example 15

3-Acetyl-2-methyl-4-(2-methyl-4-oxo-4H-chromen-8-yl)-1,4-dihydro-1,6-naphthyridin-5-yl thiophene-2-sulfonate

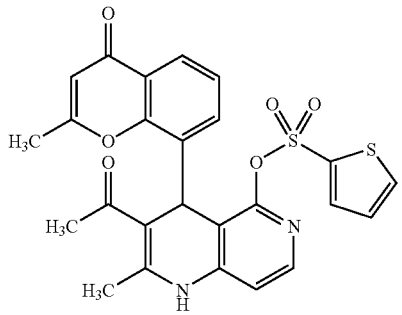 [SMILES: CC(=O)C1=C(C)Nc2ccnc(OS(=O)(=O)c3cccs3)c2C1c1cccc2c(=O)cc(C)oc12]

The title compound is prepared in analogy to example 10 from 50 mg (0.13 mmol) of 3-acetyl-2-methyl-4-(2-methyl-4-oxo-4H-chromen-8-yl)-4,6-dihydro-1,6-naphthyridin-5

(1H)-one and 28 mg (0.15 mmol) of thiophene-2-sulfonyl chloride. 57 mg (81% of theory) of the product are obtained as a pale yellow solid.

LC-MS (method 1): $R_t$=1.78 min; [M+H]$^+$=509

$^1$H-NMR (400 MHz, DMSO-d$_6$): δ=2.17 (s, 3H), 2.35 (s, 3H), 2.39 (s, 3H), 5.72 (s, 1H), 6.20 (s, 1H), 6.86 (d, 1H), 7.18 (dd, 1H), 7.30 (t, 1H), 7.52 (dd, 1H), 7.74 (dd, 1H), 7.83 (dd, 1H), 7.86 (d, 1H), 8.12 (dd, 1H), 9.92 (s, 1H).

Example 16

3-Acetyl-4-(4-cyano-2-methoxyphenyl)-2-methyl-1,4-dihydro-1,6-naphthyridin-5-yl ethanesulfonate

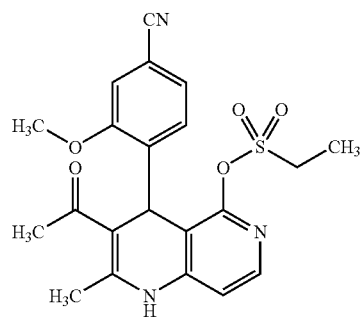 [SMILES: CCS(=O)(=O)Oc1nccc2c1C(c1ccc(C#N)cc1OC)C(C(C)=O)=C(C)N2]

The title compound is prepared in analogy to example 10 starting from 5.05 g (15.05 mmol) of 4-(3-acetyl-2-methyl-5-oxo-1,4,5,6-tetrahydro-1,6-naphthyridin-4-yl)-3-methoxybenzonitrile. 4.97 g (77% of theory) of the product are obtained as a pale yellow solid.

LC-MS (method 3): $R_t$=2.03 min; [M+H]$^+$=428

$^1$H-NMR (300 MHz, DMSO-d$_6$): δ=1.28 (t, 3H), 2.15 (s, 3H), 2.28 (s, 3H), 3.70 (m, 2H), 3.79 (s, 3H), 5.60 (s, 1H), 6.87 (d, 1H), 7.20 (d, 1H), 7.29 (dd, 1H), 7.40 (d, 1H), 7.94 (d, 1H), 9.80 (s, 1H).

Example 17 ent-3-Acetyl-4-(4-cyano-2-methoxyphenyl)-2-methyl-1,4-dihydro-1,6-naphthyridin-5-yl ethane-sulfonate Enantiomer A and Enantiomer B

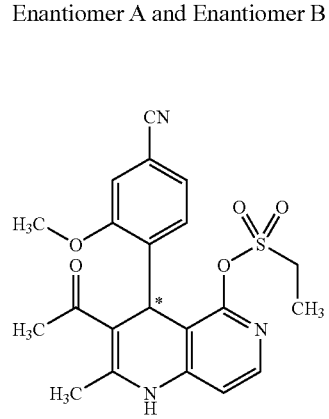

1.8 g of the racemate from example 16 are separated into the enantiomers by HPLC on a chiral phase (column: 670 mm×40 mm; silica gel phase based on the chiral selector poly(N-methacryloyl-D-leucine tert-butylamide; eluent: isohexane/ethyl acetate 1:1; temperature: 24° C.; flow rate: 80 ml/min; UV detection: 270 nm).

Enantiomer A:
  Yield: 870 mg
  HPLC (method 9): $R_t$=3.12 min.

Enantiomer B:
  Yield: 857 mg
  HPLC (method 9): $R_t$=4.88 min.

Example 18

3-Acetyl-2-methyl-4-(2-methyl-4-oxo-4H-chromen-8-yl)-1,4-dihydro-1,6-naphthyridin-5-yl trifluoromethanesulfonate

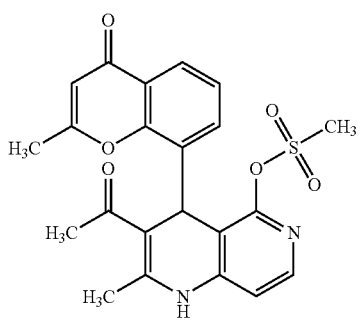

134 mg (0.37 mmol) of 3-acetyl-2-methyl-4-(2-methyl-4-oxo-4H-chromen-8-yl)-4,6-dihydro-1,6-naphthyridin-5(1H)-one are introduced into 5 ml of pyridine, 80 μl (0.75 mmol) of trifluoromethanesulfonic anhydride are added, and the mixture is stirred at room temperature for 1 h. The mixture is then concentrated and the residue is purified by preparative HPLC (eluent: acetonitrile/water with 0.1% formic acid gradient 20:80→95:5). 129 mg (70% of theory) of the title compound are obtained.

LC-MS (method 4): $R_t$=2.40 min; MS (EIpos): m/z=495 [M+H]$^+$

¹H-NMR (300 MHz, DMSO-d₆): δ=2.22 (s, 3H), 2.25 (s, 3H), 2.37 (s, 3H), 5.75 (s, 1H), 6.20 (s, 1H), 7.03 (d, 1H), 7.36 (t, 1H), 7.64 (dd, 1H), 7.85 (dd, 1H), 8.00 (d, 1H), 10.13 (s, 1H).

Example 19

3-Acetyl-4-(4-cyano-2-methoxyphenyl)-2-methyl-1,4-dihydro-1,6-naphthyridin-5-yl trifluoro-methanesulfonate

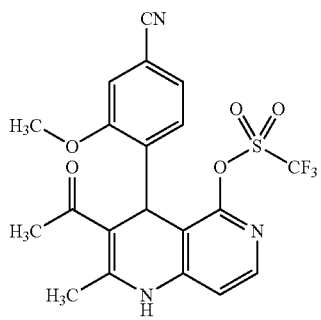 [SMILES: COc1cc(C#N)ccc1C1C(C(C)=O)=C(C)Nc2ccnc(OS(=O)(=O)C(F)(F)F)c21]

The title compound is prepared in analogy to example 18 from 75 mg (0.224 mmol) of 4-(3-acetyl-2-methyl-5-oxo-1,4,5,6-tetrahydro-1,6-naphthyridin-4-yl)-3-methoxybenzonitrile. 61 mg (58% of theory) of the product are obtained as a pale yellow solid.

LC-MS (method 3): $R_t$=2.47 min; [M+H]⁺=468

¹H-NMR (300 MHz, DMSO-d₆): δ=2.17 (s, 3H), 2.31 (s, 3H), 3.80 (s, 3H), 5.60 (s, 1H), 7.00 (d, 1H), 7.23 (d, 1H), 7.32 (dd, 1H), 7.44 (d, 1H), 7.99 (d, 1H), 10.02 (s, 1H).

Example 20

3-Acetyl-4-(4-cyanophenyl)-2-methyl-1,4-dihydro-1,6-naphthyridin-5-yl trifluoromethanesulfonate

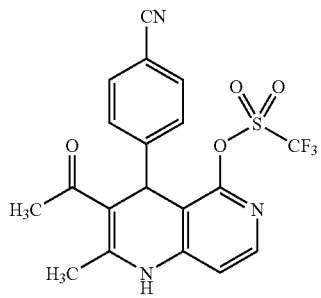 [SMILES: CC(=O)C1=C(C)Nc2ccnc(OS(=O)(=O)C(F)(F)F)c2C1c1ccc(C#N)cc1]

The title compound is prepared in analogy to example 18 from 107 mg (0.35 mmol) of 4-(3-acetyl-2-methyl-5-oxo-1,4,5,6-tetrahydro-1,6-naphthyridin-4-yl)benzonitrile. 120 mg (58% of theory) of the product are obtained as a white solid.

LC-MS (method 3): $R_t$=2.42 min; [M+H]⁺=438

¹H-NMR (300 MHz, DMSO-d₆): δ=2.25 (s, 3H), 2.42 (s, 3H), 5.31 (s, 1H), 7.07 (d, 1H), 7.35 (d, 2H), 7.75 (d, 2H), 8.05 (d, 1H), 10.14 (s, 1H).

Example 21

4-(3-Acetyl-5-ethoxy-2-methyl-1,4-dihydro-1,6-naphthyridin-4-yl)-3-(trifluoromethoxy)benzonitrile

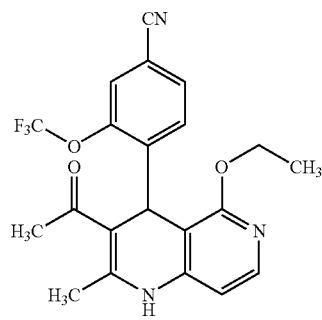 [SMILES: CCOc1nccc2c1C(c1ccc(C#N)cc1OC(F)(F)F)C(C(C)=O)=C(C)N2]

2.40 g (6.16 mmol) of 4-(3-acetyl-2-methyl-5-oxo-1,4,5,6-tetrahydro-1,6-naphthyridin-4-yl)-3-(trifluoromethoxy)benzonitrile (example 10A) are suspended in 5 ml of abs. THF and, after addition of 6.78 ml (6.78 mmol) of N'''-(tert-butyl)-N,N',N''-tris[tris(dimethylamino)-phosphoranylidene]phosphorimide triamide (phosphazene base P₄-t-Bu; 1 M in hexane), stirred for 5 min. Then 1.32 g (7.40 mmol) of ethyl trifluoromethanesulfonate are added. After stirring for a further 5 min, the mixture is hydrolyzed with saturated sodium bicarbonate solution and extracted twice with ethyl acetate. The combined organic phases are washed with saturated sodium chloride solution, dried with sodium sulfate and then concentrated in a rotary evaporator. The residue is purified by column chromatography (silica gel, mobile phase: cyclohexane/ethyl acetate 3:7). Recrystallization from acetonitrile finally affords 745 mg (29% of theory) of the title compound.

LC-MS (method 1): $R_t$=2.18 min; MS (EIpos): m/z=418 [M+H]⁺

$^1$H-NMR (300 MHz, DMSO-d$_6$): δ=1.13 (t, 3H), 2.17 (s, 3H), 2.34 (s, 3H), 4.12 (m, 2H), 5.44 (s, 1H), 6.53 (d, 1H), 7.55 (d, 1H), 7.65-7.71 (m, 2H), 7.78 (d, 1H), 9.58 (s, 1H).

Example 22 ent-4-(3-Acetyl-5-ethoxy-2-methyl-1,4-dihydro-1,6-naphthyridin-4-yl)-3-(trifluoromethoxy)benzonitrile Enantiomer A and Enantiomer B

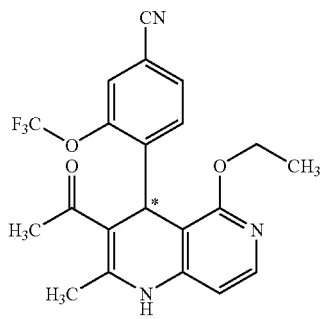

700 mg of the racemate from example 21 are separated into the enantiomers by HPLC on a chiral phase (column: 670 mm×40 mm; silica gel phase based on the chiral selector poly(N-methacryloyl-D-leucine tert-butylamide; eluent: isohexane/ethyl acetate 1:1; temperature: 24° C.; flow rate: 80 ml/min; UV detection: 270 nm).
Enantiomer A:
 Yield: 276 mg
 HPLC (method 9): R$_t$=2.18 min.
Enantiomer B:
 Yield: 283 mg
 HPLC (method 9): R$_t$=3.41 min.

Example 23

3-Cyano-2-methyl-4-(2-methyl-4-oxo-4H-chromen-8-yl)-1,4-dihydro-1,6-naphthyridin-5-yl trifluoromethanesulfonate

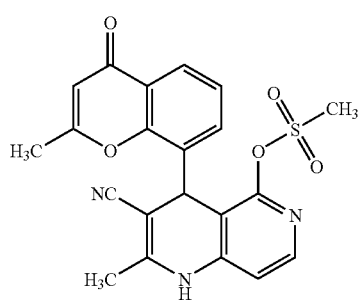

100 mg (0.290 mmol) of 2-methyl-4-(2-methyl-4-oxo-4H-chromen-8-yl)-5-oxo-1,4,5,6-tetrahydro-1,6-naphthyridine-3-carbonitrile are introduced into 5 ml of pyridine, 163 mg (0.579 mmol) of trifluoromethanesulfonic anhydride are added, and the mixture is stirred at room temperature for 1 h. The mixture is concentrated and the residue is purified by preparative HPLC (eluent: acetonitrile/water with 0.1% formic acid; gradient 20:80→95:5). 80 mg (58% of theory) of the title compound are obtained.
 LC-MS (method 4): R$_t$=2.42 min; MS (EIpos): m/z=478 [M+H]$^+$
 $^1$H-NMR (300 MHz, DMSO-d$_6$): δ=2.14 (s, 3H), 2.29 (s, 3H), 5.50 (s, 1H), 6.25 (s, 1H), 6.99 (d, 1H), 7.45 (t, 1H), 7.57 (dd, 1H), 7.95 (dd, 1H), 8.07 (d, 1H), 10.44 (s, 1H).

Example 24

4-(3-Acetyl-5-ethoxy-2-methyl-1,4-dihydro-1,6-naphthyridin-4-yl)-3-ethylbenzonitrile

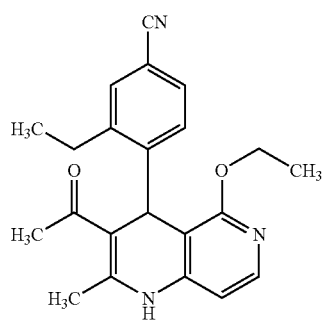 [SMILES: CCOc1nccc2c1C(c1ccc(C#N)cc1CC)C(C(C)=O)=C(C)N2]

275 mg (0.82 mmol) of 4-(3-acetyl-2-methyl-5-oxo-1,4,5,6-tetrahydro-1,6-naphthyridin-4-yl)-3-ethylbenzonitrile are suspended under an argon atmosphere in dichloromethane (10 ml), 313 mg (1.65 mmol) of triethyloxonium tetrafluoroborate are added, and the mixture is stirred at RT for 12 h. The reaction mixture is then mixed with methanol and concentrated. The residue is purified by preparative HPLC to result in 152 mg (50% of theory) of the title compound as a white solid.
 LC-MS (method 4): R$_t$=2.33 min; [M+H]$^+$=362
 $^1$H-NMR (300 MHz, CDCl$_3$): δ=1.15 (t, 3H), 1.27 (t, 3H), 2.19 (s, 3H), 2.37 (s, 3H), 3.13 (m, 1H), 3.30 (m, 1H), 4.16 (m, 2H), 5.38 (s, 1H), 6.56 (d, 1H), 7.28 (d, 1H), 7.45 (dd, 1H), 7.51 (d, 1H), 7.61 (d, 1H), 9.50 (s, 1H).

Example 25

4-(4-Cyano-2-methoxyphenyl)-5-ethoxy-2-methyl-1,4-dihydro-1,6-naphthyridine-3-carbonitrile

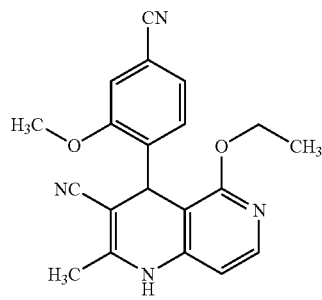

505 mg (1.58 mmol) of 4-(4-cyano-2-methoxyphenyl)-2-methyl-5-oxo-1,4,5,6-tetrahydro-1,6-naphthyridine-3-carbonitrile are suspended in THF (20 ml), and 1.9 ml (1.9 mmol) of N'''-(tert-butyl)-N,N',N''-tris[tris(dimethylamino)

phosphoranylidene]phosphorimide triamide (phosphazene base P₄-t-Bu; 1 M in hexane) are added. Then 240 µl (1.9 mmol) of ethyl trifluoromethanesulfonate are added to the dark red solution. The decolorized solution is stirred for a further 10 min and then mixed with methanol and concentrated. The residue is purified by preparative HPLC to result in 124 mg (21% of theory) of the title compound as a white solid.

LC-MS (method 1): $R_t$=1.98 min; $[M+H]^+$=347

¹H-NMR (300 MHz, DMSO-$d_6$): δ=0.96 (t, 3H), 2.05 (s, 3H), 3.83 (s, 3H), 4.02 (m, 2H), 5.17 (s, 1H), 6.47 (d, 1H), 7.08 (d, 1H), 7.33 (dd, 1H), 7.47 (d, 1H), 7.80 (d, 1H), 9.72 (s, 1H).

Example 26 ent-4-(4-Cyano-2-methoxyphenyl)-5-ethoxy-2-methyl-1,4-dihydro-1,6-naphthyridine-3-carbonitrile Enantiomer A and Enantiomer B

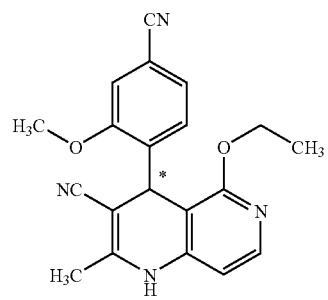

1 g of the racemate from example 25 are separated into the enantiomers by HPLC on a chiral phase (column: 630 mm×30 mm; silica gel phase based on the chiral selector poly(N-methacryloyl-D-leucine tert-butylamide; eluent: isohexane/ethyl acetate 1:1; temperature: 24° C.; flow rate: 25 ml/min; UV detection: 260 nm).

Enantiomer A:
Yield: 427 mg
HPLC (method 9): $R_t$=5.72 min.

Enantiomer B:
Yield: 494 mg
HPLC (method 9): $R_t$=7.32 min.

Example 27

1-[5-Ethoxy-2-methyl-4-[4-nitro-2-(trifluoromethyl)phenyl]-1,4-dihydro-1,6-naphthyridin-3-yl]-ethanone

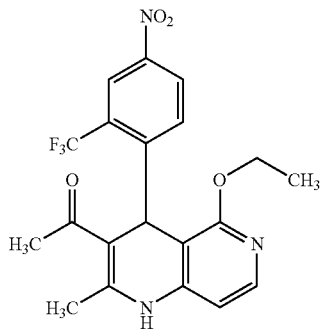 [SMILES: CCOc1nccc2c1C(c1ccc([N+](=O)[O-])cc1C(F)(F)F)C(C(C)=O)=C(C)N2]

976 mg (2.48 mmol) of 3-acetyl-2-methyl-4-[4-nitro-2-(trifluoromethyl)phenyl]-4,6-dihydro-1,6-naphthyridin-5(1H)-one are suspended in THF (60 ml), and 3 ml (3 mmol) of N'''-(tert-butyl)-N,N',N''-tris[tris(dimethylamino)phosphoranylidene]phosphorimide triamide (phosphazene base P₄-t-Bu; 1 M in hexane) are added. Then 389 µl (2.97 mmol) of ethyl trifluoromethanesulfonate are added to the dark red solution. The decolorized solution is stirred for a further 10 min and then mixed with methanol and concentrated. The residue is purified by preparative HPLC to result in 240 mg (23% of theory) of the title compound as a white solid.

LC-MS (method 4): $R_t$=2.47 min; $[M+H]^+$=422

¹H-NMR (300 MHz, DMSO-$d_6$): δ=1.07 (t, 3H), 2.20 (s, 3H), 2.37 (s, 3H), 4.15 (m, 2H), 5.74 (s, 1H), 6.57 (d, 1H), 7.59 (d, 1H), 7.80 (d, 1H), 8.23 (d, 1H), 8.28 (dd, 1H), 9.57 (s, 1H).

Example 28

4-(3-Acetyl-5-ethoxy-2-methyl-1,4-dihydro-1,6-naphthyridin-4-yl)-3-fluorobenzonitrile

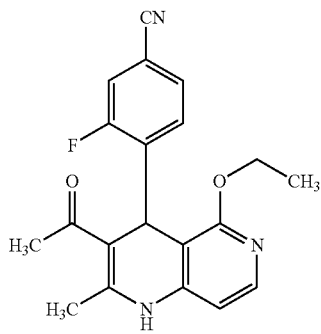 [SMILES: CCOc1nccc2c1C(c1ccc(C#N)cc1Cl)C(C(C)=O)=C(C)N2]

18 mg (0.056 mmol) of 4-(3-acetyl-2-methyl-5-oxo-1,4,5,6-tetrahydro-1,6-naphthyridin-4-yl)-3-fluorobenzonitrile are dissolved under an argon atmosphere in 5 ml abs. dichloromethane, and 21.2 mg (0.111 mmol) of triethyloxonium tetrafluoroborate are added. After a reaction time of two hours at room temperature (reaction checked by HPLC), the mixture is mixed with 5 ml of methanol and 0.5 ml of water and again stirred for 2 h. It is then diluted with 10 ml of water and extracted three times with dichloromethane. The combined organic phases are dried with sodium sulfate, and the solvent is removed in a rotary evaporator. The residue is purified by column chromatography (silica gel, mobile phase: cyclohexane/ethyl acetate 3:7). 7 mg (35.4% of theory) of the title compound are obtained.

LC-MS (method 3): $R_t$=2.10 min; [M+H]$^+$ (EIpos): m/z=352

$^1$H-NMR (300 MHz, DMSO-d$_6$): δ=1.17 (t, 3H), 2.15 (s, 3H), 2.36 (s, 3H), 4.13 (m, 2H), 5.40 (s, 1H), 6.52 (d, 1H), 7.38 (t, 1H), 7.53 (dd, 1H), 7.68 (dd, 1H), 7.77 (d, 1H), 9.54 (s, 1H).

Example 29

4-(3-Acetyl-5-ethoxy-2-methyl-1,4-dihydro-1,6-naphthyridin-4-yl)-3-chlorobenzonitrile

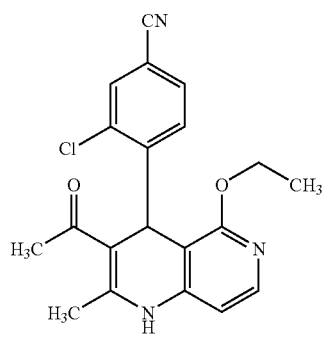

245 mg (0.721 mmol) of 4-(3-acetyl-2-methyl-5-oxo-1,4,5,6-tetrahydro-1,6-naphthyridin-4-yl)-3-chlorobenzonitrile are dissolved under an argon atmosphere in 15 ml of abs. dichloromethane, and 273 mg (1.442 mmol) of triethyloxonium tetrafluoroborate are added. After a reaction time of two hours at room temperature (reaction checked by HPLC), the mixture is mixed with 5 ml of methanol and 0.5 ml of water and stirred for a further 2 h. It is then diluted with 20 ml of water and extracted three times with dichloromethane. The combined organic phases are dried with sodium sulfate, and the solvent is removed in a rotary evaporator. The residue is purified by preparative HPLC (eluent: acetonitrile/water with 0.1% formic acid, gradient 20:80→95:5). 127 mg (47.9% of theory) of the title compound are obtained.

LC-MS (method 3): $R_t$=2.20 min; [M+H]$^+$ (EIpos): m/z=368

$^1$H-NMR (300 MHz, DMSO-d$_6$): δ=1.17 (t, 3H), 2.17 (s, 3H), 2.34 (s, 3H), 4.16 (m, 2H), 5.52 (s, 1H), 6.54 (d, 1H), 7.44 (d, 1H), 7.66 (dd, 1H), 7.78 (d, 1H), 7.87 (d, 1H), 9.57 (s, 1H).

Example 30

4-(3-Acetyl-5-ethoxy-2-methyl-1,4-dihydro-1,6-naphthyridin-4-yl)-3-methylbenzonitrile

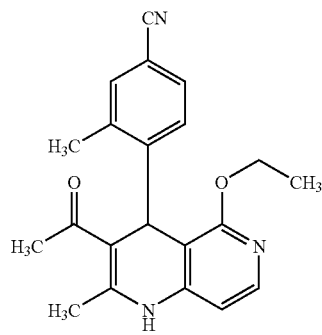

150 mg (0.470 mmol) of 4-(3-acetyl-2-methyl-5-oxo-1,4,5,6-tetrahydro-1,6-naphthyridin-4-yl)-3-methylbenzonitrile are dissolved under an argon atmosphere in 10 ml of abs. dichloromethane, and 178 mg (0.939 mmol) of triethyloxonium tetrafluoroborate are added. After a reaction time of two hours at room temperature (reaction checked by HPLC), the mixture is mixed with 5 ml of methanol and 0.5 ml of water and again stirred for 2 h. It is then diluted with 20 ml of water and extracted three times with dichloromethane. The combined organic phases are dried with sodium sulfate, and the solvent is removed in a rotary evaporator. The residue is purified by preparative HPLC (eluent: acetonitrile/water with 0.1% formic acid, gradient 20:80→95:5). 110 mg (67.4% of theory) of the title compound are obtained.

LC-MS (method 4): $R_t$=2.20 min; [M+H]$^+$ (EIpos): m/z=348

$^1$H-NMR (300 MHz, DMSO-d$_6$): δ=1.18 (t, 3H), 2.20 (s, 3H), 2.38 (s, 3H), 2.73 (s, 3H), 4.17 (m, 2H), 5.27 (s, 1H), 6.56 (d, 1H), 7.25 (d, 1H), 7.45 (dd, 1H), 7.49 (s, 1H), 7.77 (d, 1H), 9.50 (s, 1H).

Example 31

4-(3-Acetyl-5-ethoxy-2-methyl-1,4-dihydro-1,6-naphthyridin-4-yl)-3-(trifluoromethyl)benzonitrile

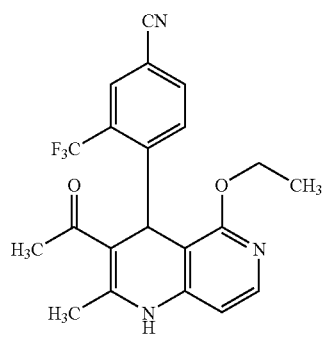 [SMILES: CCOc1nccc2c1C(c1ccc(C#N)cc1C(F)(F)F)C(C(C)=O)=C(C)N2]

50 mg (0.134 mmol) of 4-(3-acetyl-2-methyl-5-oxo-1,4,5,6-tetrahydro-1,6-naphthyridin-4-yl)-3-(trifluoromethyl)benzonitrile are dissolved under an argon atmosphere in 5 ml of abs. dichloromethane, and 50.9 mg (0.268 mmol) of triethyloxonium tetrafluoroborate are added. After a reaction time of two hours at room temperature (reaction checked by HPLC), the mixture is mixed with 5 ml of methanol and 0.5 ml of water and again stirred for 2 h. It is then diluted with 20 ml of water and extracted three times with dichloromethane. The combined organic phases are dried with sodium sulfate, and the solvent is removed in a rotary evaporator. The residue is purified by preparative HPLC (eluent: acetonitrile/water with 0.1% formic acid, gradient 20:80→95:5). 23 mg (42.8% of theory) of the title compound are obtained.

LC-MS (method 1): $R_t$=2.12 min; $[M+H]^+$ (EIpos): m/z=402

$^1$H-NMR (300 MHz, DMSO-$d_6$): δ=1.06 (t, 3H), 2.19 (s, 3H), 2.35 (s, 3H), 4.15 (m, 2H), 5.69 (s, 1H), 6.56 (d, 1H), 7.48 (d, 1H), 7.80 (d, 1H), 7.90 (dd, 1H), 8.05 (d, 1H), 9.54 (s, 1H).

Example 32

4-(3-Acetyl-5-ethoxy-2-methyl-1,4-dihydro-1,6-naphthyridin-4-yl)-1-naphthonitrile

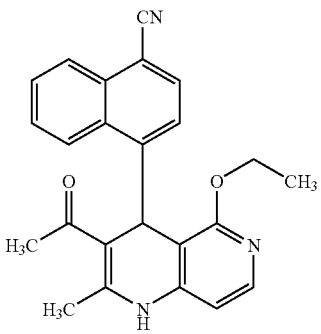 [SMILES: CCOc1nccc2c1C(c1ccc(C#N)c3ccccc13)C(C(C)=O)=C(C)N2]

93 mg (0.262 mmol) of 4-(3-acetyl-2-methyl-5-oxo-1,4,5,6-tetrahydro-1,6-naphthyridin-4-yl)-1-naphthonitrile are dissolved under an argon atmosphere in 5 ml of abs. dichloromethane, and 99.4 mg (0.268 mmol) of triethyloxonium tetrafluoroborate are added. After a reaction time of two hours at room temperature (reaction checked by HPLC), the mixture is mixed with 5 ml of methanol and 0.5 ml of water and again stirred for 2 h. It is then diluted with 20 ml of water and extracted three times with dichloromethane. The combined organic phases are dried with sodium sulfate, and the solvent is removed in a rotary evaporator. The residue is purified by preparative HPLC (eluent: acetonitrile/water with 0.1% formic acid, gradient 20:80→95:5). 60 mg (59.8% of theory) of the title compound are obtained.

LC-MS (method 4): $R_t$=2.35 min; $[M+H]^+$ (EIpos): m/z=384

$^1$H-NMR (300 MHz, DMSO-$d_6$): δ=0.87 (t, 3H), 2.10 (s, 3H), 2.43 (s, 3H), 3.88 (m, 1H), 4.02 (m, 1H), 6.05 (s, 1H), 6.59 (d, 1H), 7.49 (d, 1H), 7.74 (d, 1H), 7.78 (m, 2H), 8.01 (d, 1H), 8.06 (m, 1H), 8.05 (m, 1H), 9.59 (s, 1H).

Example 33

4-(4-Cyano-2-methoxyphenyl)-5-ethoxy-2-(trifluoromethyl)-1,4-dihydro-1,6-naphthyridine-3-carbonitrile

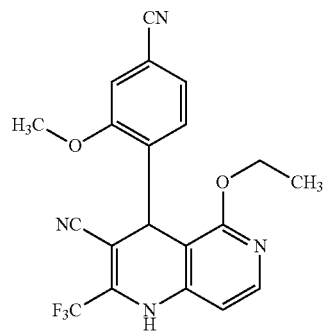 [SMILES: CCOc1nccc2c1C(c1ccc(C#N)cc1OC)C(C#N)=C(C(F)(F)F)N2]

390 mg (1.05 mmol) of 4-(4-cyano-2-methoxyphenyl)-5-oxo-2-(trifluoromethyl)-1,4,5,6-tetrahydro-1,6-naphthyridine-3-carbonitrile and 398 mg of triethyloxonium tetrafluoroborate (2.1 mmol) are mixed under a dry argon atmosphere. After addition of dichloromethane (32 ml), the suspension is stirred until a solution is obtained (about 2 h), and then mixed with methanol and concentrated. The residue is purified by preparative HPLC to result in 250 mg (59% of theory) of the title compound as a white solid.

LC-MS (method 1): $R_t$=2.29 min; $[M+H]^+$=401

$^1$H-NMR (300 MHz, DMSO-$d_6$): δ=1.02 (t, 3H), 3.81 (s, 3H), 4.05 (m, 2H), 5.28 (s, 1H), 6.72 (d, 1H), 7.28 (d, 1H), 7.40 (dd, 1H), 7.52 (d, 1H), 7.87 (d, 1H), 10.48 (s, 1H).

Example 34

4-(5-Ethoxy-2-methyl-3-nitro-1,4-dihydro-1,6-naphthyridin-4-yl)-3-methoxybenzonitrile

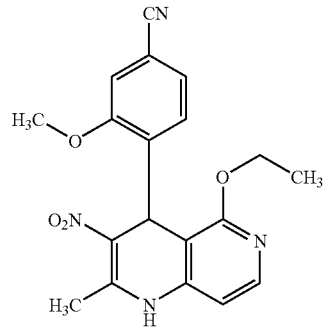 [SMILES: CCOc1nccc2c1C(c1ccc(C#N)cc1OC)C([N+](=O)[O-])=C(C)N2]

40 mg (0.11 mmol) of 3-methoxy-4-(2-methyl-3-nitro-5-oxo-1,4,5,6-tetrahydro-1,6-naphthyridin-4-yl)benzonitrile and 43 mg of triethyloxonium tetrafluoroborate (0.23 mmol) are mixed under a dry argon atmosphere. After addition of dichloromethane (5 ml), the suspension is stirred until a solution is obtained, then mixed with methanol and concentrated. The residue is purified by preparative HPLC to result in 13 mg (29% of theory) of the title compound as a white solid.

LC-MS (method 1): $R_t$=2.01 min; $[M+H]^+$=367

$^1$H-NMR (300 MHz, DMSO-d$_6$): δ=1.13 (t, 3H), 2.55 (s, 3H), 3.73 (s, 3H), 4.10 (m, 2H), 5.62 (s, 1H), 6.60 (d, 1H), 7.31 (dd, 1H), 7.37 (d, 1H), 7.40 (d, 1H), 7.85 (d, 1H), 10.36 (s, 1H).

Example 35

4-(4-Cyano-2-methoxyphenyl)-5-ethoxy-2,7-dimethyl-1,4-dihydro-1,6-naphthyridine-3-carbonitrile

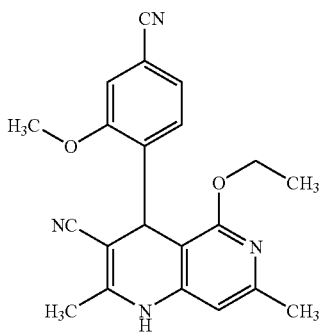

1920 mg (5.77 mmol) of 4-(4-cyano-2-methoxyphenyl)-2,7-dimethyl-5-oxo-1,4,5,6-tetrahydro-1,6-naphthyridine-3-carbonitrile are suspended in 40 ml (240 mmol) of anhydrous triethyl orthoformate. The reaction mixture is heated to 130° C. Then 10 drops of concentrated sulfuric acid are added each hour. After complete reaction has been detected (analytical HPLC; reaction time about 36 h), the reaction mixture is cooled to room temperature, and the volatile components are removed in a rotary evaporator. The crude product is purified by column chromatography (silica gel; mobile phase: cyclohexane/ethyl acetate 1:1). The product obtained in this way is crystallized from ethyl acetate. 451 mg (22% of theory) of the title compound are obtained as a white solid.

LC-MS (method 12): R$_t$=3.42 min; [M+H]$^+$ (EIpos): m/z=361

$^1$H-NMR (300 MHz, DMSO-d$_6$): δ=0.95 (t, 3H), 2.05 (s, 3H), 2.24 (s, 3H), 3.85 (s, 3H), 4.00 (m, 2H), 5.14 (s, 1H), 6.30 (s, 1H), 7.06 (d, 1H), 7.33 (d, 1H), 7.47 (s, 1H), 9.63 (s, 1H).

Example 36 ent-4-(4-Cyano-2-methoxyphenyl)-5-ethoxy-2,7-dimethyl-1,4-dihydro-1,6-naphthyridine-3-carbonitrile (−)-Enantiomer and (+)-Enantiomer

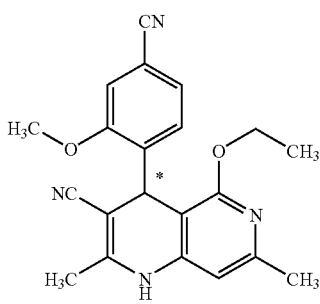

The racemate from example 35 can be fractionated into its enantiomers on a preparative scale by HPLC on a chiral phase [column: 680 mm×40 mm; silica gel phase based on the chiral selector poly(N-methacryloyl-D-leucine dicyclopropylmethylamide; eluent: ethyl acetate/isohexane 2:1 (v/v); temperature: 24° C.; flow rate: 80 ml/min; UV detection: 220 nm].

(−)-Enantiomer:

HPLC: R$_t$=3.15 min, ee=99.5% [column: 250 mm×4.6 mm; silica gel phase based on the chiral selector poly(N-methacryloyl-D-leucine dicyclopropylmethylamide; eluent: ethyl acetate/isohexane 2:3 (v/v); temperature: 25° C.; flow rate: 2 ml/min; UV detection: 220 nm];

specific rotation (chloroform, 589 nm, 19.9° C., c=0.48500 g/100 ml): −466.4°.

(+)-Enantiomer:

HPLC: R$_t$=3.96 min, ee=98% [column: 250 mm×4.6 mm; silica gel phase based on the chiral selector poly(N-methacryloyl-D-leucine dicyclopropylmethylamide; eluent: ethyl acetate/isohexane 2:3 (v/v); temperature: 25° C.; flow rate: 2 ml/min; UV detection: 220 nm];

specific rotation (chloroform, 589 nm, 20.1° C., c=0.34000 g/100 ml): +465.1°.

Example 37

4-(4-Cyano-2-methoxyphenyl)-5-ethoxy-2,8-dimethyl-1,4-dihydro-1,6-naphthyridine-3-carbonitrile

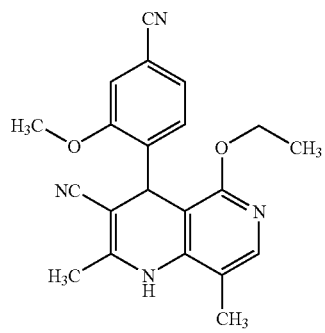

3620 mg (10.83 mmol) of 4-(4-cyano-2-methoxyphenyl)-2,8-dimethyl-5-oxo-1,4,5,6-tetrahydro-1,6-naphthyridine-3-carbonitrile are suspended in 150 ml (901 mmol) of anhydrous triethyl orthoformate. The reaction mixture is heated to 140° C. Then 10 drops of concentrated sulfuric acid are added each hour. After complete reaction has been detected (analytical HPLC; reaction time about 36 h), the reaction mixture is cooled to room temperature and the precipitated product is filtered off. The precipitate is washed with ethyl acetate and diethyl ether and then purified by flash chromatography (silica gel; mobile phase: initially dichloromethane, then isohexane/ethyl acetate 1:1). The product fractions are combined and concentrated in a rotary evaporator, and the residue is then crystallized from ethyl acetate. Drying under high vacuum results in 1160 mg (30% of theory) of the title compound in the form of yellowish crystals.

LC-MS (method 13): R$_t$=3.21 min; [M+H]$^+$ (EIpos): m/z=361

$^1$H-NMR (300 MHz, DMSO-$d_6$): δ=0.95 (t, 3H), 2.14 (s, 3H), 2.15 (s, 3H), 3.85 (s, 3H), 3.99 (m, 2H), 5.19 (s, 1H), 7.06 (d, 1H), 7.33 (d, 1H), 7.46 (s, 1H), 7.67 (s, 1H), 8.66 (s, 1H).

Example 38 ent-4-(4-Cyano-2-methoxyphenyl)-5-ethoxy-2,8-dimethyl-1,4-dihydro-1,6-naphthyridine-3-carbonitrile (−)-Enantiomer and (+)-Enantiomer

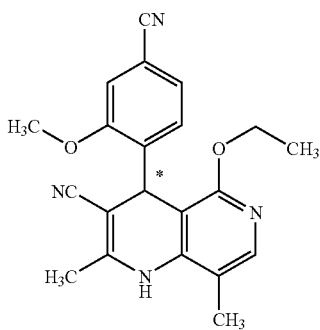

The racemate from example 37 can be fractionated into its enantiomers on a preparative scale by HPLC on a chiral phase [column: 670 mm×40 mm; silica gel phase based on the chiral selector poly(N-methacryloyl-D-leucine tert-butylamide; eluent: ethyl acetate/isohexane 7:3 (v/v); temperature: 24° C.; flow rate: 80 ml/min; UV detection: 220 nm].

(−)-Enantiomer:

HPLC: $R_t$=3.80 min, ee >99.8% [column: 250 mm×4.6 mm; silica gel phase based on the chiral selector poly(N-methacryloyl-L-leucine tert-butylamide; eluent: ethyl acetate/isohexane 1:1 (v/v); temperature: 25° C.; flow rate: 1 ml/min; UV detection: 220 nm];

specific rotation (chloroform, 589 nm, 19.6° C., c=0.28000 g/100 ml): −387.0°.

(+)-Enantiomer:

HPLC: $R_t$=4.46 min, ee=99.6% [column: 250 mm×4.6 mm; silica gel phase based on the chiral selector poly(N-methacryloyl-L-leucine tert-butylamide; eluent: ethyl acetate/isohexane 1:1 (v/v); temperature: 25° C.; flow rate: 1 ml/min; UV detection: 220 nm];

specific rotation (chloroform, 589 nm, 20.1° C., c=0.39500 g/100 ml): +397.1°.

B. Assessment of the Pharmacological Activity

Abbreviations

DMEM Dulbecco's modified Eagle medium
DNA deoxyribonucleic acid
FCS fetal calf serum
HEPES 4-(2-hydroxyethyl)-1-piperazineethanesulfonic acid
PCR polymerase chain reaction
Tris tris-(hydroxymethyl)methylamine The advantageous pharmacological properties of the compounds of the invention can be shown in the following assays:

1. Cellular In Vitro Assay to Determine the Inhibitory MR Activity and MR Selectivity Compared with other Steroid Hormone Receptors Antagonists of the human mineralocorticoid receptor (MR) are identified, and the activity of the compounds described herein is quantified with the aid of a recombinant cell line. The cell is originally derived from a hamster ovary epithelial cell (Chinese Hamster Ovary, CHO K1, ATCC: American Type Culture Collection, VA 20108, USA).

An established chimera system in which the ligand-binding domains of human steroid hormone receptors are fused to the DNA-binding domain of the yeast transcription factor GAL4 is used in this CHO K1 cell line. The GAL4-steroid hormone receptor chimeras produced in this way are cotransfected and stably expressed with a reporter construct in the CHO cells.

Clonings:

To generate the GAL4-steroid hormone receptor chimeras, the GAL4 DNA binding domain (amino acids 1-147) from the vector pFC2-dbd (from Stratagene) is cloned with the PCR-amplified ligand-binding domains of the mineralocorticoid receptor (MR, amino acids 734-985), of the glucocorticoid receptor (GR, amino acids 443-777), of the progesterone receptor (PR, amino acids 680-933) and of the androgen receptor (AR, amino acids 667-919) into the vector pIRES2 (from Clontech). The reporter construct, which comprises five copies of the GAL4 binding site upstream of a thymidine kinase promoter, leads to expression of firefly-luciferase (*Photinus pyralis*) after activation and binding of the GAL4-steroid hormone receptor chimeras by the respective specific agonists aldosterone (MR), dexamethasone (GR), progesterone (PR) and dihydrotestosterone (AR).

Assay Procedure:

The MR, GR, PR and AR cells are plated out in medium (Optimem, 2.5% FCS, 2 mM glutamine, 10 mM HEPES) in 96- (or 384- or 1536-) well microtiter plates on the day before the assay and are kept in a cell incubator (96% humidity, 5% v/v $CO_2$, 37° C.). On the day of the assay, the substances to be tested are taken up in the abovementioned medium and added to the cells. About 10 to 30 minutes after addition of the test substances, the respective specific agonists of the steroid hormone receptors are added. After a further incubation time of 5 to 6 hours, the luciferase activity is measured with the aid of a video camera. The measured relative light units as a function of the substance concentration result in a sigmoidal stimulation curve. The $IC_{50}$ values are calculated with the aid of the GraphPad PRISM computer program (Version 3.02).

Table A shows the $IC_{50}$ values (MR) of representative exemplary compounds:

TABLE A

| Example No. | MR $IC_{50}$ [nM] |
|---|---|
| 4 | 273 |
| 10 | 75 |
| 21 | 30 |
| 24 | 31 |
| 25 | 87 |
| 32 | 4 |
| 33 | 35 |
| 35 | 122 |
| 36 | 55 |
| [(−)-enantiomer] | |
| 37 | 73 |
| 38 | 25 |
| [(−)-enantiomer] | |

2. In Vitro Assay to Determine Possible Binding Activity to the L-Type Calcium Channel Membrane preparations of the cerebral cortex of Wistar rats serve as starting material for a radioactive binding assay which is described in detail in the literature as standard assay [Ehlert, F. J., Roeske, W. R., Itoga E., Yamamura, H. I., *Life Sci.* 30, 2191-2202 (1982); Gould, R. J., Murphy, K. M. M., Snyder, S. H., *Proc. Natl. Acad. Sci. U.S.A.* 79, 3656-3660] and is used in contract investigations by commercial service suppliers (e.g. MDS Pharma Services). In this binding assay, serial dilutions of the test compounds in DMSO are incubated with the membrane preparations and the tritium-labeled ligand nitrendipine (0.1 nM) in a 50 mM TrisHCl buffer, pH 7.7, at 25° C. typically for 90 minutes, and the specific binding of the test compounds is determined by quantifying the specifically displaced, radiolabeled ligand. $IC_{50}$ values are determined by a nonlinear regression analysis.

The $IC_{50}$ value determined in this L-type calcium channel binding assay for a conventional calcium antagonist of the dihydropyridine type such as, for example, nitrendipine is 0.3 nM, whereas the $IC_{50}$ values for investigated examples of the compounds of the invention described herein are >1 µM and thus the affinity shown for the L-type calcium channel is reduced by a factor of at least 3000. Compounds with such a low residual binding affinity for the L-type calcium channel no longer show pronounced hemodynamic effects mediated by the L-type calcium channel in vivo.

3. In Vitro Assay for Functional Characterization of Possible Calcium Channel-Agonistic or -Antagonistic Effects of Test Compounds: Potassium Chloride-Induced Stimulation of the Isolated Rabbit Aorta The freshly isolated thoracic aorta of male New Zealand white rabbits is removed and cleaned of surrounding tissue. Then aortic rings with a length of 2 mm are put under an initial tension of 4 g in 10 ml organ baths with Krebs-Henseleit solution at 37° C. Contractions are induced by 40 mM KCl (submaximal contraction) and 15 mM KCl (minimal contraction) four times at an interval of 45 minutes in order to train the vessels and generate a stable resting tension. Each contraction is followed by a series of eleven rinsing cycles and a resting period of 30 minutes with previous retensioning. After the four pre-runs, the test substances are added to the organ baths in each case at the start of the resting period without further retensioning. The concentration of the test substances is increased by a factor of 10 for each of the four following contractions. To calculate the effect, the difference between the baseline tension and the value for the fourth pre-run contraction is set equal to 100%, and the following contraction peaks are related to this value. This experimental procedure makes it possible to differentiate calcium-agonistic (slight increase at the submaximal contraction, greater increase at the minimal contraction) and calcium-antagonistic effect of the substance (reduction at the submaximal contraction, greater reduction at the minimal contraction).

The $IC_{50}$ measured for a classical calcium antagonist of the dihydropyridine type such as, for example, nifedipine in this functional assay on an isolated organ is from 0.1 nM to 0.4 nM, whereas the $IC_{50}$ values for investigating the examples of the compounds of the invention described herein are of the order of 4 to 25 µM, and thus the affinity shown for the L-type calcium channel is reduced by a factor of at least 10 000. Compounds with such a low residual binding affinity for the L-type calcium channel no longer show pronounced hemodynamic effects mediated by the L-type calcium channel in vivo.

4. In Vivo Assay for Detecting the Cardiovascular Effect: Diuresis Investigations on Conscious Rats in Metabolism Cages Wistar rats (bodyweight 250-350 g) are kept with free access to feed (Altromin) and drinking water. From about 72 hours before the start of the test, the animals receive instead of the normal feed exclusively salt-reduced feed with a sodium chloride content of 0.02% (ssniff RIM-H, 10 mm with 0.02% Na, S0602-E081, ssniff Spezialdäten GmbH, D-59494 Soest). During the test, the animals are housed singly in metabolism cages suitable for rats of this weight class (from Tecniplast Germany GmbH, D-82383 Hohenpeißenberg) with free access to salt-reduced feed and drinking water for about 24 hours. At the start of the test, the substance to be tested is administered into the stomach by means of gavage in a volume of 0.5 ml/kg of bodyweight of a suitable solvent. Control animals receive only solvent. Controls and substance tests are carried out in parallel on the same day. Control groups and substance-dose groups each consist of 3 to 6 animals. During the test, the urine excreted by the animals is continuously collected in a receiver on the base of the cage. The urine volume per unit time is determined separately for each animal, and the concentration of the sodium and potassium ions excreted in the urine is measured by standard methods of flame photometry. The sodium/potassium ratio is calculated from the measurements as a measure of the effect of the substance. The measurement intervals are typically the period up to 8 hours after the start of the test (day interval) and the period from 8 to 24 hours after the start of the test (night interval). In a modified test design, the urine is collected and measured at intervals of two hours during the day interval. In order to obtain a sufficient amount of urine for this purpose, the animals receive a defined amount of water by gavage at the start of the test and then at intervals of two hours.

5. DOCA/Salt Model

Administration of deoxycorticosterone acetate (DOCA) in combination with a high-salt diet and unilateral kidney removal in rats induces hypertension which is characterized by relatively low renin levels. As a consequence of this endocrine hypertension (DOCA is a direct precursor of aldosterone), there is, depending on the chosen DOCA concentration, cardiac hypertrophy and further end organ damage, e.g. of the kidney, which is characterized inter alia by protein urea and glomerulosclerosis. It is thus possible to investigate test substances in this rat model for the presence of an antihypertrophic and end organ-protecting effect.

Approximately 8-week old (body weight between 250 and 300 grams) male Sprague-Dawley (SD) rats undergo left uninephrectomy. For this purpose, the rats are anesthetized with 1.5-2% isoflurane in a mixture of 66% $N_2O$ and 33% $O_2$, and the kidney is removed through a flank incision. So-called sham-operated animals from which no kidney is removed serve as later control animals.

Uninephrectomized SD rats receive 1% sodium chloride in the drinking water and a subcutaneous injection of deoxycorticosterone acetate (dissolved in sesame oil; from Sigma) injected between the shoulder blades once a week (high dose: 100 mg/kg/week s.c.; normal dose: 30 mg/kg/week s.c.).

The substances which are to be investigated for their protective effect in vivo are administered by gavage or via the feed (from Ssniff). One day before the start of the test, the animals are randomized and assigned to groups with an identical number of animals, usually n=10, Throughout the test, drinking water and feed are available ad libitum to the animals. The substances are administered via the feed or once a day by gavage for 4-8 weeks. Animals serving as placebo group are treated in the same way but receive either only the solvent or the feed without test substance.

The effect of the test substances is determined by measuring hemodynamic parameters [blood pressure, heart rate, inotropism (dp/dt), relaxation time (tau), maximum left ventricular pressure, left-ventricular end-diastolic pressure (LVEDP)], determining the weight of the heart, kidney and lung, measuring the protein excretion, and by measuring gene expression of biomarkers (e.g. ANP, atrial natriuretic peptide, and BNP, brain natriuretic peptide) by means of RT/TaqMan PCR after RNA isolation from cardiac tissue.

Statistical analysis takes place using Student's t test after previous examination of the variances for homogeneity.

C. Exemplary Embodiments of Pharmaceutical Compositions

The compounds of the invention can be converted into pharmaceutical preparations in the following ways:

Tablet:

Composition:

100 mg of the compound of the invention, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm

Production:

The mixture of compound of the invention, lactose and starch is granulated with a 5% strength solution (m/m) of the PVP in water. The granules are mixed with the magnesium stearate for 5 minutes after drying. This mixture is compressed with a conventional tablet press (see above for format of the tablet). A guideline compressive force for the compression is 15 kN.

Suspension which can be Administered Orally:

Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol, and the compound of the invention is added to the suspension. The water is added while stirring. The mixture is stirred for about 6 h until the swelling of the Rhodigel is complete.

Solution which can be Administered Orally:

Composition:

500 mg of the compound of the invention, 2.5 g of polysorbate and 97 g of polyethylene glycol 400. 20 g of oral solution correspond to a single dose of 100 mg of the compound according to the invention.

Production:

The compound of the invention is suspended in the mixture of polyethylene glycol and polysorbate with stirring. The stirring process is continued until the compound according to the invention has completely dissolved.

i.v. Solution:

The compound of the invention is dissolved in a concentration below the saturation solubility in a physiologically tolerated solvent (e.g. isotonic saline solution, 5% glucose solution and/or 30% PEG 400 solution). The solution is sterilized by filtration and used to fill sterile and pyrogen-free injection containers.

The invention claimed is:

1. A compound of the formula (I)

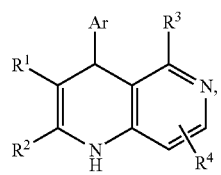

(I)

in which

Ar is a group of the formula

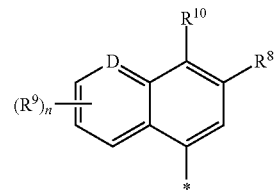

in which

* is the linkage point, $R^8$ is hydrogen or fluorine, $R^9$ is halogen, $(C_1-C_4)$-alkyl, trifluoromethyl, $(C_1-C_4)$-alkoxy or trifluoromethoxy, $R^{10}$ is cyano or nitro, D is CH, C—$R^9$ or N, and n is the number 0, 1 or 2, it being possible in the case where the substituent $R^9$ occurs more than once for its meanings to be identical or different, $R^1$ is cyano, nitro or a group of the formula —C(=O)—$R^{13}$ in which $R^{13}$ is $(C_1-C_6)$-alkyl which may be substituted by $(C_3-C_7)$-cycloalkyl or once to three times by fluorine, or phenyl which may be substituted by halogen, cyano, $(C_1-C_4)$-alkyl, trifluoromethyl, $(C_1-C_4)$-alkoxy or trifluoromethoxy, or $(C_3-C_7)$-cycloalkyl, $R^2$ is $(C_1-C_4)$-alkyl, trifluoromethyl, cyclopropyl, cyclobutyl, $(C_1-C_4)$-alkoxy or $(C_1-C_4)$-alkylthio, $R^3$ is $(C_1-C_6)$-alkyl, $(C_1-C_6)$-alkoxy, trifluoromethoxy, $(C_1-C_6)$-alkylthio, amino, mono-$(C_1-C_6)$-alkylamino or a group of the formula —O—$SO_2$—$R^{14}$, where said $(C_1-C_6)$-alkyl, $(C_1-C_6)$-alkoxy and $(C_1-C_6)$-alkylthio radicals may in each case be substituted by $(C_3-C_7)$-cycloalkyl, and $R^{14}$ is $(C_1-C_6)$-alkyl, trifluoromethyl, $(C_3-C_7)$-cycloalkyl, phenyl or 5- or 6-membered heteroaryl having up to two heteroatoms from the series N, O and/or S, it being possible for phenyl and heteroaryl in turn each to be substituted once or twice, identically or differently, by halogen, cyano, nitro, $(C_1-C_4)$-alkyl, trifluoromethyl, $(C_1-C_4)$-alkoxy and/or trifluoromethoxy, and $R^4$ is hydrogen, fluorine, $(C_1-C_4)$-alkyl, trifluoromethyl, $(C_1-C_4)$-alkoxy, trifluoromethoxy, $(C_1-C_4)$-alkylthio, amino, mono-$(C_1-C_4)$-alkylamino or di-$(C_1-C_4)$-alkylamino, and the salts thereof.

2. A compound of claim 1, in which
Ar is a group of the formula

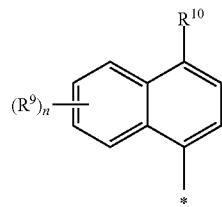

in which
* is the linkage point,
$R^9$ is fluorine, chlorine, methyl or ethyl,
$R^{10}$ is cyano or nitro,
and
n is the number 0 or 1,
$R^1$ is cyano, acetyl or trifluoroacetyl,
$R^2$ is methyl or trifluoromethyl,
$R^3$ is $(C_1-C_4)$-alkoxy, trifluoromethoxy or a group of the formula $-O-SO_2-R^{14}$ in which
$R^{14}$ is $(C_1-C_4)$-alkyl, trifluoromethyl, $(C_3-C_6)$-cycloalkyl, phenyl or thienyl, where phenyl and thienyl in turn may each be substituted once or twice, identically or differently by fluorine, chlorine, cyano, methyl, trifluoromethyl, methoxy and/or trifluoromethoxy,
and
$R^4$ is hydrogen, fluorine or methyl.

3. A process for preparing compounds of the formula (I) as defined in claim 1, in which $R^3$ is optionally $(C_3-C_7)$-cycloalkyl-substituted $(C_1-C_6)$-alkoxy, trifluoromethoxy or a group of the formula $-O-SO_2-R^{14}$ in which $R^{14}$ has the meaning indicated in claim 1, characterized in that a compound of the formula (II)

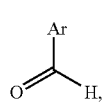

in which Ar has the meaning indicated in claim 1,
either
[A] is reacted in a one-stage (one-pot reaction) or two-stage process with a compound of the formula (III)

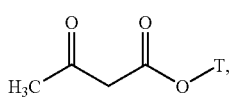

in which
T is methyl or ethyl,
and a compound of the formula (IV)

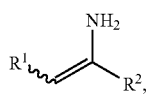

in which $R^1$ and $R^2$ have the meanings indicated in claim 1,
to give a compound of the formula (V)

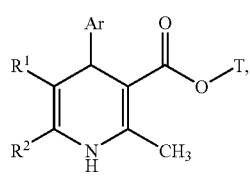

in which Ar, $R^1$, $R^2$ and T each have the meanings indicated above, and the latter is then reacted in an inert solvent with s-triazine in the presence of a base to give a compound of the formula (VIa)

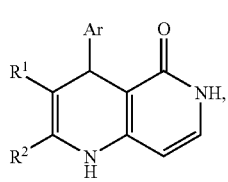

in which Ar, $R^1$ and $R^2$ each have the meanings indicated above,
Or
[B] is reacted in a one-stage (one-pot reaction) or two-stage process with a compound of the formula (VII)

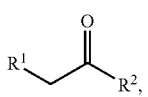

in which $R^1$ and $R^2$ have the meanings indicated in claim 1,
and a compound of the formula (VIII)

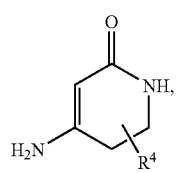

in which $R^4$ has the meaning indicated in claim 1,
to give a compound of the formula (VI)

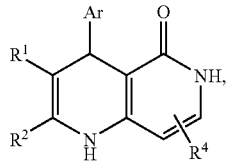
(VI)

in which Ar, $R^1$, $R^2$ and $R^4$ each have the meanings indicated above,
and then the compounds of the formula (VIa) or (VI) are alkylated in an inert solvent, where appropriate in the presence of a base, with a compound of the formula (IX) or a trialkyloxonium salt of the formula (X)

$$R^{15}-X \quad \text{(IX)}$$

$$\underset{R^{15A}}{\overset{R^{15A}}{\underset{|}{O^+}}}\; R^{15A} \quad Y^- \quad \text{(X)}$$

in which
  $R^{15}$ is $(C_1-C_6)$-alkyl which may be substituted by $(C_3-C_7)$-cycloalkyl or is trifluoromethyl,
  $R^{15A}$ is methyl or ethyl,
  X is a leaving group such as, for example, halogen, mesylate, tosylate or triflate,
and
  $Y^-$ is a non-nucleophilic anion such as, for example, tetrafluoroborate,
or in the presence of an acid with an orthoformic ester of the formula (XI)

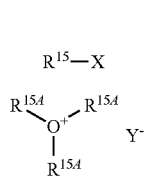
(XI)

in which $R^{15A}$ has the meaning indicated above,
to give compounds of the formula (I-A)

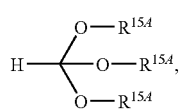
(I-A)

in which Ar, $R^1$, $R^2$, $R^4$ and $R^{15}$ each have the meanings indicated above, or the compounds of the formula (VIa) or (VI) are reacted in an inert solvent in the presence of a base with a compound of the formula (XII)

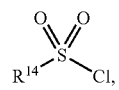
(XII)

in which $R^{14}$ has the meaning indicated in claim 1,
to give compounds of the formula (I-B)

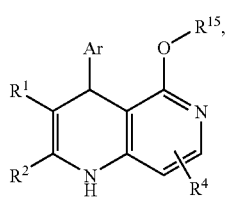
(I-B)

in which Ar, $R^1$, $R^2$, $R^4$ and $R^{14}$ each have the meanings indicated in claim 1, and where appropriate the resulting compounds of the formula (I-A) or (I-B) are separated by methods known to the skilled worker into their enantiomers and/or diastereomers, and/or converted with the appropriate (i) solvents and/or (ii) bases or acids into salts thereof.

4. A pharmaceutical composition comprising a compound of the formula (I) as defined in claim 1 in combination with an inert, non-toxic, pharmaceutically suitable excipient.

5. A pharmaceutical composition comprising a compound of the formula (I) as defined in claim 1 in combination with one or more further active ingredients selected from the group consisting of ACE inhibitors, renin inhibitors, angiotensin II receptor antagonists, beta-blockers, acetylsalicylic acid, diuretics, potassium supplements, calcium antagonists, statins, digitalis (digoxin) derivatives, calcium sensitizers, nitrates and antithrombotics.

\* \* \* \* \*